(12) United States Patent
Tabuteau

(10) Patent No.: US 9,457,023 B1
(45) Date of Patent: *Oct. 4, 2016

(54) COMPOSITIONS AND METHODS FOR INCREASING THE METABOLIC LIFETIME OF DEXTROMETHORPHAN AND RELATED PHARMACODYNAMIC EFFECTS

(71) Applicant: ANTECIP BIOVENTURES II LLC, New York, NY (US)

(72) Inventor: Herriot Tabuteau, New York, NY (US)

(73) Assignee: ANTECIP BIOVENTURES II LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/164,746

(22) Filed: May 25, 2016

Related U.S. Application Data

(63) Continuation-in-part of application No. 14/879,002, filed on Oct. 8, 2015, now Pat. No. 9,375,429, which is a continuation of application No. 14/554,988, filed on Nov. 26, 2014, now Pat. No. 9,205,083, which is a continuation of application No. 14/550,618, filed on Nov. 21, 2014, now Pat. No. 9,198,905, which is a continuation-in-part of application No. PCT/US2014/064184, filed on Nov. 5, 2014.

(60) Provisional application No. 61/900,354, filed on Nov. 5, 2013.

(51) Int. Cl.
  A61K 31/137 (2006.01)
  A61K 31/485 (2006.01)
  A61K 31/4748 (2006.01)
  A61K 31/135 (2006.01)

(52) U.S. Cl.
  CPC ......... *A61K 31/4748* (2013.01); *A61K 31/135* (2013.01); *A61K 31/137* (2013.01)

(58) Field of Classification Search
  None
  See application file for complete search history.

(56) References Cited

U.S. PATENT DOCUMENTS

| | | | |
|---|---|---|---|
| 2,676,177 A | 4/1954 | Schnider et al. | |
| 3,819,706 A | 6/1974 | Mehta | |
| 4,687,660 A | 8/1987 | Baker et al. | |
| 5,166,207 A | 11/1992 | Smith | |
| 5,206,248 A | 4/1993 | Smith | |
| 5,350,756 A | 9/1994 | Smith | |
| 6,034,091 A | 3/2000 | Dante | |
| 6,197,830 B1 | 3/2001 | Frome | |
| 6,207,674 B1 | 3/2001 | Smith | |
| 6,333,332 B1 | 12/2001 | Han et al. | |
| 6,436,938 B1 | 8/2002 | Howard | |
| 6,562,835 B1 | 5/2003 | Caruso | |
| 6,608,073 B1 | 8/2003 | Hussain et al. | |
| 6,780,871 B2 | 8/2004 | Glick et al. | |
| 6,897,241 B2 | 5/2005 | Frome | |
| 7,569,610 B2 | 8/2009 | Oberegger et al. | |
| 7,569,611 B2 | 8/2009 | Oberegger et al. | |
| 7,579,380 B2 | 8/2009 | Oberegger et al. | |
| 7,659,282 B2 | 2/2010 | Yakatan et al. | |
| 7,674,479 B2 | 3/2010 | Zerbe et al. | |
| 7,884,136 B2 | 2/2011 | Oberegger et al. | |
| 7,973,043 B2 | 7/2011 | Migaly | |
| 7,973,049 B2 | 7/2011 | Tung | |
| 8,017,623 B2 | 9/2011 | Singh | |
| 8,188,110 B2 | 5/2012 | Tung | |
| 8,227,484 B2 | 7/2012 | Yakatan et al. | |
| 8,461,102 B2 | 6/2013 | Royster | |
| 8,541,436 B2 | 9/2013 | Tung | |
| 8,569,328 B1 | 10/2013 | Tabuteau | |
| 8,728,528 B2 | 5/2014 | Biggs et al. | |
| 8,796,302 B2 | 8/2014 | Hong et al. | |
| 8,932,628 B2 | 1/2015 | Oberegger et al. | |
| 9,168,234 B2 | 10/2015 | Tabuteau | |
| 9,198,905 B2 | 12/2015 | Tabuteau | |
| 9,205,083 B2 | 12/2015 | Tabuteau | |
| 9,238,032 B2 | 1/2016 | Tabuteau | |
| 9,278,095 B2 | 3/2016 | Tabuteau | |
| 9,314,462 B2 | 4/2016 | Tabuteau | |
| 9,370,513 B2 | 6/2016 | Tabuteau | |
| 9,375,429 B2 | 6/2016 | Tabuteau | |
| 2002/0004078 A1 | 1/2002 | Gelber et al. | |
| 2002/0103109 A1 | 8/2002 | Glick et al. | |
| 2004/0092511 A1 | 5/2004 | Billstein et al. | |
| 2005/0085463 A1 | 4/2005 | Weiner et al. | |
| 2005/0203125 A1 | 9/2005 | Yakatan et al. | |

(Continued)

FOREIGN PATENT DOCUMENTS

| | | |
|---|---|---|
| EP | 1224930 | 7/2002 |
| EP | 2397158 | 12/2011 |

(Continued)

OTHER PUBLICATIONS

Applicant's Remarks filed on Jul. 1, 2015 for the prosecution of case U.S. Appl. No. 14/604,397.*
U.S. Appl. No. 14/628,062, filed Feb. 20, 2015 First Named Inventor: Herriot Tabuteau Assignee: Antecip Bioventures II LLC.
U.S. Appl. No. 14/863,284, filed Sep. 23, 2015 First Named Inventor: Herriot Tabuteau Assignee: Antecip Bioventures II LLC.
U.S. Appl. No. 14/878,998, filed Oct. 8, 2015 First Named Inventor: Herriot Tabuteau Assignee: Antecip Bioventures II LLC.
U.S. Appl. No. 14/879,002, filed Oct. 8, 2015 First Named Inventor: Herriot Tabuteau Assignee: Antecip Bioventures II LLC.
U.S. Appl. No. 14/978,976, filed Dec. 22, 2015 First Named Inventor: Herriot Tabuteau Assignee: Antecip Bioventures II LLC.

(Continued)

*Primary Examiner* — Bong-Sook Baek
(74) *Attorney, Agent, or Firm* — K&L Gates LLP; Brent A. Johnson; Louis C. Cullman

(57) ABSTRACT

This disclosure relates to methods administering various compounds in conjunction with dextromethorphan to a human being. Dosage forms, drug delivery systems, and methods related to dextromethorphan or dextrorphan and bupropion, hydroxybupropion, erythrohydroxybupropion, threohydroxybupropion, or a metabolite or prodrug of any of these compounds are also disclosed.

25 Claims, 12 Drawing Sheets

(56) References Cited

U.S. PATENT DOCUMENTS

| | | |
|---|---|---|
| 2005/0209218 A1 | 9/2005 | Meyerson et al. |
| 2005/0250767 A1 | 11/2005 | Weiner et al. |
| 2006/0258721 A1 | 11/2006 | Maddaford et al. |
| 2007/0042969 A1 | 2/2007 | Rauschkolb-Loffler et al. |
| 2008/0008748 A1 | 1/2008 | Beyreuther et al. |
| 2008/0081072 A1 | 4/2008 | Cherukuri |
| 2008/0213217 A1 | 9/2008 | Storer et al. |
| 2008/0286344 A1 | 11/2008 | Darmuzey et al. |
| 2009/0124583 A1 | 5/2009 | Nelson et al. |
| 2009/0162421 A1 | 6/2009 | Geisslinger et al. |
| 2009/0191257 A1 | 7/2009 | Smith |
| 2010/0029665 A1 | 2/2010 | Meyerson et al. |
| 2011/0039875 A1 | 2/2011 | Singh |
| 2011/0217371 A1 | 9/2011 | Shin et al. |
| 2011/0245208 A1 | 10/2011 | Diatchenko et al. |
| 2012/0053169 A1 | 3/2012 | Thomas |
| 2012/0083487 A1 | 4/2012 | Thomas |
| 2012/0252833 A1 | 10/2012 | Wertz et al. |
| 2013/0137714 A1 | 5/2013 | Berg |
| 2014/0162965 A1 | 6/2014 | Maggio |
| 2015/0087669 A1 | 3/2015 | Lammert et al. |
| 2015/0126541 A1 | 5/2015 | Tabuteau |
| 2015/0126542 A1 | 5/2015 | Tabuteau |
| 2015/0126543 A1 | 5/2015 | Tabuteau |
| 2015/0126544 A1 | 5/2015 | Tabuteau |
| 2015/0133485 A1 | 5/2015 | Tabuteau |
| 2015/0133486 A1 | 5/2015 | Tabuteau |
| 2015/0150830 A1 | 6/2015 | Tabuteau |
| 2015/0157582 A1 | 6/2015 | Tabuteau |
| 2016/0008352 A1 | 1/2016 | Tabuteau |
| 2016/0030420 A1 | 2/2016 | Tabuteau |
| 2016/0030421 A1 | 2/2016 | Tabuteau |
| 2016/0136155 A1 | 5/2016 | Tabuteau |
| 2016/0143901 A1 | 5/2016 | Siffert et al. |

FOREIGN PATENT DOCUMENTS

| | | |
|---|---|---|
| WO | 9850044 | 11/1998 |
| WO | 0041684 | 7/2000 |
| WO | 0059486 | 10/2000 |
| WO | 01/45708 A1 | 6/2001 |
| WO | 02/060425 A1 | 8/2002 |
| WO | 2004075832 | 9/2004 |
| WO | 2006092691 | 9/2006 |
| WO | 2009006194 | 1/2009 |
| WO | 2009011412 | 1/2009 |
| WO | 2009062318 | 5/2009 |
| WO | 2009062319 | 5/2009 |
| WO | 2010/010343 A1 | 1/2010 |
| WO | 2010000073 | 1/2010 |
| WO | 2010062690 | 6/2010 |
| WO | 2010062692 | 6/2010 |
| WO | 2012118562 | 9/2012 |
| WO | 2012118563 | 9/2012 |
| WO | 2013136078 | 9/2013 |
| WO | 2013158680 | 10/2013 |
| WO | 2013/190013 A1 | 12/2013 |
| WO | 2014100501 | 6/2014 |
| WO | 2014/138669 A1 | 9/2014 |

OTHER PUBLICATIONS

U.S. Appl. No. 14/997,316, filed Jan. 15, 2016 First Named Inventor: Herriot Tabuteau Assignee: Antecip Bioventures II LLC.
U.S. Appl. No. 15/057,983, filed Mar. 1, 2016 First Named Inventor: Herriot Tabuteau Assignee: Antecip Bioventures II LLC.
U.S. Appl. No. 15/130,807, filed Apr. 15, 2016 First Named Inventor: Herriot Tabuteau Assignee: Antecip Bioventures II LLC.
U.S. Appl. No. 15/164,746, filed May 25, 2016 First Named Inventor: Herriot Tabuteau Assignee: Antecip Bioventures II LLC.
U.S. Appl. No. 15/164,767, filed May 25, 2016 First Named Inventor: Herriot Tabuteau Assignee: Antecip Bioventures II LLC.
U.S. Appl. No. 15/206,057, filed Jul. 8, 2016 First Named Inventor: Herriot Tabuteau Assignee: Antecip Bioventures II LLC.
U.S. Appl. No. 15/182,253, filed Jun. 14, 2016 First Named Inventor: Herriot Tabuteau Assignee: Antecip Bioventures II LLC.
Wadhwa et al., Large-Dose Oral Dextromethorphan as an Adjunct to Patient-Controlled Analgesia with Morphine after Knee Surgery, Anesthesia & Analgesia, 92(2), 448-454, Feb. 2001.
Walker et al., An Open Label Trial of Dextromethorphan in Huntington's Disease, Clinical Neuropharmacology, 12(4), 322-330, Aug. 1989.
Weinbroum et al., The Role of Dextromethorphan in Pain Control, Canadian Journal of Anesthesia, 47(6), 585-596, Jun. 2000.
Zhu et al., CYP2B6 and Bupropion's Smoking-Cessation Pharmacology: The Role of Hydroxybupropion, Clinical Pharmacology & Therapeutics, 92(6), 771-777, Dec. 2012.
Abdel-Rahman et al., Potent Inhibition of Cytochrome P-450 2D6-mediated Dextromethorphan O-Demethylation by Terbinafine, Drug Metabolism and Disposition, 27(7), 770-775, Jul. 1999.
Bachmann, K., Chapter 12—Drug—drug interactions with an emphasis on drug metabolism and transport, Pharmacology Principles and Practice, Academic Press, 303-325, 2009.
Chyka et al., Dextromethorphan Poisoning: An Evidence-Based Consensus Guideline for Out-of-Hospital Management, Clinical Toxicology, 45(6): 662-677, Sep. 2007.
Desmeules et al., Contribution of Cytochrome P-4502D6 Phenotype to the Neuromodulatory Effects of Dextromethorphan, Journal of Pharmacology and Experimental Therapeutics, 288(2), 607-612, Feb. 1999.
Dextromethorphan Product Labeling Under the OTC Monograph 21 CFR 341.74, 1 pg., last accessed Nov. 2013.
Droll et al., Comparison of Three CYP2D6 Probe Substrates and Genotype in Ghanaians, Chinese and Caucasians, Pharmacogenetics and Genomics, 8(4), 325-333, Aug. 1998.
Drug Interactions between Dextromethorphan/Guaifenesin and WELLBUTRIN XL®, Drugs.com, last accessed Apr. 11, 2016, 1 pg., available at: http://www.drugs.com/drug-interactions/dextromethorphan-guaffenesin-with-wellbutrin-xl-846-0-440-2469.html.
Fairstein et al., Regional-Dependent Intestinal Permeability and BCS Classification: Elucidation of pH-Related Complexity in Rats Using Pseudoephedrine, The AAPS Journal, 15(2), 589-597, Apr. 2013.
Garnock-Jones, Dextromethorphan/Quinidine: In Pseudobulbar Affect, CNS Drugs, 25(5), 435-45, May 2011.
Gilron et al., A Randomized, Controlled Trial of High-Dose Dextromethorphan in Facial Neuralgias, Neurology, 55(7), 964-971, Oct. 2000.
Glaxosmithkline, Wellbutrin XL® Prescribing Information, 2009, 33 pgs., available at: http://www.accessdata.fda.gov/drugsatfda_docs/label/2009/021515s023s024lbl.pdf.
Glaxosmithkline, Zyban® Prescribing Information, Aug. 2011, 28 pgs, available at: http://www.accessdata.fda.gov/drugsatfda_docs/label/2011/020711s026lbl.pdf.
Güzey et al., Change from the CYP2D6 Extensive Metabolizer to the Poor Metabolizer Phenotype During Treatment with Bupropion, Therapeutic Drug Monitoring, 24(3), 436-437, Jun. 2002.
Howard et al., The Efficacy and Toxicity of Bupropion in the Elderly, Jefferson Journal of Psychiatry, 15(1), 34-38, Jan. 2000.
Humanwell Puracap Pharmaceutical (WUHAN), LTD., Dextromethorphan HBR, Prescribing information, 4 pgs., revised Jan. 2014.
Kelly et al., The Utility of the Combination of Dextromethorphan and Quinidine in the Treatment of Bipolar II and Bipolar NOS, Journal of Affective Disorders, 167, 333-335, Oct. 2014.
Kiptoo et al., Transdermal Delivery of Bupropion and its Active Metabolite, Hydroxybupropion: A Prodrug Strategy an Alternative Approach, Journal of Pharmaceutical Sciences, 98(2), 583-594, Feb. 2009.
Kotlyar et al., Inhibition of CYP2D6 Activity by Bupropion, Journal of Clinical Psychopharmacology, 25(2), 226-229, Jun. 2005.
Lauterbach, Dextromethorphan as a Potential Rapid-Acting Antidepressant, Medical Hypotheses, 76(5), 717-719, May 2011.

(56) References Cited

OTHER PUBLICATIONS

Lauterbach, An Extension of Hypotheses Regarding Rapid-Acting, Treatment-Refractory, and Conventional Antidepressant Activity of Dextromethorphan and Dextrorphan, Medical Hypotheses, 78(6), 693-702, Jun. 2012.
Lee et al., The DRD2/ANKK1 Gene is Associated with Response to Add-on Dextromethorphan Treatment in Bipolar Disorder, Journal of Affective Disorders, 138(3), 295-300, May 2012.
Mizoguchi et al., Efficacy of a Single Evening Dose of Syrup containing Paracetamol, Dextromethorophan Hydrobromide, Doxylamine Succinate and Ephedrine Sulfate in Subjects with Multiple Common Cold Symptoms, International Journal of Clinical Pharmacology and Therapeutics, 45(4), 230-236, Apr. 2007.
Nakashima et al., Effect of Cinacalcet Hydrochloride, a New Calcimimetic Agent, on the Pharmacokinetics of Dextromethorphan: In Vitro and Clinical Studies, The Journal of Clinical Pharmacology, 47(10), 1311-1319, Oct. 2007.
Nelson et al., High-Dose Oral Dextromethorphan Versus Placebo in Painful Diabetic Neuropathy and Postherpetic Neuralgia, Neurology, 48(5), 1212-1218, May 1997.
Nguyen et al., Involvement of Sigma-1 Receptors in the Antidepressant-like Effects of Dextromethorphan, PLOS One, 9(2), 9 pgs., Feb. 2014.
Olney et al., AVP-923, A Combination of Dextromethorphan Hydrobromide and Quinidine Sulfate for the Treatment of Pseudobulbar Affect and Neuropathic Pain, IDrugs: The Investigational Drugs Journal, 13(4), 254-265, Apr. 2010.
Pioro et al., Dextromethorphan Plus Ultra Low-Dose Quinidine Reduces Pseudobulbar Affect, Annals of Neurology, 68(5), 693-702, Nov. 2010.
Pope et al., Pharmacokinetics of Dextromethorphan after Single or Multiple Dosing in Combination with Quinidine in Extensive and Poor Metabolizers, The Journal of Clinical Pharmacology, 44(10), 1132-1142, Oct. 2004.
Reese et al., An in Vitro Mechanistic Study to Elucidate the Desipramine/Bupropion Clinical Drug-Drug Interaction, Drug Metabolism and Disposition, 36(7), 1198-1201, Jul. 2008.
Rosen, Dextromethorphan/Quinidine Sulfate (ZENVIA™) for Pseudobulbar Affect, Drugs of Today, 44(9), 661-668, Sep. 2008.
Rowley, Regulatory History and Background on Over-the-Counter Dextromethorphan, FDA Drug Safety and Risk Management Advisory Committee Meeting, Presentation, 21 pgs., Sep. 14, 2010.
Sang et al., Dextromethorphan and Memantine in Painful Diabetic Neuropathy and Postherpetic Neuralgia, Anesthesiology, 96(5), 1053-1061, May 2002.
Semenchuk et al., Efficacy of Sustained-Release Bupropion in Neuropathic Pain: An Open-Label Study, The Clinical Journal of Pain, 16(1), 6-11, Mar. 2000.
Semenchuk et al., Double-Blind, Randomized Trial of Bupropion SR for the Treatment of Neuropathic Pain, Neurology, 57(9), 1583-1588, Nov. 2001.
Shah et al., Bupropion for the Treatment of Neuropathic Pain, American Journal of Hospice & Palliative Medicine, 27(5), 333-336, Aug. 2010.
Shaibani et al., Efficacy and Safety of Dextromethorphan/Quinidine at Two Dosage Levels for Diabetic Neuropathic Pain: A Double-Blind, Placebo-Controlled, Multicenter Study, Pain Medicine, 13(2), 243-254, Feb. 2012.
Silverstone et al., Convulsive Liability of Bupropion Hydrochloride Metabolites in Swiss Albino Mice, Annals of General Psychiatry, 7(1), Article 19, 8 pgs, Oct. 2008.
Smith, Dextromethorphan/Quinidine: A Novel Dextromethorphan Product for the Treatment of Emotional Lability, Expert Opinion on Pharmacotherapy, 7(18), 2581-2598, Dec. 2006.
Spina et al., Clinically Relevant Pharmacokinetic Drug Interactions with Second-Generation Antidepressants: An Update, Clinical Therapeutics, 30(7), 1206-1227, Jul. 2008.
Struthers et al., Mecamylamine, Dihydro-β-Erythroidine, and Dextromethorphan Block Conditioned Responding Evoked by the Conditional Stimulus Effects of Nicotine, Pharmacology, Biochemistry and Behavior, 94(2), 319-328, Dec. 2009.
Thisted et al., Dextromethorphan and Quinidine in Adult Patients with Uncontrolled Painful Diabetic Peripheral Neuropathy: A 29-Day, Multicenter, Open-Label, Dose-Escalation Study, Clinical Therapeutics, 28(10), 1607-1618, Oct. 2006.
Tod et al., Quantitative Prediction of Cytochrome P450 (CYP) 2D6-Mediated Drug Interactions, Clinical Pharmacokinetics, 50(8), 519-530, Aug. 2011.
U.S. Appl. No. 13/478,023, filed May 22, 2012 First Named Inventor: Herriot Tabuteau Assignee: Antecip Bioventures II LLC.
U.S. Appl. No. 14/550,618, filed Nov. 21, 2014 First Named Inventor: Herriot Tabuteau Assignee: Antecip Bioventures II LLC.
U.S. Appl. No. 14/554,947, filed Nov. 26, 2014 First Named Inventor: Herriot Tabuteau Assignee: Antecip Bioventures II LLC.
U.S. Appl. No. 14/554,988, filed Nov. 26, 2014 First Named Inventor: Herriot Tabuteau Assignee: Antecip Bioventures II LLC.
U.S. Appl. No. 14/555,085, filed Nov. 26, 2014 First Named Inventor: Herriot Tabuteau Assignee: Antecip Bioventures II LLC.
U.S. Appl. No. 14/602,177, filed Jan. 21, 2015 First Named Inventor: Herriot Tabuteau Assignee: Antecip Bioventures II LLC.
U.S. Appl. No. 14/604,397, filed Jan. 23, 2015 First Named Inventor: Herriot Tabuteau Assignee: Antecip Bioventures II LLC.
U.S. Appl. No. 14/617,624, filed, Feb. 9, 2015 First Named Inventor: Herriot Tabuteau Assignee: Antecip Bioventures II LLC.
Jefferson, J.W., et al. (2005) "Bupropion for Major Depressive Disorder: Pharmacokinetic and Formulation considerations," Clinical Therapeutics: vol. 27(11), pp. 1685-1695.

* cited by examiner

COMPOSITIONS AND METHODS FOR INCREASING THE METABOLIC LIFETIME OF DEXTROMETHORPHAN AND RELATED PHARMACODYNAMIC EFFECTS

CROSS-REFERENCE TO RELATED APPLICATIONS

This application is a continuation-in-part of U.S. patent application Ser. No. 14/879,002, filed Oct. 8, 2015, which is a continuation of U.S. patent application Ser. No. 14/554,988, filed Nov. 26, 2014, now U.S. Pat. No. 9,205,083 which is a continuation of U.S. patent application Ser. No. 14/550,618, filed Nov. 21, 2014, now U.S. Pat. No. 9,198,905, which is a continuation-in-part of International Patent App. No. PCT/US2014/064184, filed Nov. 5, 2014, which claims the benefit of U.S. Provisional Patent App. No. 61/900,354, filed Nov. 5, 2013, all of which are incorporated by reference in their entireties.

SUMMARY

Some embodiments include a method of increasing dextromethorphan plasma levels in a human being, comprising co-administering bupropion, hydroxybupropion, erythrohydroxybupropion, threohydroxybupropion, or a metabolite or prodrug of any of these compounds with dextromethorphan.

Some embodiments include a method of increasing dextromethorphan plasma levels in a human being, comprising co-administering erythrohydroxybupropion or a prodrug thereof, with dextromethorphan to the human being, wherein the erythrohydroxybupropion or a prodrug thereof is administered in an amount that results in an $AUC_{0-12}$ of dextromethorphan that is at least about 40 ng·hr/mL.

Some embodiments include a method of increasing dextromethorphan plasma levels in a human being, comprising co-administering erythrohydroxybupropion or a prodrug thereof, with dextromethorphan to the human being, wherein the erythrohydroxybupropion or a prodrug thereof is administered in an amount that results in a $C_{max}$ of dextromethorphan that is at least about 6 ng/mL.

Some embodiments include method of increasing dextromethorphan plasma levels in a human being, comprising co-administering erythrohydroxybupropion or a prodrug thereof, with dextromethorphan to the human being, wherein the erythrohydroxybupropion or a prodrug thereof is administered in an amount that results in a $C_{avg}$ of dextromethorphan, over the period between two separate and consecutive administrations of dextromethorphan, that is at least about 5 ng/mL.

Some embodiments include a method of increasing the metabolic lifetime of dextromethorphan, comprising administering threohydroxybupropion, or a prodrug thereof, to a human being in need of treatment with dextromethorphan, wherein the human being is an extensive metabolizer of dextromethorphan, and wherein dextromethorphan is present in the body of the human being at the same time as threohydroxybupropion.

Some embodiments include a method of reducing an adverse event associated with treatment by dextromethorphan, comprising co-administering threohydroxybupropion, or a prodrug thereof, and dextromethorphan to a human patient in need of dextromethorphan treatment, wherein the human patient is at risk of experiencing the adverse event as a result of being treated with dextromethorphan.

Some embodiments include an oral sustained release delivery system for dextromethorphan, comprising bupropion, hydroxybupropion, erythrohydroxybupropion, threohydroxybupropion, or a prodrug of any of these compounds, dextromethorphan, and a water soluble vehicle.

Some embodiments include a method of decreasing the number of doses of dextromethorphan that can be administered without loss of efficacy, comprising orally administering an effective amount of bupropion, hydroxybupropion, erythrohydroxybupropion, threohydroxybupropion, or a prodrug of any of these compounds, to a human being in need of treatment with dextromethorphan.

Some embodiments include a method of decreasing dextrorphan plasma levels comprising co-administering threohydroxybupropion, or a prodrug thereof, and dextromethorphan to a human being in need of treatment with dextromethorphan, wherein the threohydroxybupropion, or a prodrug thereof, is administered on the first day of at least two days of treatment with dextromethorphan, wherein a decrease in the dextrorphan plasma level occurs on the first day that threohydroxybupropion, or a prodrug thereof, and dextromethorphan are co-administered, as compared to the same amount of dextromethorphan administered without threohydroxybupropion or a prodrug thereof.

Some embodiments include a method of decreasing dextrorphan plasma levels comprising co-administering hydroxybupropion, or a prodrug thereof, and dextromethorphan to a human being in need of treatment with dextromethorphan, wherein the hydroxybupropion, or a prodrug thereof, is administered on the first day of at least two days of treatment with dextromethorphan, wherein a decrease in the dextrorphan plasma level occurs on the first day that hydroxybupropion, or a prodrug thereof, and dextromethorphan are co-administered, as compared to the same amount of dextromethorphan administered without hydroxybupropion or a prodrug thereof.

Some embodiments include a method of decreasing dextrorphan plasma levels comprising co-administering bupropion and dextromethorphan to a human being in need of treatment with dextromethorphan, wherein the bupropion is administered on the first day of at least two days of treatment with dextromethorphan, wherein a decrease in the dextrorphan plasma level occurs on the first day that bupropion and dextromethorphan are co-administered, as compared to the same amount of dextromethorphan administered without bupropion.

Some embodiments include a method of decreasing dextrorphan plasma levels comprising co-administering erythrohydroxybupropion, or a prodrug thereof, and dextromethorphan to a human being in need of treatment with dextromethorphan, wherein the erythrohydroxybupropion, or a prodrug thereof, is administered on the first day of at least two days of treatment with dextromethorphan, wherein a decrease in the dextrorphan plasma level occurs on the first day that erythrohydroxybupropion, or a prodrug thereof, and dextromethorphan are co-administered, as compared to the same amount of dextromethorphan administered without erythrohydroxybupropion or a prodrug thereof.

Some embodiments include a method of decreasing dextrorphan plasma levels comprising co-administering bupropion and dextromethorphan, for at least eight consecutive days, to a human being in need of treatment with dextromethorphan, wherein, on the eighth day, the dextrorphan plasma level is lower than the dextrorphan plasma level that would have been achieved by administering the same amount of dextromethorphan administered without bupropion for eight consecutive days.

Some embodiments include a method of decreasing dextrorphan plasma levels comprising co-administering hydroxybupropion, or a prodrug thereof, and dextromethorphan, for at least eight consecutive days, to a human being in need of treatment with dextromethorphan, wherein, on the eighth day, the dextrorphan plasma level is lower than the dextrorphan plasma level that would have been achieved by administering the same amount of dextromethorphan administered without hydroxybupropion, or a prodrug thereof, for eight consecutive days.

Some embodiments include a method of decreasing dextrorphan plasma levels comprising co-administering erythrohydroxybupropion, or a prodrug thereof, and dextromethorphan, for at least eight consecutive days, to a human being in need of treatment with dextromethorphan, wherein, on the eighth day, the dextrorphan plasma level is lower than the dextrorphan plasma level that would have been achieved by administering the same amount of dextromethorphan administered without erythrohydroxybupropion, or a prodrug thereof, for eight consecutive days.

Some embodiments include a method of decreasing dextrorphan plasma levels comprising co-administering threohydroxybupropion, or a prodrug thereof, and dextromethorphan, for at least eight consecutive days, to a human being in need of treatment with dextromethorphan, wherein, on the eighth day, the dextrorphan plasma level is lower than the dextrorphan plasma level that would have been achieved by administering the same amount of dextromethorphan administered without threohydroxybupropion, or a prodrug thereof, for eight consecutive days.

Some embodiments include a method of decreasing dextrorphan plasma levels comprising co-administering bupropion and dextromethorphan, for at least nine consecutive days, to a human being in need of treatment with dextromethorphan, wherein, on the ninth day, the dextrorphan plasma level is lower than the dextrorphan plasma level that would have been achieved by administering the same amount of dextromethorphan administered without bupropion for nine consecutive days.

Some embodiments include a method of decreasing dextrorphan plasma levels comprising co-administering hydroxybupropion, or a prodrug thereof, and dextromethorphan, for at least nine consecutive days, to a human being in need of treatment with dextromethorphan, wherein, on the ninth day, the dextrorphan plasma level is lower than the dextrorphan plasma level that would have been achieved by administering the same amount of dextromethorphan administered without hydroxybupropion, or a prodrug thereof, for nine consecutive days.

Some embodiments include a method of decreasing dextrorphan plasma levels comprising co-administering erythrohydroxybupropion, or a prodrug thereof, and dextromethorphan, for at least nine consecutive days, to a human being in need of treatment with dextromethorphan, wherein, on the ninth day, the dextrorphan plasma level is lower than the dextrorphan plasma level that would have been achieved by administering the same amount of dextromethorphan administered without erythrohydroxybupropion, or a prodrug thereof, for nine consecutive days.

Some embodiments include a method of decreasing dextrorphan plasma levels comprising co-administering threohydroxybupropion, or a prodrug thereof, and dextromethorphan, for at least nine consecutive days, to a human being in need of treatment with dextromethorphan, wherein, on the ninth day, the dextrorphan plasma level is lower than the dextrorphan plasma level that would have been achieved by administering the same amount of dextromethorphan administered without threohydroxybupropion, or a prodrug thereof, for nine consecutive days.

Some embodiments include a method of decreasing dextrorphan plasma levels comprising co-administering bupropion and dextromethorphan, for at least nine consecutive days, to a human being in need of treatment with dextromethorphan, wherein, on the ninth day, the dextrorphan plasma level is lower than the dextrorphan plasma level that would have been achieved by administering the same amount of dextromethorphan administered without bupropion for nine consecutive days.

Some embodiments include a method of decreasing dextrorphan plasma levels comprising co-administering hydroxybupropion, or a prodrug thereof, and dextromethorphan, for at least nine consecutive days, to a human being in need of treatment with dextromethorphan, wherein, on the ninth day, the dextrorphan plasma level is lower than the dextrorphan plasma level that would have been achieved by administering the same amount of dextromethorphan administered without hydroxybupropion, or a prodrug thereof, for nine consecutive days.

Some embodiments include a method of decreasing dextrorphan plasma levels comprising co-administering erythrohydroxybupropion, or a prodrug thereof, and dextromethorphan, for at least nine consecutive days, to a human being in need of treatment with dextromethorphan, wherein, on the ninth day, the dextrorphan plasma level is lower than the dextrorphan plasma level that would have been achieved by administering the same amount of dextromethorphan administered without erythrohydroxybupropion, or a prodrug thereof, for nine consecutive days.

Some embodiments include a method of decreasing dextrorphan plasma levels comprising co-administering threohydroxybupropion, or a prodrug thereof, and dextromethorphan, for at least nine consecutive days, to a human being in need of treatment with dextromethorphan, wherein, on the ninth day, the dextrorphan plasma level is lower than the dextrorphan plasma level that would have been achieved by administering the same amount of dextromethorphan administered without threohydroxybupropion, or a prodrug thereof, for nine consecutive days.

Some embodiments include a method of decreasing dextrorphan plasma levels comprising co-administering bupropion and dextromethorphan, for at least ten consecutive days, to a human being in need of treatment with dextromethorphan, wherein, on the tenth day, the dextrorphan plasma level is lower than the dextrorphan plasma level that would have been achieved by administering the same amount of dextromethorphan administered without bupropion for ten consecutive days.

Some embodiments include a method of decreasing dextrorphan plasma levels comprising co-administering hydroxybupropion, or a prodrug thereof, and dextromethorphan, for at least ten consecutive days, to a human being in need of treatment with dextromethorphan, wherein, on the tenth day, the dextrorphan plasma level is lower than the dextrorphan plasma level that would have been achieved by administering the same amount of dextromethorphan administered without hydroxybupropion, or a prodrug thereof, for ten consecutive days.

Some embodiments include a method of decreasing dextrorphan plasma levels comprising co-administering erythrohydroxybupropion, or a prodrug thereof, and dextromethorphan, for at least ten consecutive days, to a human being in need of treatment with dextromethorphan, wherein, on the tenth day, the dextrorphan plasma level is lower than the dextrorphan plasma level that would have been achieved by administering the same amount of dextromethorphan administered without erythrohydroxybupropion, or a prodrug thereof, for ten consecutive days.

Some embodiments include a method of decreasing dextrorphan plasma levels comprising co-administering threohydroxybupropion, or a prodrug thereof, and dextromethorphan, for at least ten consecutive days, to a human being in need of treatment with dextromethorphan, wherein, on the tenth day, the dextrorphan plasma level is lower than the dextrorphan plasma level that would have been achieved by administering the same amount of dextromethorphan administered without threohydroxybupropion, or a prodrug thereof, for ten consecutive days.

Antidepressant compounds, such as bupropion, hydroxybupropion, erythrohydroxybupropion, threohydroxybupropion, or a metabolite or prodrug of any of these compounds, can be used to improve the therapeutic properties, such as in the treatment of neurological disorders, of dextromethorphan. Bupropion, hydroxybupropion, erythrohydroxybupropion, threohydroxybupropion, or a metabolite or prodrug of any of these compounds, regardless of stereochemistry, can be effective in inhibiting or reducing the metabolism of dextromethorphan in some human beings. This may be accomplished by co-administering bupropion, hydroxybupropion, erythrohydroxybupropion, threohydroxybupropion, or a metabolite or prodrug of any of these compounds, and dextromethorphan.

Some embodiments include a method of treating a neurological disorder comprising administering: 1) dextromethorphan, or 2) a combination of an antidepressant compound and dextromethorphan to a human being in need thereof, wherein the human being is an extensive metabolizer of dextromethorphan.

Some embodiments include a method of increasing dextromethorphan plasma levels in a human being in need of treatment with dextromethorphan, wherein the human being is an extensive metabolizer of dextromethorphan, comprising co-administering bupropion with dextromethorphan to the human being.

Some embodiments include a method of inhibiting the metabolism of dextromethorphan, comprising administering bupropion to a human being, wherein the human being is an extensive metabolizer of dextromethorphan, and wherein dextromethorphan is present in the body of the human being at the same time as bupropion.

Some embodiments include a method of increasing the metabolic lifetime of dextromethorphan, comprising administering bupropion to a human being in need of treatment with dextromethorphan, wherein the human being is an extensive metabolizer of dextromethorphan, and wherein dextromethorphan is present in the body of the human being at the same time as bupropion.

Some embodiments include a method of correcting extensive metabolism of dextromethorphan, comprising administering bupropion to a human being in need thereof.

Some embodiments include a method of improving the antitussive properties of dextromethorphan comprising administering bupropion in conjunction with administration of dextromethorphan to a human being in need of treatment for cough.

Some embodiments include a method of treating cough comprising administering a combination of bupropion or another active compound and dextromethorphan to a human being in need thereof.

Some embodiments include a method of treating a neurological disorder comprising administering 1) dextromethorphan, or 2) bupropion and dextromethorphan to a human being in need thereof, wherein the 1) dextromethorphan, or 2) bupropion and dextromethorphan are administered at least once a day for at least 8 days, at least 9 days, or at least 10 days.

Some embodiments include a method of treating a neurological disorder comprising administering about 150 mg/day to about 300 mg/day of bupropion and about 15 mg/day to about 60 mg/day of dextromethorphan to a human being in need thereof.

Some embodiments include a method of increasing dextromethorphan plasma levels in a human being in need of treatment with dextromethorphan, wherein the human being is an extensive metabolizer of dextromethorphan, comprising co-administering hydroxybupropion, or a prodrug thereof, with dextromethorphan to the human being.

Some embodiments include a method of increasing dextromethorphan plasma levels in a human being in need of treatment with dextromethorphan, wherein the human being is an extensive metabolizer of dextromethorphan, comprising co-administering erythrohydroxybupropion, or a prodrug thereof, with dextromethorphan to the human being.

Some embodiments include a method of increasing dextromethorphan plasma levels in a human being in need of treatment with dextromethorphan, wherein the human being is an extensive metabolizer of dextromethorphan, comprising co-administering threohydroxybupropion, or a prodrug thereof, with dextromethorphan to the human being.

Some embodiments include a method of inhibiting metabolism of dextromethorphan, comprising administering bupropion to a human being, wherein the human being is an extensive metabolizer of dextromethorphan, and wherein dextromethorphan is present in the body of the human being at the same time as bupropion.

Some embodiments include a method of inhibiting metabolism of dextromethorphan, comprising administering hydroxybupropion, or a prodrug thereof, to a human being, wherein the human being is an extensive metabolizer of dextromethorphan, and wherein dextromethorphan is present in the body of the human being at the same time as hydroxybupropion.

Some embodiments include a method of inhibiting metabolism of dextromethorphan, comprising administering erythrohydroxybupropion, or a prodrug thereof, to a human being, wherein the human being is an extensive metabolizer of dextromethorphan, and wherein dextromethorphan is present in the body of the human being at the same time as erythrohydroxybupropion.

Some embodiments include a method of inhibiting metabolism of dextromethorphan, comprising administering threohydroxybupropion, or a prodrug thereof, to a human being, wherein the human being is an extensive metabolizer of dextromethorphan, and wherein dextromethorphan is present in the body of the human being at the same time as threohydroxybupropion.

Some embodiments include a method of increasing the metabolic lifetime of dextromethorphan, comprising administering hydroxybupropion, or a prodrug thereof, to a human being in need of treatment with dextromethorphan, wherein the human being is an extensive metabolizer of dextromethorphan, and wherein dextromethorphan is present in the body of the human being at the same time as hydroxybupropion.

Some embodiments include a method of increasing the metabolic lifetime of dextromethorphan, comprising administering erythrohydroxybupropion, or a prodrug thereof, to a human being in need of treatment with dextromethorphan, wherein the human being is an extensive metabolizer of dextromethorphan, and wherein dextromethorphan is present in the body of the human being at the same time as erythrohydroxybupropion.

Some embodiments include a method of increasing dextromethorphan plasma levels comprising co-administering bupropion and dextromethorphan to a human being in need of treatment with dextromethorphan, wherein the bupropion is administered on the first day of at least two days of co-administration of bupropion with dextromethorphan, wherein an increase in the dextromethorphan plasma level occurs on the first day that bupropion and dextromethorphan are co-administered, as compared to the same amount of dextromethorphan administered without bupropion.

Some embodiments include a method of increasing dextromethorphan plasma levels comprising co-administering hydroxybupropion, or a prodrug thereof, and dextromethorphan to a human being in need of treatment with dextromethorphan, wherein the hydroxybupropion, or a prodrug thereof, is administered on the first day of at least two days of co-administration of hydroxybupropion, or a prodrug thereof, with dextromethorphan, wherein an increase in the dextromethorphan plasma level occurs on the first day that hydroxybupropion, or a prodrug thereof, and dextromethorphan are co-administered, as compared to the same amount of dextromethorphan administered without hydroxybupropion or a prodrug thereof.

Some embodiments include a method of increasing dextromethorphan plasma levels comprising co-administering erythrohydroxybupropion, or a prodrug thereof, and dextromethorphan to a human being in need of treatment with dextromethorphan, wherein the erythrohydroxybupropion, or a prodrug thereof, is administered on the first day of at least two days of co-administration of erythrohydroxybupropion, or a prodrug thereof, with dextromethorphan, wherein an increase in the dextromethorphan plasma level occurs on the first day that erythrohydroxybupropion, or a prodrug thereof, and dextromethorphan are co-administered, as compared to the same amount of dextromethorphan administered without erythrohydroxybupropion or a prodrug thereof.

Some embodiments include a method of increasing dextromethorphan plasma levels comprising co-administering threohydroxybupropion, or a prodrug thereof, and dextromethorphan to a human being in need of treatment with dextromethorphan, wherein the threohydroxybupropion, or a prodrug thereof, is administered on the first day of at least two days of co-administration of threohydroxybupropion, or a prodrug thereof, with dextromethorphan, wherein an increase in the dextromethorphan plasma level occurs on the first day that threohydroxybupropion, or a prodrug thereof, and dextromethorphan are co-administered, as compared to the same amount of dextromethorphan administered without threohydroxybupropion or a prodrug thereof.

Some embodiments include a method of increasing dextromethorphan plasma levels comprising co-administering bupropion and dextromethorphan, for at least five consecutive days, to a human being in need of treatment with dextromethorphan, wherein, on the fifth day, the dextromethorphan plasma level is higher than the dextromethorphan plasma level that would have been achieved by administering the same amount of dextromethorphan administered without bupropion for five consecutive days.

Some embodiments include a method of increasing dextromethorphan plasma levels comprising co-administering hydroxybupropion, or a prodrug thereof, and dextromethorphan, for at least five consecutive days, to a human being in need of treatment with dextromethorphan, wherein, on the fifth day, the dextromethorphan plasma level is higher than the dextromethorphan plasma level that would have been achieved by administering the same amount of dextromethorphan administered without hydroxybupropion, or a prodrug thereof, for five consecutive days.

Some embodiments include a method of increasing dextromethorphan plasma levels comprising co-administering erythrohydroxybupropion, or a prodrug thereof, and dextromethorphan, for at least five consecutive days, to a human being in need of treatment with dextromethorphan, wherein, on the fifth day, the dextromethorphan plasma level is higher than the dextromethorphan plasma level that would have been achieved by administering the same amount of dextromethorphan administered without erythrohydroxybupropion, or a prodrug thereof, for five consecutive days.

Some embodiments include a method of increasing dextromethorphan plasma levels comprising co-administering threohydroxybupropion, or a prodrug thereof, and dextromethorphan, for at least five consecutive days, to a human being in need of treatment with dextromethorphan, wherein, on the fifth day, the dextromethorphan plasma level is higher than the dextromethorphan plasma level that would have been achieved by administering the same amount of dextromethorphan administered without threohydroxybupropion, or a prodrug thereof, for five consecutive days.

Some embodiments include a method of increasing dextromethorphan plasma levels comprising co-administering bupropion and dextromethorphan, for at least six consecutive days, to a human being in need of treatment with dextromethorphan, wherein, on the sixth day, the dextromethorphan plasma level is higher than the dextromethorphan plasma level that would have been achieved by administering the same amount of dextromethorphan administered without bupropion for six consecutive days.

Some embodiments include a method of increasing dextromethorphan plasma levels comprising co-administering hydroxybupropion, or a prodrug thereof, and dextromethorphan, for at least six consecutive days, to a human being in need of treatment with dextromethorphan, wherein, on the sixth day, the dextromethorphan plasma level is higher than the dextromethorphan plasma level that would have been achieved by administering the same amount of dextromethorphan administered without hydroxybupropion, or a prodrug thereof, for six consecutive days.

Some embodiments include a method of increasing dextromethorphan plasma levels comprising co-administering erythrohydroxybupropion, or a prodrug thereof, and dextromethorphan, for at least six consecutive days, to a human being in need of treatment with dextromethorphan, wherein, on the sixth day, the dextromethorphan plasma level is higher than the dextromethorphan plasma level that would have been achieved by administering the same amount of dextromethorphan administered without erythrohydroxybupropion, or a prodrug thereof, for six consecutive days.

Some embodiments include a method of increasing dextromethorphan plasma levels comprising co-administering threohydroxybupropion, or a prodrug thereof, and dextromethorphan, for at least six consecutive days, to a human being in need of treatment with dextromethorphan, wherein, on the sixth day, the dextromethorphan plasma level is higher than the dextromethorphan plasma level that would have been achieved by administering the same amount of dextromethorphan administered without threohydroxybupropion, or a prodrug thereof, for six consecutive days.

Some embodiments include a method of reducing a trough effect of dextromethorphan comprising, co-administering bupropion with dextromethorphan to a human patient in need of treatment with dextromethorphan, wherein dextromethorphan has a plasma level 12 hours after co-administering bupropion with dextromethorphan that is at least twice the plasma level that would be achieved by administering the same amount of dextromethorphan without bupropion.

Some embodiments include a method of reducing a trough effect of dextromethorphan comprising, co-administering hydroxybupropion, or a prodrug thereof, with dextromethorphan to a human patient in need of treatment with dextromethorphan, wherein dextromethorphan has a plasma level 12 hours after co-administering hydroxybupropion, or a prodrug thereof, with dextromethorphan that is at least twice the plasma level that would be achieved by administering the same amount of dextromethorphan without hydroxybupropion or a prodrug thereof.

Some embodiments include a method of reducing a trough effect of dextromethorphan comprising, co-administering erythrohydroxybupropion, or a prodrug thereof, with dextromethorphan to a human patient in need of treatment with dextromethorphan, wherein dextromethorphan has a plasma level 12 hours after co-administering erythrohydroxybupropion, or a prodrug thereof, with dextromethorphan that is at least twice the plasma level that would be achieved by administering the same amount of dextromethorphan without erythrohydroxybupropion or a prodrug thereof.

Some embodiments include a method of reducing a trough effect of dextromethorphan comprising, co-administering threohydroxybupropion, or a prodrug thereof, with dextromethorphan to a human patient in need of treatment with dextromethorphan, wherein dextromethorphan has a plasma level 12 hours after co-administering threohydroxybupropion, or a prodrug thereof, with dextromethorphan that is at least twice the plasma level that would be achieved by administering the same amount of dextromethorphan without threohydroxybupropion or a prodrug thereof.

Some embodiments include a method of reducing an adverse event associated with treatment by dextromethorphan, comprising co-administering bupropion and dextromethorphan to a human patient in need of dextromethorphan treatment, wherein the human patient is at risk of experiencing the adverse event as a result of being treated with dextromethorphan.

Some embodiments include a method of reducing an adverse event associated with treatment by dextromethorphan, comprising co-administering hydroxybupropion, or a prodrug thereof, and dextromethorphan to a human patient in need of dextromethorphan treatment, wherein the human patient is at risk of experiencing the adverse event as a result of being treated with dextromethorphan.

Some embodiments include a method of reducing an adverse event associated with treatment by dextromethorphan, comprising co-administering erythrohydroxybupropion, or a prodrug thereof, and dextromethorphan to a human patient in need of dextromethorphan treatment, wherein the human patient is at risk of experiencing the adverse event as a result of being treated with dextromethorphan.

Some embodiments include a method of reducing an adverse event associated with treatment by bupropion, comprising co-administering dextromethorphan and bupropion to a human patient in need of bupropion treatment, wherein the human patient is at risk of experiencing the adverse event as a result of being treated with bupropion.

Some embodiments include a method of correcting extensive metabolism of dextromethorphan, comprising administering hydroxybupropion, or a prodrug thereof, to a human being in need thereof.

Some embodiments include a method of correcting extensive metabolism of dextromethorphan, comprising administering erythrohydroxybupropion, or a prodrug thereof, to a human being in need thereof.

Some embodiments include a method of correcting extensive metabolism of dextromethorphan, comprising administering threohydroxybupropion, or a prodrug thereof, to a human being in need thereof.

Some embodiments include a method of improving antitussive properties of dextromethorphan comprising administering bupropion in conjunction with administration of dextromethorphan to a human being in need of treatment for cough.

Some embodiments include a method of improving antitussive properties of dextromethorphan comprising administering hydroxybupropion, or a prodrug thereof, in conjunction with administration of dextromethorphan to a human being in need of treatment for cough.

Some embodiments include a method of improving antitussive properties of dextromethorphan comprising administering erythrohydroxybupropion, or a prodrug thereof, in conjunction with administration of dextromethorphan to a human being in need of treatment for cough.

Some embodiments include a method of improving antitussive properties of dextromethorphan comprising administering threohydroxybupropion, or a prodrug thereof, in conjunction with administration of dextromethorphan to a human being in need of treatment for cough.

Some embodiments include a method of treating cough comprising administering a combination of hydroxybupropion, or a prodrug thereof, and dextromethorphan to a human being in need thereof.

Some embodiments include a method of treating cough comprising administering a combination of erythrohydroxybupropion, or a prodrug thereof, and dextromethorphan to a human being in need thereof.

Some embodiments include a method of treating cough comprising administering a combination of threohydroxybupropion, or a prodrug thereof, and dextromethorphan to a human being in need thereof.

Some embodiments include a method of treating a neurological disorder comprising administering bupropion and dextromethorphan to a human being in need thereof, wherein the bupropion and dextromethorphan are administered at least once a day for at least 8 days, at least 9 days, or at least 10 days.

Some embodiments include a method of treating a neurological disorder comprising administering hydroxybupropion, or a prodrug thereof, and dextromethorphan to a human being in need thereof, wherein the bupropion and dextromethorphan are administered at least once a day for at least 8 days, at least 9 days, or at least 10 days.

Some embodiments include a method of treating a neurological disorder comprising administering erythrohydroxybupropion, or a prodrug thereof, and dextromethorphan to a human being in need thereof, wherein the erythrohydroxybupropion and dextromethorphan are administered at least once a day for at least 8 days, at least 9 days, or at least 10 days.

Some embodiments include a method of treating a neurological disorder comprising administering threohydroxybupropion, or a prodrug thereof, and dextromethorphan to a human being in need thereof, wherein the threohydroxybupropion and dextromethorphan are administered at least once a day for at least 8 days, at least 9 days, or at least 10 days.

Some embodiments include a pharmaceutical composition, dosage form, or medicament comprising a therapeutically effective amount of dextromethorphan, a therapeutically effective amount of an antidepressant, such as bupropion, hydroxybupropion, erythrohydroxybupropion, threohydroxybupropion, or a metabolite or prodrug of any of these compounds, and a pharmaceutically acceptable excipient.

DETAILED DESCRIPTION

Figure 1:
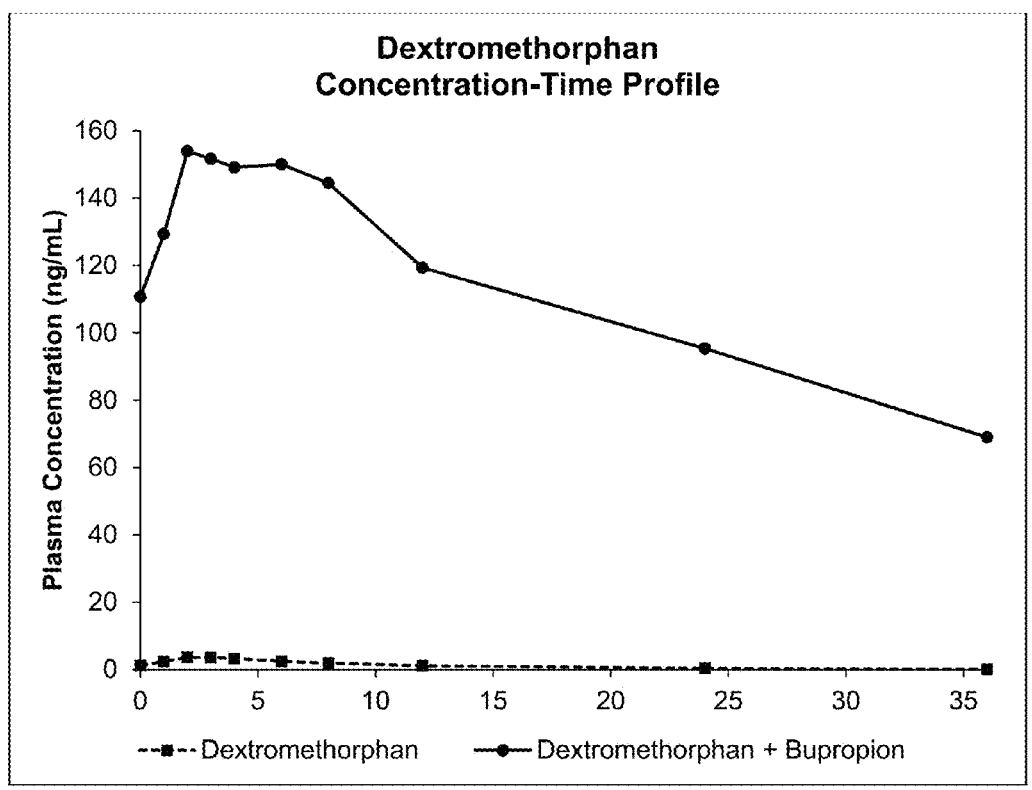
FIG. 1 is a plot of the mean plasma concentrations of dextromethorphan over time after dosing on Day 8 for subjects administered dextromethorphan alone or dextromethorphan and bupropion.

Some embodiments include a method of treating neurological disorders comprising administering a therapeutically effective amount of dextromethorphan and a therapeutically effective amount of an antidepressant, such as bupropion, hydroxybupropion, erythrohydroxybupropion, threohydroxybupropion, or a metabolite or prodrug of any of these compounds, to a person in need thereof.

Some embodiments include a method of enhancing the therapeutic properties of dextromethorphan in treating neurological disorders, comprising co-administering dextromethorphan and an antidepressant, such as bupropion, hydroxybupropion, erythrohydroxybupropion, threohydroxybupropion, or a metabolite or prodrug of any of these compounds.

Some embodiments include a method of increasing dextromethorphan plasma levels in a human being that is an extensive metabolizer of dextromethorphan, comprising co-administering an antidepressant compound, such as bupropion, and dextromethorphan to the human being.

Some embodiments include a method of inhibiting the metabolism of dextromethorphan, comprising administering an antidepressant compound, such as bupropion, to a human being, wherein the human being is an extensive metabolizer of dextromethorphan, and wherein dextromethorphan is present in the body of the human being at the same time as the antidepressant.

Some embodiments include a method of increasing the metabolic lifetime of dextromethorphan, including increasing the elimination half life ($T_{1/2}$) of dextromethorphan. These embodiments may comprise administering an antidepressant compound, such as bupropion, to a human being, wherein the human being is an extensive metabolizer of dextromethorphan, and wherein dextromethorphan is present in the body of the human being at the same time as the antidepressant compound.

Some embodiments include a method of correcting extensive metabolism of dextromethorphan, comprising administering an antidepressant compound, such as bupropion, to a human being in need thereof, such as a human being in need of treatment for pain.

Some embodiments include a method of improving the therapeutic properties of dextromethorphan in treating neurological disorders comprising administering an antidepressant compound, such as bupropion, in conjunction with administration of dextromethorphan to a human being in need of treatment for a neurological disorder.

Some embodiments include a method of treating neurological disorders comprising administering a combination of an antidepressant compound, such as bupropion, and dextromethorphan to a human being in need thereof.

Co-administration of an antidepressant compound, such as bupropion, hydroxybupropion, threohydroxybupropion, erythrohydroxybupropion, or a prodrug of the antidepressant compound, with dextromethorphan may occur one or more times for a single day, or for 2, 3, 4, 5, 6, 7, 8, 14, 30, 60, 90, or more consecutive days. In some embodiments, co-administration is at least daily for at least two consecutive days.

Dextromethorphan has the structure shown below.

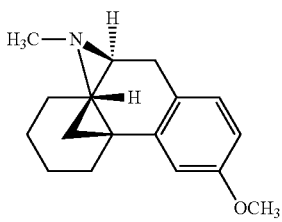

Dextromethorphan is used as a cough suppressant. According to the FDA's dextromethorphan product labeling requirement under the OTC Monograph [21CFR341.74], dextromethorphan should be dosed 6 times a day (every 4 hours), 4 times a day (every 6 hours), or 3 times a day (every 8 hours).

Dextromethorphan is rapidly metabolized in the human liver. This rapid hepatic metabolism may limit systemic drug exposure in individuals who are extensive metabolizers. Human beings can be: 1) extensive metabolizers of dextromethorphan—those who rapidly metabolize dextromethorphan; 2) poor metabolizers of dextromethorphan—those who only poorly metabolize dextromethorphan; or 3) intermediate metabolizers of dextromethorphan—those whose metabolism of dextromethorphan is somewhere between that of an extensive metabolizer and a poor metabolizer. Extensive metabolizers can also be ultra-rapid metabolizers. Extensive metabolizers of dextromethorphan are a significant portion of the human population. Dextromethorphan can, for example, be metabolized to dextrorphan.

When given the same oral dose of dextromethorphan, plasma levels of dextromethorphan are significantly higher in poor metabolizers or intermediate metabolizers as compared to extensive metabolizers of dextromethorphan. The low plasma concentrations of dextromethorphan can limit its clinical utility as a single agent for extensive metabolizers, and possibly intermediate metabolizers, of dextromethorphan. Some therapeutically active compounds, including antidepressants such as bupropion, inhibit the metabolism of dextromethorphan, and raise the plasma concentration of dextromethorphan, and can thus improve its therapeutic efficacy. Similarly, antidepressants may allow dextromethorphan to be given less often, such as once a day instead of twice a day, once a day instead of three times a day, once a day instead of four times a day, twice a day instead of three times a day, or twice a day instead of four times a day, without loss of therapeutic efficacy.

Co-administration of an antidepressant such as bupropion, hydroxybupropion, erythrohydroxybupropion, threohydroxybupropion, or a metabolite or prodrug of any of these compounds, with dextromethorphan or dextrorphan may enhance the mechanisms of action, or pharmacological properties of dextromethorphan and dextrorphan. Mechanisms of action of dextromethorphan and dextrorphan can include sigma-1 agonist and NMDA antagonist properties, calcium channel blockade, muscarinic binding, serotonin transporter (5HTT) inhibition, and mu receptor potentiation.

Some embodiments include co-administration of an antidepressant such as bupropion, hydroxybupropion, erythrohydroxybupropion, threohydroxybupropion, or a metabolite or prodrug of any of these compounds, with dextromethorphan or dextrorphan to agonize, antagonize, or modulate a sigma-1 receptor, or an NMDA receptor; to block a calcium channel; to bind to a muscarinic receptor; to inhibit a serotonin transporter (5HTT); or to potentiate a mu receptor.

Pharmacological properties of dextromethorphan and dextrorphan can include NMDA high-affinity site, NMDR-2A, and functional NMDR-2B receptor antagonism, sigma-1 stimulation, putative mTOR activation (by sigma-1 stimulation, mu potentiation, beta adrenoreceptor stimulation, and 5HTT inhibition), putative AMPA receptor trafficking (by mTOR activation, PCP antagonism, sigma-1 stimulation, beta stimulation, mu potentiation, and 5HTT inhibition), and dendritogenesis, spinogenesis, synaptogenesis, and neuronal survival by NMDA antagonism and sigma-1 and mTOR signaling. Some embodiments include co-administration of an antidepressant such as bupropion, hydroxybupropion, erythrohydroxybupropion, threohydroxybupropion, or a metabolite or prodrug of any of these compounds, with dextromethorphan or dextrorphan to bind to, agonize, antagonize, stimulate, activate, inhibit, influence the trafficking of, or modulate an NMDA high-affinity site, NMDR-2A, a functional NMDR-2B receptor, sigma-1 receptor, a putative mTOR receptor (such as by stimulating sigma-1, potentiating a mu receptor, stimulating a beta adrenoreceptor, or inhibiting a 5HTT), or a putative AMPA receptor (such as by activating mTOR, antagonizing PCP activity, stimulating a sigma-1 receptor, stimulating a beta adrenergic receptor, potentiating a mu receptor, or inhibiting 5HTT). Some embodiments include co-administration of an antidepressant such as bupropion, hydroxybupropion, erythrohydroxybupropion, threohydroxybupropion, or a metabolite or prodrug of any of these compounds, with dextromethorphan or dextrorphan to cause, increase, decrease, or otherwise modulate dendritogenesis, spinogenesis, or synaptogenesis. Some embodiments include co-administration of an antidepressant such as bupropion, hydroxybupropion, erythrohydroxybupropion, threohydroxybupropion, or a metabolite or prodrug of any of these compounds, with dextromethorphan or dextrorphan to cause, increase, decrease, or otherwise modulate neuronal survival by NMDA antagonism and/or sigma-1 and/or mTOR signaling.

Pharmacological properties of dextromethorphan and dextrorphan can include 5HTT and norepinephrine transporter inhibition, sigma-1 stimulation, NMDA and PCP antagonism, and possible serotonin 5HT1b/d receptor stimulation. Some embodiments include co-administration of an antidepressant such as bupropion, hydroxybupropion, erythrohydroxybupropion, threohydroxybupropion, or a metabolite or prodrug of any of these compounds, with dextromethorphan or dextrorphan to bind to, agonize, antagonize, stimulate, activate, inhibit, influence the trafficking of, or modulate the 5HTT and/or norepinephrine transporter, the sigma-1 receptor, NMDA and/or PCP receptor, and/or to stimulate the serotonin 5HT1b/d receptor.

Additional properties for dextromethorphan and dextrorphan can include possible presynaptic alpha-2 adrenoreceptor antagonism or postsynaptic alpha-2 stimulation, beta stimulation and possible muscarinic and mu antagonism. Some embodiments include co-administration of an antidepressant such as bupropion, hydroxybupropion, erythrohydroxybupropion, threohydroxybupropion, or a metabolite or prodrug of any of these compounds, with dextromethorphan or dextrorphan to bind to, agonize, antagonize, stimulate, activate, inhibit, influence the trafficking of, or modulate a presynaptic alpha-2 adrenoreceptor, postsynaptic alpha-2 receptor, beta adrenoreceptor, muscarinic receptor, or mu receptor. Dextromethorphan and dextrorphan may be glial cell modulators. Some embodiments include co-administration of an antidepressant such as bupropion, hydroxybupropion, erythrohydroxybupropion, threohydroxybupropion, or a metabolite or prodrug of any of these compounds, with dextromethorphan or dextrorphan to modulate glial cells.

Pain or other neurological disorders may be treated by enhancing dextromethorphan plasma levels or increasing dextromethorphan bioavailability, for example by a method comprising administering a therapeutically effective amount of dextromethorphan and a therapeutically effective amount of an antidepressant compound, such as bupropion, hydroxybupropion, erythrohydroxybupropion, threohydroxybupropion, or a metabolite or prodrug of any of these compounds, to a person in need thereof.

Examples of neurological disorders that may be treated, or that may be treated with increased efficacy, enhanced dextromethorphan levels, such as those achievable by a combination of dextromethorphan and an antidepressant such as bupropion, hydroxybupropion, erythrohydroxybupropion, threohydroxybupropion, or a metabolite or prodrug of any of these compounds, include, but are not limited to: affective disorders, psychiatric disorders, cerebral function disorders, movement disorders, dementias, motor neuron diseases, neurodegenerative diseases, seizure disorders, and headaches.

Affective disorders that may be treated by enhanced dextromethorphan levels or by a combination of dextromethorphan and an antidepressant such as bupropion, hydroxybupropion, erythrohydroxybupropion, threohydroxybupropion, or a metabolite or prodrug of any of these compounds, include, but are not limited to, depression, major depression, treatment resistant depression and treatment resistant bipolar depression, bipolar disorders including cyclothymia, seasonal affective disorder, mood disorders, chronic depression (dysthymia), psychotic depression, postpartum depression, premenstrual dysphoric disorder (PMDD), situational depression, atypical depression, mania, anxiety disorders, attention deficit disorder (ADD), attention deficit disorder with hyperactivity (ADDH), and attention deficit/hyperactivity disorder (AD/HD), bipolar and manic conditions, obsessive-compulsive disorder, bulimia, obesity or weight-gain, narcolepsy, chronic fatigue syndrome, premenstrual syndrome, substance addiction or abuse, nicotine addiction, psycho-sexual dysfunction, pseudobulbar affect, and and emotional lability.

Depression may be manifested by depressive symptoms. These symptoms may include psychological changes such as changes in mood, feelings of intense sadness, despair, mental slowing, loss of concentration, pessimistic worry, agitation, anxiety, irritability, guilt, anger, feelings of worthlessness, reckless behavior, suicidal thoughts or attempts, and/or self-deprecation. Physical symptoms of depression may include insomnia, anorexia, appetite loss, weight loss, weight gain, decreased energy and libido, fatigue, restlessness, aches, pains, headaches, cramps, digestive issues, and/or abnormal hormonal circadian rhythms.

Some patients, even after treatment with medications such as antidepressants, may have an inadequate or no response to the treatment. Treatment resistant depression (TRD), or treatment-refractory depression, is a condition generally associated with patients who have failed treatment with at least two antidepressants. Part of the diagnosis for TRD is for the patient to have had an inadequate response to treatment with the antidepressants after an adequate dose and adequate course. TRD may be more difficult to treat due to the comorbidity of other medical or psychological illnesses, such as drug/alcohol abuse or eating disorders, or TRD being misdiagnosed. Some TRD patients have had an inadequate response to 1, 2, 3, or more adequate antidepressant treatment trials or have failed or had an inadequate response to 1, 2, 3, or more prior antidepressant treatments. In some embodiments, a patient being treated for treatment resistant depression has failed treatment with at least 1, 2, 3, 4, 5, 6, 7, 8, 9, 10, or more antidepressant therapies.

Measures of treatment effect that may be improved by treatment with enhanced bioavailability or plasma levels of dextromethorphan, or by a combination of dextromethorphan and an antidepressant, such as bupropion, hydroxybupropion, erythrohydroxybupropion, threohydroxybupropion, or a metabolite or prodrug of any of these compounds, include, but are not limited to: Montgomery-Asberg Depression Rating Scale (MADRS), Quality of Life Enjoyment and Satisfaction Questionnaire Short Form, Range of Impaired Functioning Tool, Sheehan Disability Scale, Patient Rated Inventory of Side Effects (PRISE), Columbia-Suicide Severity Rating Scale (C-SSRS), Quick Inventory of Depressive Symptomatology, Self Report (QIDS-SR), Clinical Global Impression (CGI) scale, Massachusetts General Hospital Cognitive and Physical Functioning Questionnaire (CPFQ), 17-item Hamilton Rating Scale for Depression (HAM-D17), Massachusetts General Hospital Antidepressant Treatment Response Questionnaire (MGH ATRQ), 16-item Quick Inventory of Depressive Symptomatology-Self Report (QIDS-SR16), Sheehan Disability Scale (SDS), Clinical Global Impression of Severity of Illness (CGI-S), Clinical Global Impression of Change (CGI-C), EuroQOL 5 Dimension 5 Level (EQ-5D-5L), Patient Global Impression of Change (PGIC), 7-item Generalized Anxiety Disorder (GAD-7), Clinical Global Impressions-Improvement (CGI-I). Sheehan Disability Scale (SDS). 16-item Quick Inventory of Depressive Symptomatology-Self Report (QIDS-SR16), Hamilton Anxiety Scale (HAM-A), Massachusetts General Hospital Cognitive and Physical Functioning Questionnaire (CPFQ), CPFQ-Cognitive subscales (Items 4 to 7), Brief Psychiatric Rating Scale (BPRS), etc.; Digit Symbol Substitution Test (DSST), Rey Auditory Verbal Learning Task (RAVLT), Trail Making Test (TMT), Stroop Colour Naming Test (STROOP), Simple Reaction Time (SRT), Choice Reaction Time (CRT). etc.

In some embodiments, an enhanced bioavailability of dextromethorphan, or a combination of dextromethorphan and an antidepressant such as bupropion, hydroxybupropion, erythrohydroxybupropion, threohydroxybupropion, or a metabolite or prodrug of any of these compounds, may have an onset of action within 30 minutes, 1 hour, 2 hours, 3 hours, 4 hours, 5 hours, 6 hours, 6-8 hours, 8-12 hours, 12 hours, a day, 1-7 days, 1 week, two weeks, three weeks, four weeks, six weeks, or eight weeks.

Patients who may benefit from the treatments described herein include pediatric patients, such as patients under about 18 years of age, about 0-5 years of age, about 5-10 years of age, about 10-12 years of age, or about 12-18 years of age; adult patients, such as patients having an age of about 18-65 years, about 18-30 years, about 30-50 years, about 50-65 years; and elderly patients, such as patients over 65 years of age, about 65-75 years of age, about 75-90 years of age, or over 90 years of age.

In some embodiments, an enhanced bioavailability of dextromethorphan, or a combination of dextromethorphan and an antidepressant such as bupropion, hydroxybupropion, erythrohydroxybupropion, threohydroxybupropion, or a metabolite or prodrug of any of these compounds, may be used as an adjunctive therapy for treatment of any condition recited herein, including TRD. For example, the adjunctive therapy could be used in combination with another antidepressant, such as bupropion, hydroxybupropion, erythrohydroxybupropion, threohydroxybupropion, clomipramine, doxepin, fluoxetine, mianserin, imipramine, 2-chloroimipramine, amitriptyline, amoxapine, desipramine, protriptyline, trimipramine, nortriptyline, maprotiline, phenelzine, isocarboxazid, tranylcypromine, paroxetine, trazodone, citalopram, sertraline, aryloxy indanamine, benactyzine, escitalopram, fluvoxamine, venlafaxine, desvenlafaxine, duloxetine, mirtazapine, nefazodone, selegiline, sibutramine, milnacipran, tesofensine, brasofensine, moclobemide, rasagiline, nialamide, iproniazid, iproclozide, toloxatone, butriptyline, dosulepin, dibenzepin, iprindole, lofepramine, opipramol, norfluoxetine, dapoxetine, ketamine, etc., or a metabolite or prodrug of any of these compounds, or a pharmaceutically acceptable salt of any of these compounds.

In some embodiments, TRD may be treated by enhanced bioavailability or plasma levels of dextromethorphan, or by a combination of dextromethorphan and an antidepressant such as bupropion, hydroxybupropion, erythrohydroxybupropion, threohydroxybupropion, or a metabolite or prodrug of any of these compounds and may result in a reduction of depressive symptoms of at least about 5%, at least about 10%, at least about 20%, at least about 30%, at least about 40%, at least about 50%, at least about 60%, at least about 70%, at least about 80%, at least about 90%, up to about 100%, or any other reduction in a range bounded by any of these values.

Psychiatric disorders that may be treated enhanced plasma levels of dextromethorphan such as those achieved by a combination of dextromethorphan and an antidepressant such as bupropion, hydroxybupropion, erythrohydroxybupropion, threohydroxybupropion, or a metabolite or prodrug of any of these compounds, include, but are not limited to, anxiety disorders, including but not limited to, phobias, generalized anxiety disorder, social anxiety disorder, panic disorder, agoraphobia, obsessive-compulsive disorder, and post-traumatic stress disorder (PTSD); mania, manic depressive illness, hypomania, unipolar depression, depression, stress disorders, somatoform disorders, personality disorders, psychosis, schizophrenia, delusional disorder, schizoaffective disorder, schizotypy, aggression, aggression in Alzheimer's disease, agitation, and agitation in Alzheimer's disease.

Agitation in Alzheimer's disease occurs as the disease progresses. Agitation may present itself as inappropriate verbal, emotional, and/or physical behaviors. Inappropriate behaviors may include, but is not limited to, incoherent babbling, inappropriate emotional response, demands for attention, threats, irritability, frustration, screaming, repetitive questions, mood swings, cursing, abusive language, physical outbursts, emotional distress, restlessness, shredding, sleeping disturbances, delusions, hallucinations, pacing, wandering, searching, rummaging, repetitive body motions, hoarding, shadowing, hitting, scratching, biting, combativeness, hyperactivity, and/or kicking.

In some embodiments, agitation in Alzheimer's disease may be treated by enhanced plasma levels of dextromethorphan or by a combination of dextromethorphan and an antidepressant such as bupropion, hydroxybupropion, erythrohydroxybupropion, threohydroxybupropion, or a metabolite or prodrug of any of these compounds and may result in a reduction of agitation-related symptoms of at least about 5%, at least about 10%, at least about 20%, at least about 30%, at least about 40%, at least about 50%, at least about 60%, at least about 70%, at least about 80%, at least about 90%, up to about 100%, or any other reduction in a range bounded by any of these values.

Measures of treatment effect that may be improved by treatment with enhanced bioavailability or plasma levels of dextromethorphan, or by a combination of dextromethorphan and an antidepressant such as bupropion, hydroxybupropion, erythrohydroxybupropion, threohydroxybupropion, or a metabolite or prodrug of any of these compounds include, but are not limited to, Neuropsychiatric Inventory-Clinician (NPI-C) rating scale, overall and all domains; Neuropsychiatric Inventory-Clinician (NPI-C) rating scale Agitation domain; Cohen-Mansfield Agitation Inventory (CMAI); Cornell Scale for Depression in Dementia (CSDD); Neuropsychiatric Inventory (NPI Agitation/Aggression Domain); Cocomitant Medications (Frequency of using concomitant medications); Alzheimer's Disease Cooperative Study-Activities of Daily Living Inventory (ADCS-ADL); Neuropsychiatric Inventory (NPI) Individual Domains and NPI Total Scores (range 0-144), including NPI-C Apathy domain, NPI Agitation/Aggression Caregiver Distress, Modified Alzheimer's Disease Cooperative Study-Clinical Global Impression of Change Agitation (mADCS-CGIC Agitation), Patient Global Impression of Change (PGIC) (rated by caregiver), Dementia Quality of Life (DEMQOL), Quality of Life-Alzheimer's disease measure (QoL-AD), Zarit Burden Scale, Resource Utilization in Dementia (RUD), Alzheimer's Disease Assessment Scale-Cognitive Subscale (ADAS-Cog), Mini-mental State Examination (MMSE), Caregiver Strain Index (CSI), Individual Domain of the Neuropsychiatric Inventory (NPI), Total Neuropsychiatric Inventory (NPI) Score, Neuropsychiatric Inventory (Agitation/Aggression Domain of NPI), Neuropsychiatric Inventory (Caregiver Distress for NPI Domains), etc.

Substance addiction abuse that may be treated by enhanced bioavailability or plasma levels of dextromethorphan or by a combination of dextromethorphan and an antidepressant such as bupropion, hydroxybupropion, erythrohydroxybupropion, threohydroxybupropion, or a metabolite or prodrug of any of these compounds, includes, but is not limited to, drug dependence, addiction to cocaine, psychostimulants (e.g., crack, cocaine, speed, meth), nicotine, alcohol, opioids, anxiolytic and hypnotic drugs, cannabis (marijuana), amphetamines, hallucinogens, phencyclidine, volatile solvents, and volatile nitrites. Nicotine addiction includes nicotine addiction of all known forms, such as smoking cigarettes, cigars and/or pipes, and addiction to chewing tobacco.

Cerebral function disorders that may be treated by enhanced bioavailability or plasma levels of dextromethorphan, or by a combination of dextromethorphan and an antidepressant such as bupropion, hydroxybupropion, erythrohydroxybupropion, threohydroxybupropion, or a metabolite or prodrug of any of these compounds include, but are not limited to, disorders involving intellectual deficits such as senile dementia, Alzheimer's type dementia, memory loss, amnesia/amnestic syndrome, epilepsy, disturbances of consciousness, coma, lowering of attention, speech disorders, voice spasms, Parkinson's disease, Lennox-Gastaut syndrome, autism, hyperkinetic syndrome, and schizophrenia. Cerebral function disorders also include disorders caused by cerebrovascular diseases including, but not limited to, stroke, cerebral infarction, cerebral bleeding, cerebral arteriosclerosis, cerebral venous thrombosis, head injuries, and the like where symptoms include disturbance of consciousness, senile dementia, coma, lowering of attention, and speech disorders.

Movement disorders that may be treated by enhanced bioavailability or plasma levels of dextromethorphan, or by a combination of dextromethorphan and an antidepressant such as bupropion, hydroxybupropion, erythrohydroxybupropion, threohydroxybupropion, or a metabolite or prodrug of any of these compounds include, but are not limited to, akathisia, akinesia, associated movements, athetosis, ataxia, ballismus, hemiballismus, bradykinesia, cerebral palsy, chorea, Huntington's disease, rheumatic chorea, Sydenham's chorea, dyskinesia, tardive dyskinesia, dystonia, blepharospasm, spasmodic torticollis, dopamine-responsive dystonia, Parkinson's disease, restless legs syndrome (RLS), tremor, essential tremor, and Tourette's syndrome, and Wilson's disease.

Dementias that may be treated by enhanced bioavailability or plasma levels of dextromethorphan, or by a combination of dextromethorphan and an antidepressant such as bupropion, hydroxybupropion, erythrohydroxybupropion, threohydroxybupropion, or a metabolite or prodrug of any of these compounds include, but are not limited to, Alzheimer's disease, Parkinson's disease, vascular dementia, dementia with Lewy bodies, mixed dementia, fronto-temporal dementia, Creutzfeldt-Jakob disease, normal pressure hydrocephalus, Huntington's disease, Wernicke-Korsakoff Syndrome, and Pick's disease.

Motor neuron diseases that may be treated by enhanced bioavailability or plasma levels of dextromethorphan, or by a combination of dextromethorphan and an antidepressant such as bupropion, hydroxybupropion, erythrohydroxybupropion, threohydroxybupropion, or a metabolite or prodrug of any of these compounds include, but are not limited to, amyotrophic lateral sclerosis (ALS), progressive bulbar palsy, primary lateral sclerosis (PLS), progressive muscular atrophy, post-polio syndrome (PPS), spinal muscular atrophy (SMA), spinal motor atrophies, Tay-Sach's disease, Sandoff disease, and hereditary spastic paraplegia.

Neurodegenerative diseases that may be treated by enhanced bioavailability or plasma levels of dextromethorphan, or by a combination of dextromethorphan and an antidepressant such as bupropion, hydroxybupropion, erythrohydroxybupropion, threohydroxybupropion, or a metabolite or prodrug of any of these compounds include, but are not limited to Alzheimer's disease, prion-related diseases, cerebellar ataxia, spinocerebellar ataxia (SCA), spinal muscular atrophy (SMA), bulbar muscular atrophy, Friedrich's ataxia, Huntington's disease, Lewy body disease, Parkinson's disease, amyotrophic lateral sclerosis (ALS or Lou Gehrig's disease), multiple sclerosis (MS), multiple system atrophy, Shy-Drager syndrome, corticobasal degeneration, progressive supranuclear palsy, Wilson's disease, Menkes disease, adrenoleukodystrophy, cerebral autosomal dominant arteriopathy with subcortical infarcts and leukoencephalopathy (CADASIL), muscular dystrophies, Charcot-Marie-Tooth disease (CMT), familial spastic paraparesis, neurofibromatosis, olivopontine cerebellar atrophy or degeneration, striatonigral degeneration, Guillain-Barré-syndrome, and spastic paraplegia.

Seizure disorders that may be treated by enhanced bioavailability or plasma levels of dextromethorphan, or by a combination of dextromethorphan and an antidepressant such as bupropion, hydroxybupropion, erythrohydroxybupropion, threohydroxybupropion, or a metabolite or prodrug of any of these compounds include, but are not limited to, epileptic seizures, nonepileptic seizures, epilepsy, febrile seizures; partial seizures including, but not limited to, simple partial seizures, Jacksonian seizures, complex partial seizures, and epilepsia partialis continua; generalized seizures including, but not limited to, generalized tonic-clonic seizures, absence seizures, atonic seizures, myoclonic seizures, juvenile myoclonic seizures, and infantile spasms; and status epilepticus.

Types of headaches that may be treated by enhanced bioavailability or plasma levels of dextromethorphan, or by a combination of dextromethorphan and an antidepressant such as bupropion, hydroxybupropion, erythrohydroxybupropion, threohydroxybupropion, or a metabolite or prodrug of any of these compounds include, but are not limited to, migraine, tension, and cluster headaches.

Other neurological disorders that may be treated by enhanced bioavailability or plasma levels of dextromethorphan, or by a combination of dextromethorphan and an antidepressant such as bupropion, hydroxybupropion, erythrohydroxybupropion, threohydroxybupropion, or a metabolite or prodrug of any of these compounds include, Rett Syndrome, autism, tinnitus, disturbances of consciousness disorders, sexual dysfunction, intractable coughing, narcolepsy, cataplexy; voice disorders due to uncontrolled laryngeal muscle spasms, including, but not limited to, abductor spasmodic dysphonia, adductor spasmodic dysphonia, muscular tension dysphonia, and vocal tremor; diabetic neuropathy, chemotherapy-induced neurotoxicity, such as methotrexate neurotoxicity; incontinence including, but not limited, stress urinary incontinence, urge urinary incontinence, and fecal incontinence; and erectile dysfunction.

In some embodiments, a combination of dextromethorphan and an antidepressant such as bupropion, hydroxybupropion, erythrohydroxybupropion, threohydroxybupropion, or a metabolite or prodrug of any of these compounds, may be used to treat pain, joint pain, pain associated with sickle cell disease, pseudobulbar affect, depression (including treatment resistant depression), disorders related to memory and cognition, schizophrenia, Parkinson's disease, amyotrophic lateral sclerosis (ALS), Rhett's syndrome, seizures, cough (including chronic cough), etc.

In some embodiments, a combination of dextromethorphan and an antidepressant such as bupropion, hydroxybupropion, erythrohydroxybupropion, threohydroxybupropion, or a metabolite or prodrug of any of these compounds may be used to treat treatment refractory depression.

In some embodiments, a combination of dextromethorphan and an antidepressant such as bupropion, hydroxybupropion, erythrohydroxybupropion, threohydroxybupropion, or a metabolite or prodrug of any of these compounds may be used to treat allodynia.

In some embodiments, a combination of dextromethorphan and an antidepressant such as bupropion, hydroxybupropion, erythrohydroxybupropion, threohydroxybupropion, or a metabolite or prodrug of any of these compounds may be used to treat treatment refractory hyperalgesia.

In some embodiments, a combination of dextromethorphan and an antidepressant such as bupropion, hydroxybupropion, erythrohydroxybupropion, threohydroxybupropion, or a metabolite or prodrug of any of these compounds may be used to treat dermatitis.

Pain relieving properties of dextromethorphan may be enhanced by a method comprising co-administering dextromethorphan and an antidepressant, such as bupropion, hydroxybupropion, erythrohydroxybupropion, threohydroxybupropion, or a metabolite or prodrug of any of these compounds, with dextromethorphan.

Pain relieving properties of bupropion may be enhanced by a method comprising co-administering dextromethorphan with bupropion, hydroxybupropion, erythrohydroxybupropion, threohydroxybupropion, or a metabolite or prodrug of any of these compounds.

In some embodiments, ketamine or another NMDA receptor antagonist may be administered with an antidepressant, such as bupropion, hydroxybupropion, erythrohydroxybupropion, threohydroxybupropion, or a metabolite or prodrug of any of these compounds.

In some embodiments, dextromethorphan and quinidine may be co-administered with an antidepressant, such as bupropion, hydroxybupropion, erythrohydroxybupropion, threohydroxybupropion, or a metabolite or prodrug of any of these compounds.

These methods may be used to treat, or provide relief to, any type of pain including, but not limited to, musculoskeletal pain, neuropathic pain, cancer-related pain, acute pain, nociceptive pain, inflammatory pain, arthritis pain, complex regional pain syndrome, etc.

In some embodiments, co-administering dextromethorphan with bupropion, hydroxybupropion, erythrohydroxybupropion, threohydroxybupropion, or a metabolite or prodrug of any of these compounds may be used to treat or reduce inflammation or inflammatory conditions, such as Crohn's disease, including pain associated with inflammation.

In some embodiments, co-administering dextromethorphan with bupropion, hydroxybupropion, erythrohydroxybupropion, threohydroxybupropion, or a metabolite or prodrug of any of these compounds may be used to treat psoriasis, cancer, viral infection, or as an adjuvant treatment for multiple myeloma.

Examples of musculoskeletal pain include low back pain (i.e. lumbosacral pain), primary dysmenorrhea, and arthritic pain, such as pain associated with rheumatoid arthritis, juvenile rheumatoid arthritis, osteoarthritis, axial spondylarthritis including ankylosing spondylitis, pain associated with vertebral crush fractures, fibrous dysplasia, osteogenesis imperfecta, Paget's disease of bone, transient osteoporosis, and transient osteoporosis of the hip, etc.

In some embodiments, a combination of dextromethorphan and an antidepressant, such as bupropion, may be administered orally to relieve musculoskeletal pain including low back pain, and pain associated with rheumatoid arthritis, juvenile rheumatoid arthritis, osteoarthritis, erosive osteoarthritis, sero-negative (non-rheumatoid) arthropathies, non-articular rheumatism, peri-articular disorders, axial spondyloarthritis including ankylosing spondylitis, Paget's disease, fibrous dysplasia, SAPHO syndrome, transient osteoarthritis of the hip, vertebral crush fractures, osteoporosis, etc.

In some embodiments, a combination of dextromethorphan and an antidepressant, such as bupropion, may be administered to relieve inflammatory pain including musculoskeletal pain, arthritis pain, and complex regional pain syndrome.

Arthritis refers to inflammatory joint diseases that can be associated with pain. Examples of arthritis pain include pain associated with osteoarthritis, erosive osteoarthritis, rheumatoid arthritis, juvenile rheumatoid arthritis, sero-negative (non-rheumatoid) arthropathies, non-articular rheumatism, peri-articular disorders, neuropathic arthropathies including Charcot's foot, axial spondyloarthritis including ankylosing spondylitis, and SAPHO syndrome.

In some embodiments, a combination of dextromethorphan and an antidepressant, such as bupropion, is used to treat chronic musculoskeletal pain.

In some embodiments, a combination of dextromethorphan and an antidepressant, such as bupropion, may be administered to relieve complex regional pain syndrome, such as complex regional pain syndrome type I (CRPS-I), complex regional pain syndrome type II (CRPS-II), CRPS-NOS, or another type of CRPS. CRPS is a type of inflammatory pain. CRPS can also have a neuropathic component. Complex regional pain syndrome is a debilitating pain syndrome. It is characterized by severe pain in a limb that can be accompanied by edema, and autonomic, motor and sensory changes.

In some embodiments, a combination of dextromethorphan and an antidepressant, such as bupropion, may be administered orally to relieve neuropathic pain.

Examples of neuropathic pain include diabetic peripheral neuropathy, post-herpetic neuralgia, trigeminal neuralgia, monoradiculopathies, phantom limb pain, central pain, etc. Other causes of neuropathic pain include cancer-related pain, lumbar nerve root compression, spinal cord injury, post-stroke pain, central multiple sclerosis pain, HIV-associated neuropathy, and radio- or chemo-therapy associated neuropathy, etc.

In some embodiments, a combination of dextromethorphan and an antidepressant, such as bupropion, may be administered to relieve fibromyalgia.

The term "treating" or "treatment" includes the diagnosis, cure, mitigation, treatment, or prevention of disease in man or other animals, or any activity that otherwise affects the structure or any function of the body of man or other animals.

Any antidepressant may be used in combination with dextromethorphan to improve the therapeutic properties of dextromethorphan. Dextromethorphan and the antidepressant compound may be administered in separate compositions or dosage forms, or may be administered in a single composition or dosage form comprising both.

A quinidine may be co-administered with dextromethorphan to provide enhanced plasma levels of dextromethorphan. For a combination of a quinidine and a dextromethorphan (including deuterium-modified dextromethorphan, e.g. d6-dextromethorphan, and non-deuterium modified dextromethorphan), a daily dose of about 1-1,000 mg, 1-10 mg, 10 mg, about 5 mg, about 4.5, about 1-3 mg, about 2-4 mg, about 3-5 mg, about 4-6 mg, about 5-7 mg, about 6-8 mg, about 7-9 mg, about 8-10 mg, about 9-11 mg, about 10-12 mg, about 4.5-5 mg, 20 mg, 30 mg, 30-100 mg, about 40 mg, about 50 mg, about 60 mg, about 70 mg, about 80 mg, about 90 mg, about 10-30 mg, about 30-50 mg, about 50-70 mg, about 10-90 mg of the quinidine, or any dose in a range bounded by any of these values.

Antidepressant compounds that can be co-administered with dextromethorphan include, but are not limited to, bupropion, hydroxybupropion, erythrohydroxybupropion, threohydroxybupropion, clomipramine, doxepin, fluoxetine, mianserin, imipramine, 2-chloroimipramine, amitriptyline, amoxapine, desipramine, protriptyline, trimipramine, nortriptyline, maprotiline, phenelzine, isocarboxazid, tranylcypromine, paroxetine, trazodone, citalopram, sertraline, aryloxy indanamine, benactyzine, escitalopram, fluvoxamine, venlafaxine, desvenlafaxine, duloxetine, mirtazapine, nefazodone, selegiline, sibutramine, milnacipran, tesofensine, brasofensine, moclobemide, rasagiline, nialamide, iproniazid, iproclozide, toloxatone, butriptyline, dosulepin, dibenzepin, iprindole, lofepramine, opipramol, norfluoxetine, dapoxetine, ketamine, etc., or a metabolite or prodrug of any of these compounds, or a pharmaceutically acceptable salt of any of these compounds.

For a combination of a ketamine and a dextromethorphan (including deuterium-modified dextromethorphan, e.g. d6-dextromethorphan, and non-deuterium modified dextromethorphan), a daily dose of about 0.01-0.2 mg, about 0.2-0.4 mg, about 0.4-0.6 mg, about 0.6-0.8 mg, about 0.8-1 mg, about 1-1.2 mg, about 1.2-1.4 mg, about 1.4-1.6 mg, about 1.6-1.8 mg, about 1.8-2 mg, about 2-2.2 mg, about 2.2-2.4 mg, about 2.4-2.6 mg, about 2.6-2.8 mg, about 2.8-3 mg, about 3-3.2 mg, about 3.2-3.4 mg, about 3.4-3.6 mg, about 3.6-3.8 mg, about 3.8-4 mg, about 3.9-4.1 mg, about 4-4.2 mg, about 0.2-0.4 mg, about 0.2-0.6 mg, about 0.2-0.8 mg, about 0.2-1 mg, about 0.2-1.2 mg, about 0.2-1.4 mg, about 0.2-1.6 mg, about 0.2-1.8 mg, about 0.2-2.0 mg, 0.2-2.5 mg, about 0.2-3.0 mg, about 0.2-3.5 mg, about 0.2-4.0 mg, about 5-10 mg, about 10-15 mg, about 15-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240, about 10-500 mg, about 50-400 mg, about 50-300 mg, about 100-250 mg, about 1-10 mg, about 10-200 mg, about 10-150 mg, about 10-100 mg, about 10-180 mg, about 10-160 mg, about 10-140 mg, about 10-120 mg, about 10-100 mg, about 10-20 mg, about 20-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-160 mg, about 160-180 mg, about 180-200 mg, about 200-220 mg, about 220-240, about 240-250 mg, about 250-260 mg, about 260-280 mg, about 280-300 mg, about 300-350 mg, about 350-400 mg, about 25 mg, about 50 mg, about 100 mg, about 250 mg, of the ketamine, or any dose in a range bounded by any of these values, may be administered.

For a combination of a tesofensine and a dextromethorphan (including deuterium-modified dextromethorphan, e.g. d6-dextromethorphan, and non-deuterium modified dextromethorphan), a daily dose of about 0.1-0.2 mg, about 0.1-0.3 mg, about 0.1-0.4 mg, about 0.1-0.5 mg, about 0.1-0.6 mg, about 0.1-0.7 mg, about 0.1-0.8 mg, about 0.1-0.9 mg, about 0.1-0.1 mg, about 0.1-0.12 mg, 0.01-0.2 mg, about 0.1-0.3 mg, about 0.2-0.4 mg, about 0.3-0.5 mg, about 0.4-0.6 mg, about 0.5-0.7 mg, about 0.6-0.8 mg, about 0.7-0.9 mg, about 0.8-1 mg, about 0.9-1.1 mg, of the tesofensine, or any dose in a range bounded by any of these values, may be administered.

For a combination of a brasofensine and a dextromethorphan (including deuterium-modified dextromethorphan, e.g. d6-dextromethorphan, and non-deuterium modified dextromethorphan), a daily dose of about 0.01-0.2 mg, about 0.2-0.4 mg, about 0.4-0.6 mg, about 0.6-0.8 mg, about 0.8-1 mg, about 1-1.2 mg, about 1.2-1.4 mg, about 1.4-1.6 mg, about 1.6-1.8 mg, about 1.8-2 mg, about 2-2.2 mg, about 2.2-2.4 mg, about 2.4-2.6 mg, about 2.6-2.8 mg, about 2.8-3 mg, about 3-3.2 mg, about 3.2-3.4 mg, about 3.4-3.6 mg, about 3.6-3.8 mg, about 3.8-4 mg, about 3.9-4.1 mg, about 4-4.2 mg, about 0.2-0.4 mg, about 0.2-0.6 mg, about 0.2-0.8 mg, about 0.2-1 mg, about 0.2-1.2 mg, about 0.2-1.4 mg, about 0.2-1.6 mg, about 0.2-1.8 mg, about 0.2-2.0 mg, 0.2-2.5 mg, about 0.2-3.0 mg, about 0.2-3.5 mg, about 0.2-4.0 mg, of the brasofensine, or any dose in a range bounded by any of these values, may be administered.

For a combination of a clomipramine and a dextromethorphan (including deuterium-modified dextromethorphan, e.g. d6-dextromethorphan, and non-deuterium modified dextromethorphan), a daily dose of about 10-500 mg, about 50-400 mg, about 50-300 mg, about 100-250 mg, about 1-10 mg, about 10-200 mg, about 10-150 mg, about 10-100 mg, about 10-180 mg, about 10-160 mg, about 10-140 mg, about 10-120 mg, about 10-100 mg, about 10-20 mg, about 20-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-160 mg, about 160-180 mg, about 180-200 mg, about 200-220 mg, about 220-240, about 240-250 mg, about 250-260 mg, about 260-280 mg, about 280-300 mg, about 300-350 mg, about 350-400 mg, about 25 mg, about 50 mg, about 100 mg, about 250 mg, of the clomipramine, or any dose in a range bounded by any of these values, may be administered.

For a combination of a doxepin and a dextromethorphan (including deuterium-modified dextromethorphan, e.g. d6-dextromethorphan, and non-deuterium modified dextromethorphan), a daily dose of about 1-500 mg, about 1-10 mg, about 1-40 mg, about 1-30 mg, about 1-20 mg, about 1-18 mg, about 1-16 mg, about 1-14 mg, about 1-12 mg, about 1-10 mg, about 10-150 mg, about 10-125 mg, about 10-100 mg, about 10-75 mg, about 10-70 mg, about 10-60 mg, about 10-50 mg, about 10-40 mg, about 10-30 mg, about 10-20 mg, about 20-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-160 mg, about 160-180 mg, about 180-200 mg, about 200-220 mg, about 220-240, about 240-250 mg, about 250-260 mg, about 260-280 mg, about 280-300 mg, about 300-320 mg, about 320-350 mg, about 350-400 mg, about 400-500 mg, about 25 mg, about 50 mg, about 75 mg, about 100 mg, about 150 mg, about 250 mg, about 300 mg, of the doxepin, or any dose in a range bounded by any of these values, may be administered.

For a combination of a fluoxetine and a dextromethorphan (including deuterium-modified dextromethorphan, e.g. d6-dextromethorphan, and non-deuterium modified dextromethorphan), a daily dose of a daily dose of about 1-10 mg, about 5-15 mg, about 10-20 mg, about 20-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-160 mg, about 160-180 mg, about 180-200 mg, about 10 mg, about 20 mg, about 60 mg, about 100 mg, about 150 mg, of the fluoxetine, or any dose in a range bounded by any of these values, may be administered.

For a combination of a mianserin and a dextromethorphan (including deuterium-modified dextromethorphan, e.g. d6-dextromethorphan, and non-deuterium modified dextromethorphan), a daily dose of about 1-300 mg, about 1-90 mg, about 1-60 mg, about 1-30 mg, about 1-25 mg, about 1-20 mg, about 1-15 mg, about 1-10 mg, about 10-20 mg, about 20-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-160 mg, about 160-180 mg, about 180-200 mg, about 30 mg, about 60 mg, about 90 mg, about 120 mg, about 150 mg, of the mianserin, or any dose in a range bounded by any of these values, may be administered.

For a combination of a imipramine and a dextromethorphan (including deuterium-modified dextromethorphan, e.g. d6-dextromethorphan, and non-deuterium modified dextromethorphan), a daily dose of about 1-10 mg, about 5-150 mg, about 5-125 mg, about 5-100 mg, about 5-75 mg, about 5-60 mg, about 5-50 mg, about 5-40 mg, about 5-30 mg, about 5-25 mg, about 5-20 mg, about 5-15 mg, about 10-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-160 mg, about 160-180 mg, about 180-200 mg, about 200-220 mg, about 220-240, about 240-250 mg, about 250-260 mg, about 260-280 mg, about 280-300 mg, about 300-320 mg, about 320-350 mg, about 350-400 mg, about 400-500 mg, about 25 mg, about 50 mg, about 75 mg, about 100 mg, about 150 mg, about 250 mg, about 300 mg, of the imipramine, or any dose in a range bounded by any of these values, may be administered.

For a combination of a about 2-chloroimipramine and a dextromethorphan (including deuterium-modified dextromethorphan, e.g. d6-dextromethorphan, and non-deuterium modified dextromethorphan), a daily dose of about 0.1-0.25 mg, about 0.25-0.5 mg, about 0.5-0.75 mg, about 0.75-1 mg, about 1-5 mg, about 5-10 mg, about 10-15 mg, about 15-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 700-800 mg, about 800-1000 mg, about 25 mg, about 50 mg, about 75 mg, about 100 mg, about 150 mg, about 250 mg, about 300 mg, about 400 mg, about 600 mg, of the about 2-chloroimipramine, or any dose in a range bounded by any of these values, may be administered.

For a combination of an amitriptyline and a dextromethorphan (including deuterium-modified dextromethorphan, e.g. d6-dextromethorphan, and non-deuterium modified dextromethorphan), a daily dose of about 1-10 mg, about 5-100 mg, about 5-70 mg, about 5-60 mg, about 5-50 mg, about 5-40 mg, about 5-35 mg, about 5-30 mg, about 5-25 mg, about 5-20 mg, about 10-20 mg, about 20-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-160 mg, about 160-180 mg, about 180-200 mg, about 200-220 mg, about 220-240, about 240-250 mg, about 250-260 mg, about 260-280 mg, about 280-300 mg, about 300-320 mg, about 320-350 mg, about 350-400 mg, about 400-500 mg, about 10 mg, about 25 mg, about 50 mg, about 75 mg, about 100 mg, about 150 mg, about 250 mg, about 300 mg, of the amitriptyline, or any dose in a range bounded by any of these values, may be administered.

For a combination of an amoxapine and a dextromethorphan (including deuterium-modified dextromethorphan, e.g. d6-dextromethorphan, and non-deuterium modified dextromethorphan), a daily dose of about 1-10 mg, about 10-20 mg, about 10-300 mg, about 10-250 mg, about 10-200 mg, about 10-150 mg, about 10-120 mg, about 10-100 mg, about 10-80 mg, about 10-60 mg, about 10-40 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-160 mg, about 160-180 mg, about 180-200 mg, about 200-220 mg, about 220-240, about 240-250 mg, about 250-260 mg, about 260-280 mg, about 280-300 mg, about 300-320 mg, about 320-350 mg, about 350-400 mg, about 400-500 mg, about 500-600 mg, about 600-700 mg, about 700-800 mg, about 25 mg, about 50 mg, about 75 mg, about 100 mg, about 150 mg, about 250 mg, about 300 mg, about 400 mg, of the amoxapine, or any dose in a range bounded by any of these values, may be administered.

For a combination of a desipramine and a dextromethorphan (including deuterium-modified dextromethorphan, e.g. d6-dextromethorphan, and non-deuterium modified dextromethorphan), a daily dose of about 1-10 mg, 1-15 mg, about 10-20 mg, 10-25 mg, about 10-30 mg, about 10-40 mg, about 10-50 mg, about 10-60 mg, about 10-70 mg, about 10-80 mg, about 10-90 mg, about 10-100 mg, about 10-120 mg, about 10-140 mg, about 10-150 mg, about 10-180 mg, about 10-200 mg, about 20-30 mg, about 20-40 mg, about 30-40 mg, about 40-50 mg, about 40-60 mg, about 50-60 mg, about 60-70 mg, about 70-80 mg, about 80-90 mg, about 90-100 mg, about 90-110 mg, about 100-120 mg, about 120-140 mg, about 140-160 mg, about 160-180 mg, about 180-200 mg, about 180-220 mg, about 200-220 mg, about 220-240, about 240-250 mg, about 250-260 mg, about 260-280 mg, about 280-300 mg, about 280-320 mg, about 300-350 mg, about 350-400 mg, about 400 mg, about 100-200 mg, about 25-100 mg, about 25 mg, about 50 mg, about 100 mg, about 200 mg, about 250 mg, of the desipramine, or any dose in a range bounded by any of these values, may be administered.

For a combination of a protriptyline and a dextromethorphan (including deuterium-modified dextromethorphan, e.g. d6-dextromethorphan, and non-deuterium modified dextromethorphan), a daily dose of about 5-100 mg, about 2-5 mg, about 2-6 mg, about 2-7 mg, about 2-8 mg, about 2-9 mg, about 2-10 mg, about 2-11 mg, about 2-12 mg, about 2-13 mg, about 2-14 mg, about 2-15 mg, about 2-20 mg, about 2-21 mg, about 2-22 mg, about 2-23 mg, about 2-24 mg, about 2-25 mg, about 2-26 mg, about 2-27 mg, about 2-28 mg, about 2-29 mg, about 2-30 mg, about 2-35 mg, about 2-40 mg, about 15-60 mg, about 1-5 mg, about 5-10 mg, about 10-15 mg, about 15-20 mg, about 20-25 mg, about 25-30 mg, about 30-35 mg, about 35-40 mg, about 40-45 mg, about 45-50 mg, about 50-55 mg, about 55-60 mg, about 60-65 mg, about 65-70 mg, about 70-80 mg, about 80-90 mg, about 90-100 mg, about 100-120 mg, about 120-140 mg, about 140-160 mg, about 160-180 mg, about 180-200 mg, about 10 mg, about 20 mg, about 30 mg, about 60 mg, about 100 mg, about 150 mg, of the protriptyline, or any dose in a range bounded by any of these values, may be administered.

For a combination of a trimipramine and a dextromethorphan (including deuterium-modified dextromethorphan, e.g. d6-dextromethorphan, and non-deuterium modified dextromethorphan), a daily dose of 20-300 mg, 1-10 mg, about 5-20 mg, about 5-25 mg, about 5-30 mg, about 5-35 mg, about 5-40 mg, about 5-45 mg, about 5-50 mg, about 5-55 mg, about 5-60 mg, about 5-65 mg, about 5-70 mg, about 5-75 mg, about 5-100 mg, about 5-125 mg, about 5-150 mg, about 10-20 mg, about 20-30 mg, about 30-40 mg, about 40-50 mg, about 50-60 mg, about 60-70 mg, about 70-80 mg, about 80-90 mg, about 90-100 mg, about 100-120 mg, about 100-200 mg, about 120-140 mg, about 140-160 mg, about 160-180 mg, about 180-200 mg, about 180-220 mg, about 200-220 mg, about 220-240, about 240-250 mg, about 250-260 mg, about 260-280 mg, about 280-300 mg, about 300-320 mg, about 320-350 mg, about 350-400 mg, about 400-500 mg, about 10 mg, about 25 mg, about 50 mg, about 75 mg, about 100 mg, about 150 mg, about 250 mg, about 300 mg, of the trimipramine, or any dose in a range bounded by any of these values, may be administered.

For a combination of a nortriptyline and a dextromethorphan (including deuterium-modified dextromethorphan, e.g. d6-dextromethorphan, and non-deuterium modified dextromethorphan), a daily dose of about 1-5 mg, about 5-10 mg, about 5-20 mg, about 5-25 mg, about 5-30 mg, about 5-35 mg, about 5-40 mg, about 5-45 mg, about 5-50 mg, about 5-55 mg, about 5-60 mg, about 5-65 mg, about 5-70 mg, about 5-75 mg, about 5-100 mg, about 5-125 mg, about 5-150 mg, about 10-15 mg, about 15-20 mg, about 20-25 mg, about 20-30 mg, about 25-30 mg, about 30-35 mg, about 30-50 mg, about 35-40 mg, about 40-45 mg, about 45-50 mg, about 50-150 mg, about 50-55 mg, about 55-60 mg, about 60-65 mg, about 65-70 mg, about 70-80 mg, about 80-90 mg, 80-120 mg, about 90-100 mg, about 100-120 mg, about 120-140 mg, about 140-160 mg, about 160-180 mg, about 180-200 mg, about 10 mg, about 20 mg, about 30 mg, about 60 mg, about 100 mg, about 150 mg, of the nortriptyline, or any dose in a range bounded by any of these values, may be administered.

For a combination of a maprotiline and a dextromethorphan (including deuterium-modified dextromethorphan, e.g. d6-dextromethorphan, and non-deuterium modified dextromethorphan), a daily dose of about 1-5 mg, about 5-10 mg, about 5-20 mg, about 5-25 mg, about 5-30 mg, about 5-35 mg, about 5-40 mg, about 5-45 mg, about 5-50 mg, about 5-55 mg, about 5-60 mg, about 5-65 mg, about 5-70 mg, about 5-75 mg, about 5-100 mg, about 5-125 mg, about 5-150 mg, about 10-15 mg, about 10-250 mg, about 10-75 mg, about 10-50 mg, about 15-20 mg, about 20-25 mg, about 25-30 mg, about 30-35 mg, about 35-40 mg, about 40-45 mg, about 45-50 mg, about 50-55 mg, about 55-60 mg, about 60-65 mg, about 60-90 mg, about 65-70 mg, about 70-75 mg, about 75-80 mg, about 80-85 mg, about 80-120 mg, about 85-90 mg, about 90-100 mg, about 100-120 mg, about 100-150 mg, about 120-125 mg, about 125-140 mg, about 140-150 mg, about 150-160 mg, about 160-180 mg, about 180-200 mg, about 200-225 mg, about 210-240 mg, about 200-250 mg, about 10 mg, about 25 mg, about 30 mg, about 50 mg, about 75 mg, about 100 mg, about 150 mg, about 225 mg, of the maprotiline, or any dose in a range bounded by any of these values, may be administered.

For a combination of a phenelzine and a dextromethorphan (including deuterium-modified dextromethorphan, e.g. d6-dextromethorphan, and non-deuterium modified dextromethorphan), a daily dose of about 1-5 mg, about 5-10 mg, about 5-20 mg, about 5-25 mg, about 5-30 mg, about 5-35 mg, about 5-40 mg, about 5-45 mg, about 5-50 mg, about 5-55 mg, about 5-60 mg, about 5-65 mg, about 5-70 mg, about 5-75 mg, about 5-90 mg, about 10-15 mg, about 15-20 mg, about 20-25 mg, about 25-30 mg, about 30-35 mg, about 35-40 mg, about 40-45 mg, about 40-50 mg, about 45-50 mg, about 50-55 mg, about 50-70 mg, about 50-200 mg, about 55-60 mg, about 60-65 mg, about 60-90 mg, about 65-70 mg, about 70-80 mg, about 80-90 mg, 80-120 mg, about 90-100 mg, about 100-120 mg, about 100-150 mg, about 120-140 mg, about 140-160 mg, about 160-180 mg, about 180-200 mg, about 10 mg, about 15 mg, about 30 mg, about 60 mg, about 100 mg, about 150 mg, of the phenelzine, or any dose in a range bounded by any of these values, may be administered.

For a combination of a isocarboxazid and a dextromethorphan (including deuterium-modified dextromethorphan, e.g. d6-dextromethorphan, and non-deuterium modified dextromethorphan), a daily dose of about 1-5 mg, about 2-5 mg, about 2-6 mg, about 2-7 mg, about 2-8 mg, about 2-9 mg, about 2-10 mg, about 2-11 mg, about 2-12 mg, about 2-13 mg, about 2-14 mg, about 2-15 mg, about 2-16 mg, about 2-17 mg, about 2-18 mg, about 2-19 mg, about 2-20 mg, about 2-21 mg, about 2-22 mg, about 2-23 mg, about 2-24 mg, about 2-25 mg, about 2-26 mg, about 2-27 mg, about 2-28 mg, about 2-29 mg, about 2-30 mg, about 2-35 mg, about 2-40 mg, about 2-45 mg, about 2-50 mg, about 2-55 mg, about 2-60 mg, about 5-10 mg, about 5-15 mg, about 10-15 mg, about 10-60 mg, about 15-20 mg, about 20-25 mg, about 25-30 mg, about 30-35 mg, about 30-50 mg, about 35-40 mg, about 40-45 mg, about 45-50 mg, about 50-55 mg, about 50-70 mg, about 55-60 mg, about 60-65 mg, about 65-70 mg, about 70-80 mg, about 80-90 mg, about 90-100 mg, about 100-120 mg, about 120-140 mg, about 140-160 mg, about 160-180 mg, about 180-200 mg, about 10 mg, about 15 mg, about 30 mg, about 60 mg, about 100 mg, about 150 mg, of the isocarboxazid, or any dose in a range bounded by any of these values, may be administered.

For a combination of a tranylcypromine and a dextromethorphan (including deuterium-modified dextromethorphan, e.g. d6-dextromethorphan, and non-deuterium modified dextromethorphan), a daily dose of about 1-5 mg, about 1-30 mg, about 1-25 mg, about 1-20 mg, about 2-5 mg, about 2-6 mg, about 2-7 mg, about 2-8 mg, about 2-9 mg, about 2-10 mg, about 2-11 mg, about 2-12 mg, about 2-13 mg, about 2-14 mg, about 2-15 mg, about 2-16 mg, about 2-17 mg, about 2-18 mg, about 2-19 mg, about 2-20 mg, about 2-21 mg, about 2-22 mg, about 2-23 mg, about 2-24 mg, about 2-25 mg, about 2-26 mg, about 2-27 mg, about 2-28 mg, about 2-29 mg, about 2-30 mg, about 2-35 mg, about 2-40 mg, about 2-45 mg, about 2-50 mg, about 2-55 mg, about 2-60 mg, about 5-10 mg, about 10-15 mg, about 15-20 mg, about 20-25 mg, about 25-30 mg, about 30-35 mg, about 35-40 mg, about 40-45 mg, about 45-50 mg, about 50-55 mg, about 55-60 mg, about 60-65 mg, about 65-70 mg, about 70-80 mg, about 80-90 mg, about 90-100 mg, about 100-120 mg, about 120-140 mg, about 140-160 mg, about 160-180 mg, about 180-200 mg, about 10 mg, about 15 mg, about 30 mg, about 60 mg, about 100 mg, about 150 mg, of the tranylcypromine, or any dose in a range bounded by any of these values, may be administered.

For a combination of a paroxetine and a dextromethorphan (including deuterium-modified dextromethorphan, e.g. d6-dextromethorphan, and non-deuterium modified dextromethorphan), a daily dose of about 1-5 mg, about 1-50 mg, about 1-20 mg, about 1-15 mg, about 1-10 mg, about 2-5 mg, about 2-6 mg, about 2-7 mg, about 2-8 mg, about 2-9 mg, about 2-10 mg, about 2-11 mg, about 2-12 mg, about 2-13 mg, about 2-14 mg, about 2-15 mg, about 2-16 mg, about 2-17 mg, about 2-18 mg, about 2-19 mg, about 2-20 mg, about 2-30 mg, about 2-40 mg, about 2-50 mg, about 5-10 mg, about 10-15 mg, about 15-20 mg, about 20-25 mg, about 25-30 mg, about 30-35 mg, about 35-40 mg, about 40-45 mg, about 45-50 mg, about 50-55 mg, about 55-60 mg, about 60-65 mg, about 65-70 mg, about 70-80 mg, about 80-90 mg, about 90-100 mg, about 100-120 mg, about 120-140 mg, about 140-160 mg, about 160-180 mg, about 180-200 mg, about 10 mg, about 15 mg, about 20 mg, about 30 mg, about 60 mg, about 100 mg, about 150 mg, of the paroxetine, or any dose in a range bounded by any of these values, may be administered.

For a combination of a trazodone and a dextromethorphan (including deuterium-modified dextromethorphan, e.g. d6-dextromethorphan, and non-deuterium modified dextromethorphan), a daily dose of about 1-10 mg, about 10-20 mg, about 10-30 mg, about 10-40 mg, about 10-50 mg, about 10-60 mg, about 10-70 mg, about 10-80 mg, about 10-90 mg, about 10-100 mg, about 10-120 mg, about 10-140 mg, about 10-150 mg, about 10-180 mg, about 10-200 mg, about 10-250 mg, about 10-300 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 25 mg, about 50 mg, about 75 mg, about 100 mg, about 150 mg, about 250 mg, about 300 mg, about 400 mg, about 600 mg, of the trazodone, or any dose in a range bounded by any of these values, may be administered.

For a combination of a citalopram and a dextromethorphan (including deuterium-modified dextromethorphan, e.g. d6-dextromethorphan, and non-deuterium modified dextromethorphan), a daily dose of about 1-5 mg, about 1-20 mg, about 1-15 mg, about 1-10 mg, about 2-5 mg, about 2-6 mg, about 2-7 mg, about 2-8 mg, about 2-9 mg, about 2-10 mg, about 2-11 mg, about 2-12 mg, about 2-13 mg, about 2-14 mg, about 2-15 mg, about 2-20 mg, about 2-25 mg, about 2-30 mg, about 2-35 mg, about 2-40 mg, about 5-10 mg, about 10-15 mg, about 15-20 mg, about 20-25 mg, about 25-30 mg, about 30-35 mg, about 35-40 mg, about 40-45 mg, about 45-50 mg, about 50-55 mg, about 55-60 mg, about 60-65 mg, about 65-70 mg, about 70-80 mg, about 80-90 mg, about 90-100 mg, about 100-120 mg, about 120-140 mg, about 140-160 mg, about 160-180 mg, about 180-200 mg, about 10 mg, about 15 mg, about 20 mg, about 30 mg, about 40 mg, about 60 mg, about 100 mg, about 150 mg, of the citalopram, or any dose in a range bounded by any of these values, may be administered.

For a combination of a sertraline and a dextromethorphan (including deuterium-modified dextromethorphan, e.g. d6-dextromethorphan, and non-deuterium modified dextromethorphan), a daily dose of about 1-5 mg, about 1-50 mg, about 1-45 mg, about 1-40 mg, about 1-30 mg, about 1-20 mg, about 2-5 mg, about 2-6 mg, about 2-7 mg, about 2-8 mg, about 2-9 mg, about 2-10 mg, about 2-11 mg, about 2-12 mg, about 2-13 mg, about 2-14 mg, about 2-15 mg, about 2-16 mg, about 2-17 mg, about 2-18 mg, about 2-19 mg, about 2-20 mg, about 2-21 mg, about 2-22 mg, about 2-23 mg, about 2-24 mg, about 2-25 mg, about 2-26 mg, about 2-27 mg, about 2-28 mg, about 2-29 mg, about 2-30 mg, about 2-35 mg, about 2-40 mg, about 2-45 mg, about 2-50 mg, about 5-10 mg, about 10-15 mg, about 15-20 mg, about 20-25 mg, about 25-30 mg, about 30-35 mg, about 35-40 mg, about 40-45 mg, about 45-50 mg, about 50-55 mg, about 55-60 mg, about 60-65 mg, about 65-70 mg, about 70-75 mg, about 75-80 mg, about 80-85 mg, about 85-90 mg, about 90-100 mg, about 100-120 mg, about 120-125 mg, about 125-140 mg, about 140-150 mg, about 150-160 mg, about 160-180 mg, about 180-200 mg, about 200-300 mg, about 10 mg, about 25 mg, about 30 mg, about 50 mg, about 75 mg, about 100 mg, about 150 mg, about 200 mg, about 225 mg, of sertraline, or any dose in a range bounded by any of these values, may be administered.

For a combination of an aryloxy indanamine and a dextromethorphan (including deuterium-modified dextromethorphan, e.g. d6-dextromethorphan, and non-deuterium modified dextromethorphan), a daily dose of about 0.1-0.25 mg, about 0.25-0.5 mg, about 0.5-0.75 mg, about 0.75-1 mg, about 1-5 mg, about 5-10 mg, about 10-15 mg, about 15-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 700-800 mg, about 800-1000 mg, about 25 mg, about 50 mg, about 75 mg, about 100 mg, about 150 mg, about 250 mg, about 300 mg, about 400 mg, about 600 mg, of the aryloxy indanamine, or any dose in a range bounded by any of these values, may be administered.

For a combination of a benactyzine and a dextromethorphan (including deuterium-modified dextromethorphan, e.g. d6-dextromethorphan, and non-deuterium modified dextromethorphan), a daily dose of about 0.1-0.25 mg, about 0.25-0.5 mg, about 0.5-0.75 mg, about 0.75-1 mg, about 1-5 mg, about 5-10 mg, about 10-15 mg, about 15-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 700-800 mg, about 800-1000 mg, about 25 mg, about 50 mg, about 75 mg, about 100 mg, about 150 mg, about 250 mg, about 300 mg, about 400 mg, about 600 mg, of the benactyzine, or any dose in a range bounded by any of these values, may be administered.

For a combination of a escitalopram and a dextromethorphan (including deuterium-modified dextromethorphan, e.g. d6-dextromethorphan, and non-deuterium modified dextromethorphan), a daily dose of about 1-5 mg, about 2-5 mg, about 2-6 mg, about 2-7 mg, about 2-8 mg, about 2-9 mg, about 2-10 mg, about 2-12 mg, about 2-14 mg, about 2-15 mg, about 2-20 mg, about 5-10 mg, about 5-15 mg, about 10-15 mg, about 10-30 mg, about 15-20 mg, about 15-30 mg, about 20-25 mg, about 25-30 mg, about 30-35 mg, about 35-40 mg, about 40-45 mg, about 45-50 mg, about 50-55 mg, about 55-60 mg, about 60-65 mg, about 65-70 mg, about 70-80 mg, about 80-90 mg, about 90-100 mg, about 100-200 mg, about 5 mg, about 10 mg, about 15 mg, about 20 mg, about 25 mg, about 30 mg, about 35 mg, about 40 mg, about 50 mg, of the escitalopram, or any dose in a range bounded by any of these values, may be administered.

For a combination of a fluvoxamine and a dextromethorphan (including deuterium-modified dextromethorphan, e.g. d6-dextromethorphan, and non-deuterium modified dextromethorphan), a daily dose of 50-300 mg, 1-10 mg, about 10-20 mg, about 10-30 mg, about 10-40 mg, about 10-50 mg, about 10-60 mg, about 10-70 mg, about 10-80 mg, about 10-90 mg, about 10-100 mg, about 10-120 mg, about 10-140 mg, about 10-150 mg, about 10-180 mg, about 10-200 mg, about 10-250 mg, about 10-300 mg, about 20-30 mg, about 30-40 mg, about 40-50 mg, about 50-60 mg, about 60-70 mg, about 70-80 mg, about 80-90 mg, about 90-100 mg, about 90-110 mg, about 100-120 mg, about 120-140 mg, about 140-160 mg, about 160-180 mg, about 180-200 mg, about 180-220 mg, about 200-220 mg, about 220-240, about 240-250 mg, about 240-260 mg, about 250-260 mg, about 260-280 mg, about 280-300 mg, about 280-320 mg, about 300-320 mg, about 320-350 mg, about 350-400 mg, about 400-500 mg, about 10 mg, about 25 mg, about 50 mg, about 75 mg, about 100 mg, about 150 mg, about 250 mg, about 300 mg, of the fluvoxamine, or any dose in a range bounded by any of these values, may be administered.

For a combination of a venlafaxine and a dextromethorphan (including deuterium-modified dextromethorphan, e.g. d6-dextromethorphan, and non-deuterium modified dextromethorphan), a daily dose of about 1-10 mg, about 5-20 mg, about 5-25 mg, about 5-30 mg, about 5-35 mg, about 5-40 mg, about 5-45 mg, about 5-50 mg, about 5-55 mg, about 5-60 mg, about 5-65 mg, about 5-70 mg, about 5-75 mg, about 5-100 mg, about 5-125 mg, about 5-150 mg, about 10-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 120-180 mg, about 150-160 mg, about 160-180 mg, about 180-200 mg, about 200-220 mg, about 220-240, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 25 mg, about 50 mg, about 75 mg, about 100 mg, about 150 mg, about 225 mg, about 250 mg, about 375 mg, about 400 mg, about 600 mg, of the venlafaxine, or any dose in a range bounded by any of these values, may be administered.

For a combination of a desvenlafaxine and a dextromethorphan (including deuterium-modified dextromethorphan, e.g. d6-dextromethorphan, and non-deuterium modified dextromethorphan), a daily dose of about 2-5 mg, about 2-6 mg, about 2-7 mg, about 2-8 mg, about 2-9 mg, about 2-10 mg, about 2-11 mg, about 2-12 mg, about 2-13 mg, about 2-14 mg, about 2-15 mg, about 2-20 mg, about 2-21 mg, about 2-22 mg, about 2-23 mg, about 2-24 mg, about 2-25 mg, about 2-30 mg, about 2-35 mg, about 2-40 mg, about 2-45 mg, about 2-50 mg, about 2-75 mg, about 2-100 mg, about 1-5 mg, about 5-10 mg, about 10-15 mg, about 15-20 mg, about 20-25 mg, about 20-30 mg, about 25-30 mg, about 30-35 mg, about 35-40 mg, about 40-45 mg, about 40-60 mg, about 45-50 mg, about 50-55 mg, about 55-60 mg, about 60-65 mg, about 65-70 mg, about 70-80 mg, about 80-90 mg, about 80-120 mg, about 90-100 mg, about 100-120 mg, about 120-140 mg, about 140-160 mg, about 160-180 mg, about 180-200 mg, about 10 mg, about 15 mg, about 20 mg, about 30 mg, about 40 mg, about 60 mg, about 100 mg, about 150 mg, of the desvenlafaxine, or any dose in a range bounded by any of these values, may be administered.

For a combination of a duloxetine and a dextromethorphan (including deuterium-modified dextromethorphan, e.g. d6-dextromethorphan, and non-deuterium modified dextromethorphan), a daily dose of about 1-5 mg, about 2-5 mg, about 2-6 mg, about 2-7 mg, about 2-8 mg, about 2-9 mg, about 2-10 mg, about 2-11 mg, about 2-12 mg, about 2-13 mg, about 2-14 mg, about 2-15 mg, about 2-20 mg, about 2-21 mg, about 2-22 mg, about 2-23 mg, about 2-24 mg, about 2-25 mg, about 2-26 mg, about 2-27 mg, about 2-28 mg, about 2-29 mg, about 2-30 mg, about 2-35 mg, about 2-40 mg, about 2-45 mg, about 2-60 mg, about 2-90 mg, about 2-120 mg, about 5-10 mg, about 10-15 mg, about 15-20 mg, about 20-25 mg, about 20-40 mg, about 25-30 mg, about 30-35 mg, about 30-50 mg, about 35-40 mg, about 40-45 mg, about 45-50 mg, about 50-55 mg, about 50-70 mg, about 55-60 mg, about 60-65 mg, about 65-70 mg, about 70-80 mg, about 80-90 mg, about 90-100 mg, about 100-120 mg, about 120-140 mg, about 140-160 mg, about 160-180 mg, about 180-200 mg, about 10 mg, about 15 mg, about 20 mg, about 30 mg, about 40 mg, about 60 mg, about 100 mg, about 120 mg, of the duloxetine, or any dose in a range bounded by any of these values, may be administered.

For a combination of a mirtazapine and a dextromethorphan (including deuterium-modified dextromethorphan, e.g. d6-dextromethorphan, and non-deuterium modified dextromethorphan), a daily dose of about 2-5 mg, about 2-6 mg, about 2-7 mg, about 2-8 mg, about 2-9 mg, about 2-10 mg, about 2-11 mg, about 2-12 mg, about 2-13 mg, about 2-14 mg, about 2-15 mg, about 2-20 mg, about 2-25 mg, about 2-30 mg, about 2-35 mg, about 2-40 mg, about 2-45 mg, about 1-5 mg, about 5-10 mg, about 5-100 mg, about 10-15 mg, about 10-50 mg, about 15-20 mg, about 15-45 mg, about 20-25 mg, about 25-30 mg, about 30-35 mg, about 35-40 mg, about 40-45 mg, about 45-50 mg, about 50-55 mg, about 55-60 mg, about 60-65 mg, about 65-70 mg, about 70-80 mg, about 80-90 mg, about 90-100 mg, about 100-120 mg, about 120-140 mg, about 140-160 mg, about 160-180 mg, about 180-200 mg, about 10 mg, about 15 mg, about 20 mg, about 30 mg, about 40 mg, about 45 mg, about 60 mg, about 75 mg, of the mirtazapine, or any dose in a range bounded by any of these values, may be administered.

For a combination of a nefazodone and a dextromethorphan (including deuterium-modified dextromethorphan, e.g. d6-dextromethorphan, and non-deuterium modified dextromethorphan), a daily dose of about 1-10 mg, about 10-20 mg, about 20-40 mg, about 20-50 mg, about 20-60 mg, about 20-70 mg, about 20-80 mg, about 20-90 mg, about 20-100 mg, about 20-120 mg, about 20-140 mg, about 20-160 mg, about 20-180 mg, about 20-200 mg, about 20-250 mg, about 20-300 mg, about 20-450 mg, about 20-600 mg, about 20-25 mg, about 25-30 mg, about 30-40 mg, about 40-50 mg, about 50-60 mg, about 60-70 mg, about 70-80 mg, about 80-90 mg, about 80-120 mg, about 90-100 mg, about 100-120 mg, about 120-140 mg, about 140-150 mg, about 150-160 mg, about 160-180 mg, about 160-240 mg, about 180-200 mg, about 200-220 mg, about 220-240, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 700-1000 mg, about 1000-1500 mg, about 25 mg, about 50 mg, about 75 mg, about 100 mg, about 150 mg, about 250 mg, about 300 mg, about 400 mg, about 600 mg, of the nefazodone, or any dose in a range bounded by any of these values, may be administered.

For a combination of a selegiline and a dextromethorphan (including deuterium-modified dextromethorphan, e.g. d6-dextromethorphan, and non-deuterium modified dextromethorphan), a daily dose of about 0.5-2 mg, about 2-5 mg, about 1-10 mg, about 1-9 mg, about 1-8 mg, about 1-7 mg, about 1-6 mg, about 1-5 mg, about 1-3 mg, about 3-5 mg, about 5-10 mg, about 5-15 mg, about 10-15 mg, about 15-25 mg, about 25-30 mg, about 30-35 mg, about 35-40 mg, about 40-45 mg, about 45-50 mg, about 5 mg, about 10 mg, about 15 mg, about 20 mg, about 30 mg, about 40 mg, of the selegiline, or any dose in a range bounded by any of these values, may be administered.

For a combination of a sibutramine and a dextromethorphan (including deuterium-modified dextromethorphan, e.g. d6-dextromethorphan, and non-deuterium modified dextromethorphan), a daily dose of about 1-5 mg, about 1-15 mg, about 1-10 mg, about 1-8 mg, about 5-10 mg, about 10-15 mg, about 15-20 mg, about 20-25 mg, about 25-30 mg, about 30-35 mg, about 35-40 mg, about 40-45 mg, about 45-50 mg, about 50-55 mg, about 55-60 mg, about 60-65 mg, about 65-70 mg, about 70-80 mg, about 80-90 mg, about 90-100 mg, about 100-120 mg, about 120-140 mg, about 5 mg, about 10 mg, about 15 mg, about 20 mg, about 30 mg, about 40 mg, about 60 mg, about 100 mg, about 120 mg, of the sibutramine, or any dose in a range bounded by any of these values, may be administered.

For a combination of a rasagiline and a dextromethorphan (including deuterium-modified dextromethorphan, e.g. d6-dextromethorphan, and non-deuterium modified dextromethorphan), a daily dose of about 0.1-0.3 mg, about 0.3-0.5 mg, about 0.3-0.7 mg, about 0.5-0.7 mg, about 0.5-1.5 mg, about 0.7-0.9 mg, about 0.9-1.0 mg, about 1.0-1.5 mg, about 1.5-2.0 mg, about 2.0-3.0 mg, about 0.1 mg, about 0.25 mg, about 0.5 mg, about 0.75 mg, about 1 mg, about 2 mg, of the rasagiline, or any dose in a range bounded by any of these values, may be administered.

For a combination of a milnacipran and a dextromethorphan (including deuterium-modified dextromethorphan, e.g. d6-dextromethorphan, and non-deuterium modified dextromethorphan), a daily dose of about 1-7.5 mg, about 7.5-12.5 mg, about 5-20 mg, about 5-100 mg, about 5-90 mg, about 5-80 mg, about 5-70 mg, about 5-60 mg, about 5-50 mg, about 5-40 mg, about 12.5-15 mg, about 15-20 mg, about 20-30 mg, about 20-25 mg, about 25-30 mg, about 30-35 mg, about 35-40 mg, about 40-45 mg, about 45-50 mg, about 50-55 mg, about 40-60 mg, about 55-60 mg, about 60-65 mg, about 65-70 mg, about 70-80 mg, about 80-90 mg, about 90-100 mg, about 80-120 mg, about 100-120 mg, about 120-140 mg, about 140-160 mg, about 160-180 mg, about 180-200 mg, about 180-220 mg, about 200-300 mg, about 300-400 mg, about 7.5 mg, about 12.5 mg, about 25 mg, about 50 mg, about 75 mg, about 60 mg, about 100 mg, about 200 mg, of the milnacipran, or any dose in a range bounded by any of these values, may be administered.

For a combination of a moclobemide and a dextromethorphan (including deuterium-modified dextromethorphan, e.g. d6-dextromethorphan, and non-deuterium modified dextromethorphan), a daily dose of about 1-10 mg, about 10-20 mg, about 20-25 mg, about 20-450 mg, about 20-300 mg, about 20-250 mg, about 20-200 mg, about 20-150 mg, about 20-100 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240 mg, about 240-250 mg, 250-260 mg, about 260-280 mg, about 280-320 mg, about 280-300 mg, about 300-320 mg, about 320-350 mg, about 350-400 mg, about 430-470 mg, about 400-450 mg, about 450-500 mg, about 500-550 mg, about 550-600 mg, about 600-650 mg, about 650-700 mg, about 25 mg, about 50 mg, about 75 mg, about 100 mg, about 150 mg, about 250 mg, about 300 mg, about 400 mg, about 600 mg, of the moclobemide, or any dose in a range bounded by any of these values, may be administered.

For a combination of a nialamide and a dextromethorphan (including deuterium-modified dextromethorphan, e.g. d6-dextromethorphan, and non-deuterium modified dextromethorphan), a daily dose of about 0.1-0.25 mg, about 0.25-0.5 mg, about 0.5-0.75 mg, about 0.75-1 mg, about 1-5 mg, about 5-10 mg, about 10-15 mg, about 15-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 700-800 mg, about 800-1000 mg, about 25 mg, about 50 mg, about 75 mg, about 100 mg, about 150 mg, about 250 mg, about 300 mg, about 400 mg, about 600 mg, of the nialamide, or any dose in a range bounded by any of these values, may be administered.

For a combination of a iproniazid and a dextromethorphan (including deuterium-modified dextromethorphan, e.g. d6-dextromethorphan, and non-deuterium modified dextromethorphan), a daily dose of about 0.1-0.25 mg, about 0.25-0.5 mg, about 0.5-0.75 mg, about 0.75-1 mg, about 1-5 mg, about 5-10 mg, about 10-15 mg, about 15-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 700-800 mg, about 800-1000 mg, about 25 mg, about 50 mg, about 75 mg, about 100 mg, about 150 mg, about 250 mg, about 300 mg, about 400 mg, about 600 mg, of the iproniazid, or any dose in a range bounded by any of these values, may be administered.

For a combination of a iproclozide and a dextromethorphan (including deuterium-modified dextromethorphan, e.g. d6-dextromethorphan, and non-deuterium modified dextromethorphan), a daily dose of about 0.1-0.25 mg, about 0.25-0.5 mg, about 0.5-0.75 mg, about 0.75-1 mg, about 1-5 mg, about 5-10 mg, about 10-15 mg, about 15-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 700-800 mg, about 800-1000 mg, about 25 mg, about 50 mg, about 75 mg, about 100 mg, about 150 mg, about 250 mg, about 300 mg, about 400 mg, about 600 mg, of the iproclozide, or any dose in a range bounded by any of these values, may be administered.

For a combination of a toloxatone and a dextromethorphan (including deuterium-modified dextromethorphan, e.g. d6-dextromethorphan, and non-deuterium modified dextromethorphan), a daily dose of about 0.1-0.25 mg, about 0.25-0.5 mg, about 0.5-0.75 mg, about 0.75-1 mg, about 1-5 mg, about 5-10 mg, about 10-15 mg, about 15-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 700-800 mg, about 800-1000 mg, about 25 mg, about 50 mg, about 75 mg, about 100 mg, about 150 mg, about 250 mg, about 300 mg, about 400 mg, about 600 mg, of the toloxatone, or any dose in a range bounded by any of these values, may be administered.

For a combination of a butriptyline and a dextromethorphan (including deuterium-modified dextromethorphan, e.g. d6-dextromethorphan, and non-deuterium modified dextromethorphan), a daily dose of about 0.1-0.25 mg, about 0.25-0.5 mg, about 0.5-0.75 mg, about 0.75-1 mg, about 1-5 mg, about 5-10 mg, about 10-15 mg, about 15-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 700-800 mg, about 800-1000 mg, about 25 mg, about 50 mg, about 75 mg, about 100 mg, about 150 mg, about 250 mg, about 300 mg, about 400 mg, about 600 mg, of the butriptyline, or any dose in a range bounded by any of these values, may be administered.

For a combination of a dosulepin and a dextromethorphan (including deuterium-modified dextromethorphan, e.g. d6-dextromethorphan, and non-deuterium modified dextromethorphan), a daily dose of about 0.1-0.25 mg, about 0.25-0.5 mg, about 0.5-0.75 mg, about 0.75-1 mg, about 1-5 mg, about 5-10 mg, about 10-15 mg, about 15-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 700-800 mg, about 800-1000 mg, about 25 mg, about 50 mg, about 75 mg, about 100 mg, about 150 mg, about 250 mg, about 300 mg, about 400 mg, about 600 mg, of the dosulepin, or any dose in a range bounded by any of these values, may be administered.

For a combination of a dibenzepin and a dextromethorphan (including deuterium-modified dextromethorphan, e.g. d6-dextromethorphan, and non-deuterium modified dextromethorphan), a daily dose of about 0.1-0.25 mg, about 0.25-0.5 mg, about 0.5-0.75 mg, about 0.75-1 mg, about 1-5 mg, about 5-10 mg, about 10-15 mg, about 15-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 700-800 mg, about 800-1000 mg, about 25 mg, about 50 mg, about 75 mg, about 100 mg, about 150 mg, about 250 mg, about 300 mg, about 400 mg, about 600 mg, of the dibenzepin, or any dose in a range bounded by any of these values, may be administered.

For a combination of a iprindole and a dextromethorphan (including deuterium-modified dextromethorphan, e.g. d6-dextromethorphan, and non-deuterium modified dextromethorphan), a daily dose of about 0.1-0.25 mg, about 0.25-0.5 mg, about 0.5-0.75 mg, about 0.75-1 mg, about 1-5 mg, about 5-10 mg, about 10-15 mg, about 15-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 700-800 mg, about 800-1000 mg, about 25 mg, about 50 mg, about 75 mg, about 100 mg, about 150 mg, about 250 mg, about 300 mg, about 400 mg, about 600 mg, of the iprindole, or any dose in a range bounded by any of these values, may be administered.

For a combination of a lofepramine and a dextromethorphan (including deuterium-modified dextromethorphan, e.g. d6-dextromethorphan, and non-deuterium modified dextromethorphan), a daily dose of about 0.1-0.25 mg, about 0.25-0.5 mg, about 0.5-0.75 mg, about 0.75-1 mg, about 1-5 mg, about 5-10 mg, about 10-15 mg, about 15-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 700-800 mg, about 800-1000 mg, about 25 mg, about 50 mg, about 75 mg, about 100 mg, about 150 mg, about 250 mg, about 300 mg, about 400 mg, about 600 mg, of the lofepramine, or any dose in a range bounded by any of these values, may be administered.

For a combination of a opipramol and a dextromethorphan (including deuterium-modified dextromethorphan, e.g. d6-dextromethorphan, and non-deuterium modified dextromethorphan), a daily dose of about 0.1-0.25 mg, about 0.25-0.5 mg, about 0.5-0.75 mg, about 0.75-1 mg, about 1-5 mg, about 5-10 mg, about 10-15 mg, about 15-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 700-800 mg, about 800-1000 mg, about 25 mg, about 50 mg, about 75 mg, about 100 mg, about 150 mg, about 250 mg, about 300 mg, about 400 mg, about 600 mg, of the opipramol, or any dose in a range bounded by any of these values, may be administered.

For a combination of a norfluoxetine and a dextromethorphan (including deuterium-modified dextromethorphan, e.g. d6-dextromethorphan, and non-deuterium modified dextromethorphan), a daily dose of about 0.1-0.25 mg, about 0.25-0.5 mg, about 0.5-0.75 mg, about 0.75-1 mg, about 1-5 mg, about 5-10 mg, about 10-15 mg, about 15-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 700-800 mg, about 800-1000 mg, about 25 mg, about 50 mg, about 75 mg, about 100 mg, about 150 mg, about 250 mg, about 300 mg, about 400 mg, about 600 mg, of the norfluoxetine, or any dose in a range bounded by any of these values, may be administered.

For a combination of a dapoxetine and a dextromethorphan (including deuterium-modified dextromethorphan, e.g. d6-dextromethorphan, and non-deuterium modified dextromethorphan), a daily dose of about 0.1-0.25 mg, about 0.25-0.5 mg, about 0.5-0.75 mg, about 0.75-1 mg, about 1-5 mg, about 5-10 mg, about 10-15 mg, about 15-20 mg, about 20-25 mg, about 25-30 mg, about 30-40 mg, about 40-50 mg, about 50-60 mg, about 60-70 mg, about 70-80 mg, about 80-90 mg, about 90-100 mg, about 100-120 mg, about 120-140 mg, about 140-150 mg, about 150-160 mg, about 160-180 mg, about 180-200 mg, about 200-220 mg, about 220-240, about 240-250 mg, about 250-260 mg, about 260-280 mg, about 280-300 mg, about 300-320 mg, about 320-350 mg, about 350-400 mg, about 400-450 mg, about 450-500 mg, about 500-550 mg, about 550-600 mg, about 600-650 mg, about 650-700 mg, about 700-800 mg, about 800-1000 mg, about 25 mg, about 50 mg, about 75 mg, about 100 mg, about 150 mg, about 250 mg, about 300 mg, about 400 mg, about 600 mg, of the dapoxetine, or any dose in a range bounded by any of these values, may be administered.

Bupropion has the structure shown below (bupropion hydrochloride form shown).

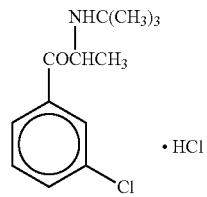

Combining bupropion with dextromethorphan may provide greater efficacy, such as greater pain relief, than would otherwise be achieved by administering either component alone. In extensive metabolizers, dextromethorphan can be rapidly and extensively metabolized, yielding low systemic exposure even at high doses. Bupropion, besides possessing antidepressant and analgesic properties, is an inhibitor of dextromethorphan metabolism. Bupropion is a dopamine and norepinephrine reuptake inhibitor. It can also be a nicotinic acetylcholine receptor antagonist, and it can modulate cytokines associated with inflammatory diseases. Bupropion can affect levels of tumor necrosis factor-alpha and interferon-gamma. Metabolites of bupropion, which include hydroxybupropion, threohydroxybupropion (also known as threohydrobupropion or threodihydrobupropion), and erythrohydroxybupropion (also known as erythrohydrobupropion or erythrodihydrobupropion), are also inhibitors of dextromethorphan metabolism. Thus, bupropion, including a form of bupropion that is rapidly converted in the body (such as a salt, hydrate, solvate, polymorph, etc.), is a prodrug of hydroxybupropion, threohydroxybupropion, and erythrohydroxybupropion. Prodrugs of bupropion can include N-methylbupropion and N-benzylbupropion.

As explained above, this inhibition may augment dextromethorphan plasma levels, resulting in additive or synergistic efficacy such as relief of neurological disorders including pain, depression, smoking cessation, etc. Thus, while inhibition of dextromethorphan metabolism is only one of many potential benefits of the combination, co-administration of dextromethorphan with bupropion may thereby enhance the efficacy of bupropion for many individuals. Co-administration of dextromethorphan with bupropion may enhance the analgesic properties of bupropion for many individuals. Co-administration of dextromethorphan with bupropion may also enhance the antidepressant properties of bupropion for many individuals, including faster onset of action.

Another potential benefit of co-administration of dextromethorphan and bupropion is that it may be useful to reduce the potential for an adverse event, such as somnolence, associated with treatment by dextromethorphan. This may be useful, for example, in human patients at risk of experiencing the adverse event as a result of being treated with dextromethorphan.

Another potential benefit of co-administration of dextromethorphan and bupropion is that it may be useful to reduce the potential for an adverse event, such as seizure, associated with treatment by bupropion, hydroxybupropion, erythrohydroxybupropion, threohydroxybupropion, or a metabolite or prodrug of any of these compounds. This may be useful, for example, in human patients at risk of experiencing the adverse event as a result of being treated with bupropion, hydroxybupropion, erythrohydroxybupropion, threohydroxybupropion, or a metabolite or prodrug of any of these compounds.

With respect to dextromethorphan, bupropion, hydroxybupropion, erythrohydroxybupropion, threohydroxybupropion, or a metabolite or prodrug of any of these compounds, co-administration may reduce a central nervous system adverse event, a gastrointestinal event, or another type of adverse event associated with any of these compounds. Central nervous system (CNS) adverse events include, but are not limited to, nervousness, dizziness, sleeplessness, light-headedness, tremor, hallucinations, convulsions, CNS depression, fear, anxiety, headache, increased irritability or excitement, tinnitus, drowsiness, dizziness, sedation, somnolence, confusion, disorientation, lassitude, incoordination, fatigue, euphoria, nervousness, insomnia, sleeping disturbances, convulsive seizures, excitation, catatonic-like states, hysteria, hallucinations, delusions, paranoia, headaches and/or migraine, and extrapyramidal symptoms such as oculogyric crisis, torticollis, hyperexcitability, increased muscle tone, ataxia, and/or tongue protrusion.

Gastrointestinal adverse events include, but are not limited to, nausea, vomiting, abdominal pain, dysphagia, dyspepsia, diarrhea, abdominal distension, flatulence, peptic ulcers with bleeding, loose stools, constipation, stomach pain, heartburn, gas, loss of appetite, feeling of fullness in stomach, indigestion, bloating, hyperacidity, dry mouth, gastrointestinal disturbances, and gastric pain.

Co-administering dextromethorphan and an antidepressant, such as bupropion, hydroxybupropion, erythrohydroxybupropion, threohydroxybupropion, or a metabolite or prodrug of any of these compounds, does not necessarily require that the two compounds be administered in the same dosage form. For example, the two compounds may be administered in a single dosage form, or they may be administered in two separate dosage forms. Additionally, the two compounds may be administered at the same time, but this is not required. The compounds can be given at different times as long as both are in a human body at the same time for at least a portion of the time that treatment by co-administration is being carried out.

Side effects of bupropion, hydroxybupropion, erythrohydroxybupropion, threohydroxybupropion, and/or dextromethorphan may be reduced by administering bupropion, hydroxybupropion, erythrohydroxybupropion, or threohydroxybupropion, with dextromethorphan. Examples of side effects that may be reduced include abnormal sensation of rotation and movement, agitation, arm weakness, bloating, blurred vision, burning sensation in the eyes, buzzing sound in ear, changes in vital signs (including, but not limited to, heart rate, respiratory rate, body temperature, blood pressure), cold sensation, constipation, difficulty concentrating, difficulty sleeping, difficulty in falling asleep, difficulty urinating, difficulty with bowel movement, discomfort in the ear, discomfort in the eye, discomfort in the stomach, dizziness, dry lips, dry mouth, dry throat, dysmenorrhea, fatigue, feeling feverish, feeling heavy headed, feeling more agitated than usual, feeling more tired than usual, feeling tired, hand tremors, hand weakness, headache, heartburn, hot flashes, increased blood pressure, increased skin sensitivity, increased skin sensitivity at head and face, involuntary muscle contraction, involuntary muscle contractions at all over the body, knee pain, leg weakness, lightheadedness, loose stool, loss of appetite, low back pain, menstrual disorder, metallic taste, more saliva than usual, mucosal dryness, nasal congestion, nausea, runny nose, sensation of light pressure sensation in the eyes, shivers when stretching or yawning, skin sensitivity, skin sensitivity in arm, face, and/or head, sleep difficulties, soft stools, stomach ache, stomach discomfort, sweaty hands and/or feet, throat irritation, throat pain, tinnitus, tremors, and/or weakness. Any of these side effects may also be referred to, or grouped, according to a corresponding, equivalent, or otherwise relevant term found in the Medical Dictionary for Regulatory Activities (MedRA).

In some embodiments, co-administration of a combination of bupropion, hydroxybupropion, erythrohydroxybupropion, threohydroxybupropion, or a metabolite or prodrug of any of these compounds, and dextromethorphan results in both bupropion, hydroxybupropion, erythrohydroxybupropion, threohydroxybupropion, or a metabolite or prodrug of any of these compounds, and dextromethorphan contributing to the pain relieving properties of the combination. For example, the combination may have improved pain relieving properties as compared to bupropion, hydroxybupropion, erythrohydroxybupropion, threohydroxybupropion, or a metabolite or prodrug of any of these compounds, alone or compared to dextromethorphan alone, including potentially faster onset of action.

In some embodiments, the combination may have improved pain relieving properties of at least about 0.5%, at least about 1%, at least about 10%, at least about 20%, at least about 30%, at least about 50%, at least 100%, up to about 500% or up to 1000%, about 0.5% to about 1000%, about 10% to about 20%, about 20% to about 30%, about 30% to about 40%, about 40% to about 50%, about 50% to about 60%, about 60% to about 70%, about 70% to about 80%, about 80% to about 90%, about 90% to about 100%, about 100% to about 110%, about 110% to about 120%, about 120% to about 130%, about 130% to about 140%, about 140% to about 150%, about 150% to about 160%, about 160% to about 170%, about 170% to about 180%, about 180% to about 190%, about 190% to about 200%, or any amount of pain relief in a range bounded by, or between, any of these values, as compared to bupropion, hydroxybupropion, erythrohydroxybupropion, threohydroxybupropion, or a metabolite or prodrug of any of these compounds, alone.

In some embodiments, the combination may have improved pain relieving properties of at least about 0.5%, at least about 1%, at least about 10%, at least about 20%, at least about 30%, at least about 50%, at least 100%, up to about 500% or up to 1000%, about 0.5% to about 1000%, about 10% to about 20%, about 20% to about 30%, about 30% to about 40%, about 40% to about 50%, about 50% to about 60%, about 60% to about 70%, about 70% to about 80%, about 80% to about 90%, about 90% to about 100%, about 100% to about 110%, about 110% to about 120%, about 120% to about 130%, about 130% to about 140%, about 140% to about 150%, about 150% to about 160%, about 160% to about 170%, about 170% to about 180%, about 180% to about 190%, about 190% to about 200%, or any amount of pain relief in a range bounded by, or between, any of these values, as compared to as compared to dextromethorphan alone.

Unless otherwise indicated, any reference to a compound herein, such as dextromethorphan, bupropion, hydroxybupropion, erythrohydroxybupropion, threohydroxybupropion, by structure, name, or any other means, includes pharmaceutically acceptable salts; alternate solid forms, such as polymorphs, solvates, hydrates, etc.; tautomers; deuterium-modified compounds, such as deuterium modified dextromethorphan; or any chemical species that may rapidly convert to a compound described herein under conditions in which the compounds are used as described herein.

In some embodiments, an excess of one stereoisomer of bupropion, hydroxybupropion, erythrohydroxybupropion, threohydroxybupropion, or a metabolite or prodrug of any of these compounds may be administered. In other embodiments, an excess of the S-enantiomer (such as at least 60%, at least 70%, at least 75%, at least 80%, at least 85%, at least 90%, at least 95%, at least 99% or enantiomerically pure S-enantiomer) or an excess of the R-enantiomer (such as at least 60%, at least 70%, at least 75%, at least 80%, at least 85%, at least 90%, at least 95%, at least 99% or enantiomerically pure R-enantiomer) of bupropion, hydroxybupropion, erythrohydroxybupropion, threohydroxybupropion, or a metabolite or prodrug of any of these compounds may be administered.
Examples of deuterium-enriched bupropion, and/or enantiopure deuterium-enriched bupropion include, but are not limited to, those shown below.
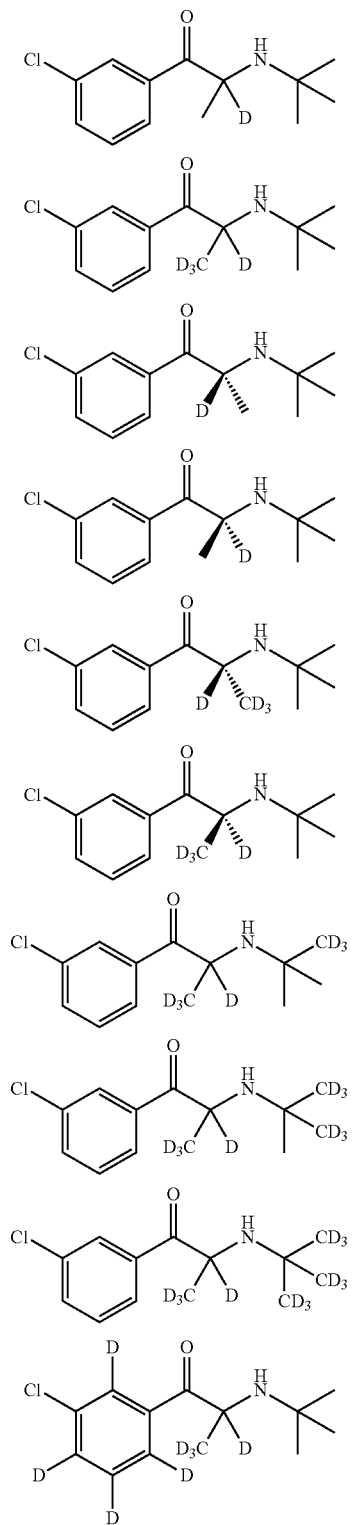
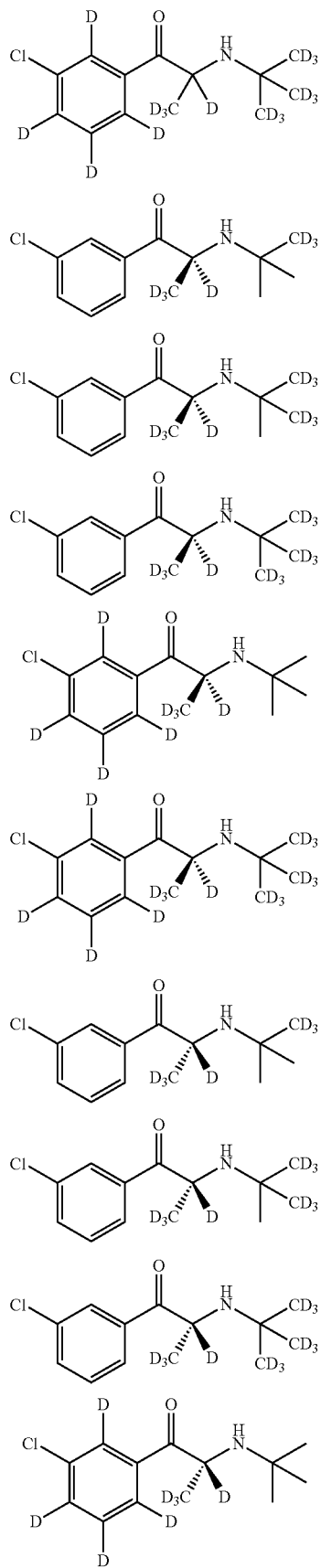

-continued

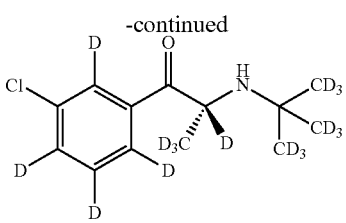

In some embodiments, both dextromethorphan and bupropion, hydroxybupropion, erythrohydroxybupropion, threohydroxybupropion, a metabolite, or prodrug of any of these compounds are formulated to be immediate release, and in other embodiments both bupropion, hydroxybupropion, erythrohydroxybupropion, threohydroxybupropion, a metabolite or prodrug of any of these compounds are formulated to be sustained release.

Examples of deuterium modified dextromethorphan include, but are not limited to, those shown below.

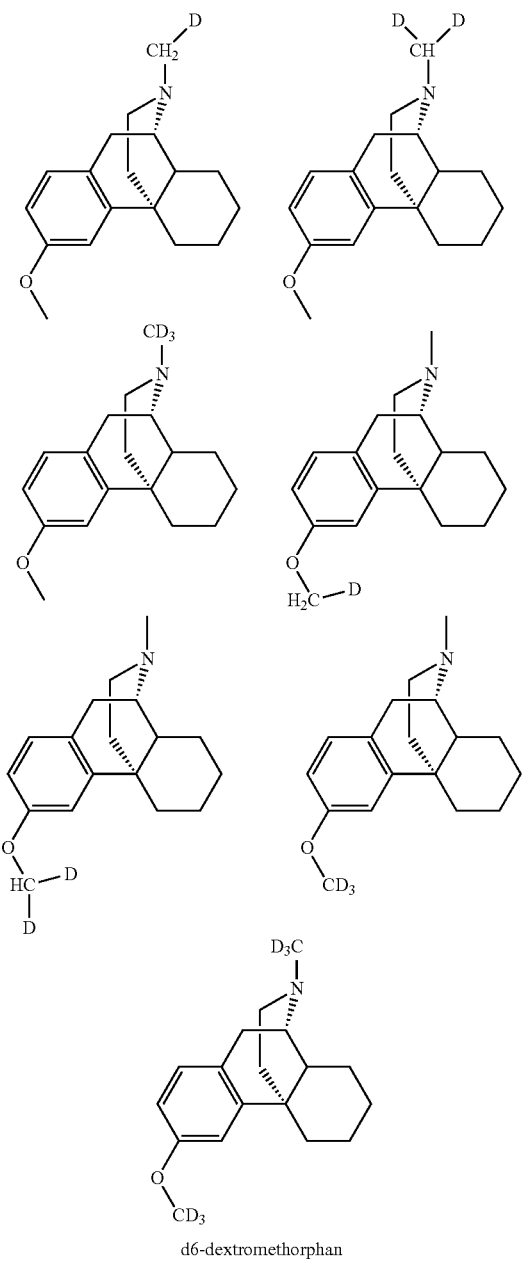

d6-dextromethorphan

A dosage form or a composition may be a blend or mixture of dextromethorphan and a compound that inhibits the metabolism of dextromethorphan, such as bupropion, hydroxybupropion, erythrohydroxybupropion, threohydroxybupropion, or a metabolite or prodrug of any of these compounds, either alone or within a vehicle. For example, dextromethorphan and bupropion may be dispersed within each other or dispersed together within a vehicle. A dispersion may include a mixture of solid materials wherein small individual particles are substantially one compound, but the small particles are dispersed within one another, such as might occur if two powders of two different drugs are blended with a solid vehicle material, and the blending is done in the solid form. In some embodiments, dextromethorphan and bupropion may be substantially uniformly dispersed within a composition or dosage form. Alternatively, dextromethorphan and bupropion may be in separate domains or phases within a composition or dosage form. For example, one drug may be in a coating and another drug may be in a core within the coating. For example, one drug may be formulated for sustained release and another drug may be formulated for immediate release.

Some embodiments include administration of a tablet that contains bupropion in a form that provides sustained release and dextromethorphan in a form that provides immediate release. While there are many ways that sustained release of bupropion may be achieved, in some embodiments bupropion is combined with hydroxypropyl methylcellulose. For example, particles of bupropion hydrochloride could be blended with microcrystalline cellulose and hydroxypropyl methylcellulose (e.g., METHOCEL®) to form an admixture of blended powders. This could then be combined with immediate release dextromethorphan in a single tablet.

Dextromethorphan and/or an antidepressant, such as bupropion, hydroxybupropion, threohydroxybupropion and erythrohydroxybupropion, or a non-bupropion antidepressant (all of which are referred to collectively herein as "therapeutic compounds" for convenience) may be combined with a pharmaceutical carrier selected on the basis of the chosen route of administration and standard pharmaceutical practice as described, for example, in Remington's Pharmaceutical Sciences, 2005. The relative proportions of active ingredient and carrier may be determined, for example, by the solubility and chemical nature of the compounds, chosen route of administration and standard pharmaceutical practice.

Therapeutic compounds may be administered by any means that may result in the contact of the active agent(s) with the desired site or site(s) of action in the body of a patient. The compounds may be administered by any conventional means available for use in conjunction with pharmaceuticals, either as individual therapeutic agents or in a combination of therapeutic agents. For example, they may be administered as the sole active agents in a pharmaceutical composition, or they can be used in combination with other therapeutically active ingredients.

Therapeutic compounds may be administered to a human patient in a variety of forms adapted to the chosen route of administration, e.g., orally or parenterally. Parenteral administration in this respect includes administration by the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation, aerosol and rectal systemic.

The ratio of dextromethorphan to bupropion may vary. In some embodiments, the weight ratio of dextromethorphan to bupropion may be about 0.1 to about 10, about 0.1 to about 2, about 0.2 to about 1, about 0.1 to about 0.5, about 0.1 to about 0.3, about 0.2 to about 0.4, about 0.3 to about 0.5, about 0.5 to about 0.7, about 0.8 to about 1, about 0.2, about 0.3, about 0.4, about 0.45, about 0.6, about 0.9, or any ratio in a range bounded by, or between, any of these values. A ratio of 0.1 indicates that the weight of dextromethorphan is 1/10 that of bupropion. A ratio of 10 indicates that the weight of dextromethorphan is 10 times that of bupropion.

The amount of dextromethorphan in a therapeutic composition may vary. For example, some liquid compositions may comprise about 0.0001% (w/v) to about 50% (w/v), about 0.01% (w/v) to about 20% (w/v), about 0.01% to about 10% (w/v), about 0.001% (w/v) to about 1% (w/v), about 0.1% (w/v) to about 0.5% (w/v), about 1% (w/v) to about 3% (w/v), about 3% (w/v) to about 5% (w/v), about 5% (w/v) to about 7% (w/v), about 7% (w/v) to about 10% (w/v), about 10% (w/v) to about 15% (w/v), about 15% (w/v) to about 20% (w/v), about 20% (w/v) to about 30% (w/v), about 30% (w/v) to about 40% (w/v), or about 40% (w/v) to about 50% (w/v) of dextromethorphan.

Some liquid dosage forms may contain about 10 mg to about 500 mg, about 30 mg to about 350 mg, about 50 mg to about 200 mg, about 50 mg to about 70 mg, about 20 mg to about 50 mg, about 30 mg to about 60 mg, about 40 mg to about 50 mg, about 40 mg to about 42 mg, about 42 mg to about 44 mg, about 44 mg to about 46 mg, about 46 mg to about 48 mg, about 48 mg to about 50 mg, about 80 mg to about 100 mg, about 110 mg to about 130 mg, about 170 mg to about 190 mg, about 45 mg, about 60 mg, about 90 mg, about 120 mg, or about 180 mg of dextromethorphan, or any amount of dextromethorphan in a range bounded by, or between, any of these values.

Some solid compositions may comprise at least about 5% (w/w), at least about 10% (w/w), at least about 20% (w/w), at least about 50% (w/w), at least about 70% (w/w), at least about 80%, about 10% (w/w) to about 30% (w/w), about 10% (w/w) to about 20% (w/w), about 20% (w/w) to about 30% (w/w), about 30% (w/w) to about 50% (w/w), about 30% (w/w) to about 40% (w/w), about 40% (w/w) to about 50% (w/w), about 50% (w/w) to about 80% (w/w), about 50% (w/w) to about 60% (w/w), about 70% (w/w) to about 80% (w/w), or about 80% (w/w) to about 90% (w/w) of dextromethorphan.

Some solid dosage forms may contain about 10 mg to about 500 mg, about 30 mg to about 350 mg, about 20 mg to about 50 mg, about 30 mg to about 60 mg, about 40 mg to about 50 mg, about 40 mg to about 42 mg, about 42 mg to about 44 mg, about 44 mg to about 46 mg, about 46 mg to about 48 mg, about 48 mg to about 50 mg, about 50 mg to about 200 mg, about 50 mg to about 70 mg, about 80 mg to about 100 mg, about 110 mg to about 130 mg, about 170 mg to about 190 mg, about 60 mg, about 90 mg, about 120 mg, or about 180 mg of dextromethorphan, or any amount of dextromethorphan in a range bounded by, or between, any of these values.

The amount of bupropion, hydroxybupropion, erythrohydroxybupropion, threohydroxybupropion, or a metabolite or prodrug of any of these compounds, in a therapeutic composition may vary. If increasing the plasma level of dextromethorphan is desired, bupropion, hydroxybupropion, erythrohydroxybupropion, threohydroxybupropion, or a metabolite or prodrug of any of these compounds, should be administered in an amount that increases the plasma level of dextromethorphan. For example, bupropion, hydroxybupropion, erythrohydroxybupropion, threohydroxybupropion, or a metabolite or prodrug of any of these compounds, may be administered in an amount that results in a plasma concentration of dextromethorphan in the human being, on day 8, day 9, or day 10, that is at least about 2 times, at least about 5 times, at least about 10 times, at least about 15 times, at least about 20 times, at least about 30 times, at least about 40 times, at least about 50 times, at least about 60 times, at least about 70 times, or at least about 80 times, the plasma concentration of the same amount of dextromethorphan administered without bupropion, hydroxybupropion, erythrohydroxybupropion, threohydroxybupropion, or a metabolite or prodrug of any of these compounds.

In some embodiments, bupropion, hydroxybupropion, erythrohydroxybupropion, threohydroxybupropion, or a metabolite or prodrug of any of these compounds, may administered to a human being in an amount that results in a 12 hour area under the curve from the time of dosing ($AUC_{0-12}$), or average plasma concentration in the human being for the 12 hours following dosing ($C_{avg}$) of dextromethorphan, on day 8, day 9, or day 10, that is at least about 2 times, at least about 5 times, at least about 10 times, at least about 15 times, at least about 20 times, at least about 30 times, at least about 40 times, at least about 50 times, at least about 60 times, at least about 70 times, or at least about 80 times the plasma concentration of the same amount of dextromethorphan administered without bupropion, hydroxybupropion, erythrohydroxybupropion, threohydroxybupropion, or a metabolite or prodrug of any of these compounds.

In some embodiments, bupropion, hydroxybupropion, erythrohydroxybupropion, threohydroxybupropion, or a metabolite or prodrug of any of these compounds, may administered to a human being in an amount that results in a maximum plasma concentration ($C_{max}$) of dextromethorphan in the human being, on day 8, day 9, or day 10, that is at least about 2 times, at least about 5 times, at least about 10 times, at least about 15 times, at least about 20 times, at least about 30 times, or at least about 40 times the plasma concentration of the same amount of dextromethorphan administered without bupropion, hydroxybupropion, erythrohydroxybupropion, threohydroxybupropion, or a metabolite or prodrug of any of these compounds.

For co-administration of bupropion, hydroxybupropion, threohydroxybupropion, erythrohydroxybupropion, or a metabolite or prodrug of any of these compounds, an increase in the dextromethorphan plasma level can occur on the first day that bupropion, hydroxybupropion, threohydroxybupropion, erythrohydroxybupropion, or a metabolite or prodrug of any of these compounds, is administered, as compared to the same amount of dextromethorphan administered without bupropion, hydroxybupropion, threohydroxybupropion, erythrohydroxybupropion, or a metabolite or prodrug of any of these compounds. For example, the dextromethorphan plasma level on the first day that bupropion, hydroxybupropion, threohydroxybupropion, erythrohydroxybupropion, or a metabolite or prodrug of any of these compounds, is administered may be at least about 1.5 times, at least about at least 2 times, at least about 2.5 times, at least about 3 times, at least about 4 times, at least about 5 times, at least about 6 times at least about 7 times, at least about 8 times, at least about 9 times, or at least about 10 times the level that would be achieved by administering the same amount of dextromethorphan without bupropion, hydroxybupropion, threohydroxybupropion, erythrohydroxybupropion, or a metabolite or prodrug of any of these compounds.

In some embodiments, the dextromethorphan AUC on the first day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least twice the AUC that would be achieved by administering the same amount of dextromethorphan without bupropion, hydroxybupropion, threohydroxybupropion, erythrohydroxybupropion, or a metabolite or prodrug of any of these compounds.

In some embodiments, the dextromethorphan $AUC_{0-12}$ on the first day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 15 ng·hr/mL, at least about 17 ng·hr/mL, at least about 19 ng·hr/mL, at least about 20 ng·hr/mL, at least about 22 ng·hr/mL, at least about 23 ng·hr/mL, at least about 24 ng·hr/mL, at least about 25 ng·hr/mL, at least about 26 ng·hr/mL, at least about 27 ng·hr/mL, at least about 28 ng·hr/mL, at least about 29 ng·hr/mL, at least about 30 ng·hr/mL, at least about 31 ng·hr/mL, at least about 32 ng·hr/mL, at least about 33 ng·hr/mL, at least about 34 ng·hr/mL, at least about 35 ng·hr/mL, at least about 36 ng·hr/mL, at least about 37 ng·hr/mL, at least about 38 ng·hr/mL, at least about 39 ng·hr/mL, at least about 40 ng·hr/mL, at least about 41 ng·hr/mL, at least about 42 ng·hr/mL, at least about 43 ng·hr/mL, at least about 44 ng·hr/mL, at least about 45 ng·hr/mL, at least about 46 ng·hr/mL, at least about 47 ng·hr/mL, at least about 48 ng·hr/mL, at least about 49 ng·hr/mL, at least about 50 ng·hr/mL, at least about 51 ng·hr/mL, at least about 52 ng·hr/mL, at least about 53 ng·hr/mL, at least about 54 ng·hr/mL, at least about 55 ng·hr/mL, at least about 56 ng·hr/mL, at least about or 56.7 ng·hr/mL, and may be up to 10,000 ng·hr/mL.

In some embodiments, the dextromethorphan $AUC_{0-12}$ on the eighth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 40 ng·hr/mL, at least about 50 ng·hr/mL, at least about 60 ng·hr/mL, at least about 70 ng·hr/mL, at least about 80 ng·hr/mL, at least about 90 ng·hr/mL, at least about 100 ng·hr/mL, at least about 150 ng·hr/mL, at least about 200 ng·hr/mL, at least about 250 ng·hr/mL, at least about 300 ng·hr/mL, at least about 350 ng·hr/mL, at least about 400 ng·hr/mL, at least about 450 ng·hr/mL, at least about 500 ng·hr/mL, at least about 550 ng·hr/mL, about 500 ng·hr/mL to about 600 ng·hr/mL, about 500 ng·hr/mL to about 550 ng·hr/mL, about 500 ng·hr/mL to about 525 ng·hr/mL, about 525 ng·hr/mL to about 600 ng·hr/mL, at least about 600 ng·hr/mL, at least about 650 ng·hr/mL, at least about 700 ng·hr/mL, at least about 750 ng·hr/mL, at least about 800 ng·hr/mL, about 800 ng·hr/mL to about 900 ng·hr/mL, about 850 ng·hr/mL to about 900 ng·hr/mL, about 850 ng·hr/mL to about 875 ng·hr/mL, about 875 ng·hr/mL to about 900 ng·hr/mL, about 900 ng·hr/mL to about 1,000 ng·hr/mL, about 1,000 ng·hr/mL to about 1,100 ng·hr/mL, about 1,100 ng·hr/mL to about 1,200 ng·hr/mL, about 1,200 ng·hr/mL to about 1,300 ng·hr/mL, about 1,300 ng·hr/mL to about 1,400 ng·hr/mL, about 1,400 ng·hr/mL to about 1,500 ng·hr/mL, about 1,500 ng·hr/mL to about 1,600 ng·hr/mL, about 1,600 ng·hr/mL to about 1,700 ng·hr/mL, about 1,700 ng·hr/mL to about 1,800 ng·hr/mL, about 1,800 ng·hr/mL to about 2,000 ng·hr/mL, at least about 850 ng·hr/mL, at least about 900 ng·hr/mL, at least about 950 ng·hr/mL, at least about 1000 ng·hr/mL, at least about 1050 ng·hr/mL, at least about 1100 ng·hr/mL, at least about 1150 ng·hr/mL, at least about 1200 ng·hr/mL, at least about 1250 ng·hr/mL, at least about 1300 ng·hr/mL, at least about 1350 ng·hr/mL, at least about 1400 ng·hr/mL, at least about 1450 ng·hr/mL, at least about 1500 ng·hr/mL, at least about 1550 ng·hr/mL, at least about 1600 ng·hr/mL, at least about 1625 ng·hr/mL, at least about 1650 ng·hr/mL, at least about 1675 ng·hr/mL, or at least about 1686.3 ng·hr/mL, and, in some embodiments, may be up to about 50,000 ng·hr/mL.

In some embodiments, the dextromethorphan $AUC_{0-24}$ on the eighth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 50 ng·hr/mL, at least about 75 ng·hr/mL, at least about 100 ng·hr/mL, at least about 200 ng·hr/mL, at least about 300 ng·hr/mL, at least about 400 ng·hr/mL, at least about 500 ng·hr/mL, at least about 600 ng·hr/mL, at least about 700 ng·hr/mL, at least about 800 ng·hr/mL, at least about 900 ng·hr/mL, at least about 1000 ng·hr/mL, at least about 1100 ng·hr/mL, at least about 1200 ng·hr/mL, at least about 1300 ng·hr/mL, at least about 1400 ng·hr/mL, at least about 1500 ng·hr/mL, at least about 1600 ng·hr/mL, at least about 1700 ng·hr/mL, at least about 1800 ng·hr/mL, at least about 1900 ng·hr/mL, at least about 2000 ng·hr/mL, at least about 2100 ng·hr/mL, at least about 2200 ng·hr/mL, at least about 2300 ng·hr/mL, at least about 2400 ng·hr/mL, at least about 2500 ng·hr/mL, at least about 2600 ng·hr/mL, at least about 2700 ng·hr/mL, at least about 2800 ng·hr/mL, at least about 1850 ng·hr/mL, at least about 2900 ng·hr/mL, at least about 2950 ng·hr/mL, or at least about 2975.3 ng·hr/mL, and, in some embodiments, may be up to about 100,000 ng·hr/mL.

In some embodiments, the dextromethorphan $AUC_{0-inf}$ on the eighth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 75 ng·hr/mL, at least about 100 ng·hr/mL, at least about 200 ng·hr/mL, at least about 300 ng·hr/mL, at least about 400 ng·hr/mL, at least about 500 ng·hr/mL, at least about 600 ng·hr/mL, at least about 700 ng·hr/mL, at least about 800 ng·hr/mL, at least about 900 ng·hr/mL, at least about 1000 ng·hr/mL, at least about 1100 ng·hr/mL, at least about 1200 ng·hr/mL, at least about 1300 ng·hr/mL, at least about 1400 ng·hr/mL, at least about 1500 ng·hr/mL, at least about 1600 ng·hr/mL, at least about 1700 ng·hr/mL, at least about 1800 ng·hr/mL, at least about 1900 ng·hr/mL, at least about 2000 ng·hr/mL, at least about 2100 ng·hr/mL, at least about 2200 ng·hr/mL, at least about 2300 ng·hr/mL, at least about 2400 ng·hr/mL, at least about 2500 ng·hr/mL, at least about 2600 ng·hr/mL, at least about 2700 ng·hr/mL, at least about 2800 ng·hr/mL, at least about 2900 ng·hr/mL, at least about 3000 ng·hr/mL, at least about 3100 ng·hr/mL, at least about 3200 ng·hr/mL, at least about 3300 ng·hr/mL, at least about 3400 ng·hr/mL, at least about 3500 ng·hr/mL, at least about 3600 ng·hr/mL, at least about 3700 ng·hr/mL, at least about 3800 ng·hr/mL, at least about 3900 ng·hr/mL, at least about 4000 ng·hr/mL, at least about 4100 ng·hr/mL, at least about 4200 ng·hr/mL, at least about 4300 ng·hr/mL, at least about 4400 ng·hr/mL, at least about 4500 ng·hr/mL, at least about 4600 ng·hr/mL, at least about 4700 ng·hr/mL, at least about 4800 ng·hr/mL, at least about 4900 ng·hr/mL, at least about 5000 ng·hr/mL, at least about 5100 ng·hr/mL, at least about 5200 ng·hr/mL, at least about 5300 ng·hr/mL, at least about 5400 ng·hr/mL, at least about 5500 ng·hr/mL, at least about 5600 ng·hr/mL, at least about 5700 ng·hr/mL, at least about 5800 ng·hr/mL, at least about 5900 ng·hr/mL, at least about 6000 ng·hr/mL, at least about 6100 ng·hr/mL, at least about 6200 ng·hr/mL, at least about 6300 ng·hr/mL, at least about 6400 ng·hr/mL, at least about 6500 ng·hr/mL, at least about 6600 ng·hr/mL, at least about 6700 ng·hr/mL, at least about 6800 ng·hr/mL, at least about 6900 ng·hr/mL, at least about 7000 ng·hr/mL, at least about 7100 ng·hr/mL, at least about 7150 ng·hr/mL, at least about 7200 ng·hr/mL, or at least about 7237.3 ng·hr/mL, and, in some embodiments, may be up to about 100,000 ng·hr/mL.

In some embodiments, the dextromethorphan $AUC_{0-12}$ on the ninth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 40 ng·hr/mL, at least about 50 ng·hr/mL, at least about 60 ng·hr/mL, at least about 70 ng·hr/mL, at least about 80 ng·hr/mL, at least about 90 ng·hr/mL, at least about 100 ng·hr/mL, at least about 150 ng·hr/mL, at least about 200 ng·hr/mL, at least about 250 ng·hr/mL, at least about 300 ng·hr/mL, at least about 350 ng·hr/mL, at least about 400 ng·hr/mL, at least about 450 ng·hr/mL, at least about 500 ng·hr/mL, at least about 550 ng·hr/mL, about 500 ng·hr/mL to about 600 ng·hr/mL, about 500 ng·hr/mL to about 550 ng·hr/mL, about 500 ng·hr/mL to about 525 ng·hr/mL, about 525 ng·hr/mL to about 600 ng·hr/mL, at least about 600 ng·hr/mL, at least about 650 ng·hr/mL, at least about 700 ng·hr/mL, at least about 750 ng·hr/mL, at least about 800 ng·hr/mL, about 800 ng·hr/mL to about 900 ng·hr/mL, about 850 ng·hr/mL to about 900 ng·hr/mL, about 850 ng·hr/mL to about 875 ng·hr/mL, about 875 ng·hr/mL to about 900 ng·hr/mL, about 900 ng·hr/mL to about 1,000 ng·hr/mL, about 1,000 ng·hr/mL to about 1,100 ng·hr/mL, about 1,100 ng·hr/mL to about 1,200 ng·hr/mL, about 1,200 ng·hr/mL to about 1,300 ng·hr/mL, about 1,300 ng·hr/mL to about 1,400 ng·hr/mL, about 1,400 ng·hr/mL to about 1,500 ng·hr/mL, about 1,500 ng·hr/mL to about 1,600 ng·hr/mL, about 1,600 ng·hr/mL to about 1,700 ng·hr/mL, about 1,700 ng·hr/mL to about 1,800 ng·hr/mL, about 1,800 ng·hr/mL to about 2,000 ng·hr/mL, at least about 850 ng·hr/mL, at least about 900 ng·hr/mL, at least about 950 ng·hr/mL, at least about 1000 ng·hr/mL, at least about 1050 ng·hr/mL, at least about 1100 ng·hr/mL, at least about 1150 ng·hr/mL, at least about 1200 ng·hr/mL, at least about 1250 ng·hr/mL, at least about 1300 ng·hr/mL, at least about 1350 ng·hr/mL, at least about 1400 ng·hr/mL, at least about 1450 ng·hr/mL, at least about 1500 ng·hr/mL, at least about 1550 ng·hr/mL, at least about 1600 ng·hr/mL, at least about 1625 ng·hr/mL, at least about 1650 ng·hr/mL, at least about 1675 ng·hr/mL, or at least about 1686.3 ng·hr/mL, and, in some embodiments, may be up to about 50,000 ng·hr/mL.

In some embodiments, the dextromethorphan $AUC_{0-24}$ on the ninth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 50 ng·hr/mL, at least about 75 ng·hr/mL, at least about 100 ng·hr/mL, at least about 200 ng·hr/mL, at least about 300 ng·hr/mL, at least about 400 ng·hr/mL, at least about 500 ng·hr/mL, at least about 600 ng·hr/mL, at least about 700 ng·hr/mL, at least about 800 ng·hr/mL, at least about 900 ng·hr/mL, at least about 1000 ng·hr/mL, at least about 1100 ng·hr/mL, at least about 1200 ng·hr/mL, at least about 1300 ng·hr/mL, at least about 1400 ng·hr/mL, at least about 1500 ng·hr/mL, at least about 1600 ng·hr/mL, at least about 1700 ng·hr/mL, at least about 1800 ng·hr/mL, at least about 1900 ng·hr/mL, at least about 2000 ng·hr/mL, at least about 2100 ng·hr/mL, at least about 2200 ng·hr/mL, at least about 2300 ng·hr/mL, at least about 2400 ng·hr/mL, at least about 2500 ng·hr/mL, at least about 2600 ng·hr/mL, at least about 2700 ng·hr/mL, at least about 2800 ng·hr/mL, at least about 1850 ng·hr/mL, at least about 2900 ng·hr/mL, at least about 2950 ng·hr/mL, or at least about 2975.3 ng·hr/mL, and, in some embodiments, may be up to about 100,000 ng·hr/mL.

In some embodiments, the dextromethorphan $AUC_{0-inf}$ on the ninth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 75 ng·hr/mL, at least about 100 ng·hr/mL, at least about 200 ng·hr/mL, at least about 300 ng·hr/mL, at least about 400 ng·hr/mL, at least about 500 ng·hr/mL, at least about 600 ng·hr/mL, at least about 700 ng·hr/mL, at least about 800 ng·hr/mL, at least about 900 ng·hr/mL, at least about 1000 ng·hr/mL, at least about 1100 ng·hr/mL, at least about 1200 ng·hr/mL, at least about 1300 ng·hr/mL, at least about 1400 ng·hr/mL, at least about 1500 ng·hr/mL, at least about 1600 ng·hr/mL, at least about 1700 ng·hr/mL, at least about 1800 ng·hr/mL, at least about 1900 ng·hr/mL, at least about 2000 ng·hr/mL, at least about 2100 ng·hr/mL, at least about 2200 ng·hr/mL, at least about 2300 ng·hr/mL, at least about 2400 ng·hr/mL, at least about 2500 ng·hr/mL, at least about 2600 ng·hr/mL, at least about 2700 ng·hr/mL, at least about 2800 ng·hr/mL, at least about 2900 ng·hr/mL, at least about 3000 ng·hr/mL, at least about 3100 ng·hr/mL, at least about 3200 ng·hr/mL, at least about 3300 ng·hr/mL, at least about 3400 ng·hr/mL, at least about 3500 ng·hr/mL, at least about 3600 ng·hr/mL, at least about 3700 ng·hr/mL, at least about 3800 ng·hr/mL, at least about 3900 ng·hr/mL, at least about 4000 ng·hr/mL, at least about 4100 ng·hr/mL, at least about 4200 ng·hr/mL, at least about 4300 ng·hr/mL, at least about 4400 ng·hr/mL, at least about 4500 ng·hr/mL, at least about 4600 ng·hr/mL, at least about 4700 ng·hr/mL, at least about 4800 ng·hr/mL, at least about 4900 ng·hr/mL, at least about 5000 ng·hr/mL, at least about 5100 ng·hr/mL, at least about 5200 ng·hr/mL, at least about 5300 ng·hr/mL, at least about 5400 ng·hr/mL, at least about 5500 ng·hr/mL, at least about 5600 ng·hr/mL, at least about 5700 ng·hr/mL, at least about 5800 ng·hr/mL, at least about 5900 ng·hr/mL, at least about 6000 ng·hr/mL, at least about 6100 ng·hr/mL, at least about 6200 ng·hr/mL, at least about 6300 ng·hr/mL, at least about 6400 ng·hr/mL, at least about 6500 ng·hr/mL, at least about 6600 ng·hr/mL, at least about 6700 ng·hr/mL, at least about 6800 ng·hr/mL, at least about 6900 ng·hr/mL, at least about 7000 ng·hr/mL, at least about 7100 ng·hr/mL, at least about 7150 ng·hr/mL, at least about 7200 ng·hr/mL, or at least about 7237.3 ng·hr/mL, and, in some embodiments, may be up to about 100,000 ng·hr/mL.

In some embodiments, the dextromethorphan $AUC_{0-12}$ on the tenth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 40 ng·hr/mL, at least about 50 ng·hr/mL, at least about 60 ng·hr/mL, at least about 70 ng·hr/mL, at least about 80 ng·hr/mL, at least about 90 ng·hr/mL, at least about 100 ng·hr/mL, at least about 150 ng·hr/mL, at least about 200 ng·hr/mL, at least about 250 ng·hr/mL, at least about 300 ng·hr/mL, at least about 350 ng·hr/mL, at least about 400 ng·hr/mL, at least about 450 ng·hr/mL, at least about 500 ng·hr/mL, at least about 550 ng·hr/mL, about 500 ng·hr/mL to about 600 ng·hr/mL, about 500 ng·hr/mL to about 550 ng·hr/mL, about 500 ng·hr/mL to about 525 ng·hr/mL, about 525 ng·hr/mL to about 600 ng·hr/mL, at least about 600 ng·hr/mL, at least about 650 ng·hr/mL, at least about 700 ng·hr/mL, at least about 750 ng·hr/mL, at least about 800 ng·hr/mL, about 800 ng·hr/mL to about 900 ng·hr/mL, about 850 ng·hr/mL to about 900 ng·hr/mL, about 850 ng·hr/mL to about 875 ng·hr/mL, about 875 ng·hr/mL to about 900 ng·hr/mL, about 900 ng·hr/mL to about 1,000 ng·hr/mL, about 1,000 ng·hr/mL to about 1,100 ng·hr/mL, about 1,100 ng·hr/mL to about 1,200 ng·hr/mL, about 1,200 ng·hr/mL to about 1,300 ng·hr/mL, about 1,300 ng·hr/mL to about 1,400 ng·hr/mL, about 1,400 ng·hr/mL to about 1,500 ng·hr/mL, about 1,500 ng·hr/mL to about 1,600 ng·hr/mL, about 1,600 ng·hr/mL to about 1,700 ng·hr/mL, about 1,700 ng·hr/mL to about 1,800 ng·hr/mL, about 1,800 ng·hr/mL to about 2,000 ng·hr/mL, at least about 850 ng·hr/mL, at least about 900 ng·hr/mL, at least about 950 ng·hr/mL, at least about 1000 ng·hr/mL, at least about 1050 ng·hr/mL, at least about 1100 ng·hr/mL, at least about 1150 ng·hr/mL, at least about 1200 ng·hr/mL, at least about 1250 ng·hr/mL, at least about 1300 ng·hr/mL, at least about 1350 ng·hr/mL, at least about 1400 ng·hr/mL, at least about 1450 ng·hr/mL, at least about 1500 ng·hr/mL, at least about 1550 ng·hr/mL, at least about 1600 ng·hr/mL, at least about 1625 ng·hr/mL, at least about 1650 ng·hr/mL, at least about 1675 ng·hr/mL, or at least about 1686.3 ng·hr/mL, and, in some embodiments, may be up to about 50,000 ng·hr/mL.

In some embodiments, the dextromethorphan $AUC_{0-24}$ on the tenth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 50 ng·hr/mL, at least about 75 ng·hr/mL, at least about 100 ng·hr/mL, at least about 200 ng·hr/mL, at least about 300 ng·hr/mL, at least about 400 ng·hr/mL, at least about 500 ng·hr/mL, at least about 600 ng·hr/mL, at least about 700 ng·hr/mL, at least about 800 ng·hr/mL, at least about 900 ng·hr/mL, at least about 1000 ng·hr/mL, at least about 1100 ng·hr/mL, at least about 1200 ng·hr/mL, at least about 1300 ng·hr/mL, at least about 1400 ng·hr/mL, at least about 1500 ng·hr/mL, at least about 1600 ng·hr/mL, at least about 1700 ng·hr/mL, at least about 1800 ng·hr/mL, at least about 1900 ng·hr/mL, at least about 2000 ng·hr/mL, at least about 2100 ng·hr/mL, at least about 2200 ng·hr/mL, at least about 2300 ng·hr/mL, at least about 2400 ng·hr/mL, at least about 2500 ng·hr/mL, at least about 2600 ng·hr/mL, at least about 2700 ng·hr/mL, at least about 2800 ng·hr/mL, at least about 1850 ng·hr/mL, at least about 2900 ng·hr/mL, at least about 2950 ng·hr/mL, or at least about 2975.3 ng·hr/mL, and, in some embodiments, may be up to about 100,000 ng·hr/mL.

In some embodiments, the dextromethorphan $AUC_{0-inf}$ on the tenth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 75 ng·hr/mL, at least about 100 ng·hr/mL, at least about 200 ng·hr/mL, at least about 300 ng·hr/mL, at least about 400 ng·hr/mL, at least about 500 ng·hr/mL, at least about 600 ng·hr/mL, at least about 700 ng·hr/mL, at least about 800 ng·hr/mL, at least about 900 ng·hr/mL, at least about 1000 ng·hr/mL, at least about 1100 ng·hr/mL, at least about 1200 ng·hr/mL, at least about 1300 ng·hr/mL, at least about 1400 ng·hr/mL, at least about 1500 ng·hr/mL, at least about 1600 ng·hr/mL, at least about 1700 ng·hr/mL, at least about 1800 ng·hr/mL, at least about 1900 ng·hr/mL, at least about 2000 ng·hr/mL, at least about 2100 ng·hr/mL, at least about 2200 ng·hr/mL, at least about 2300 ng·hr/mL, at least about 2400 ng·hr/mL, at least about 2500 ng·hr/mL, at least about 2600 ng·hr/mL, at least about 2700 ng·hr/mL, at least about 2800 ng·hr/mL, at least about 2900 ng·hr/mL, at least about 3000 ng·hr/mL, at least about 3100 ng·hr/mL, at least about 3200 ng·hr/mL, at least about 3300 ng·hr/mL, at least about 3400 ng·hr/mL, at least about 3500 ng·hr/mL, at least about 3600 ng·hr/mL, at least about 3700 ng·hr/mL, at least about 3800 ng·hr/mL, at least about 3900 ng·hr/mL, at least about 4000 ng·hr/mL, at least about 4100 ng·hr/mL, at least about 4200 ng·hr/mL, at least about 4300 ng·hr/mL, at least about 4400 ng·hr/mL, at least about 4500 ng·hr/mL, at least about 4600 ng·hr/mL, at least about 4700 ng·hr/mL, at least about 4800 ng·hr/mL, at least about 4900 ng·hr/mL, at least about 5000 ng·hr/mL, at least about 5100 ng·hr/mL, at least about 5200 ng·hr/mL, at least about 5300 ng·hr/mL, at least about 5400 ng·hr/mL, at least about 5500 ng·hr/mL, at least about 5600 ng·hr/mL, at least about 5700 ng·hr/mL, at least about 5800 ng·hr/mL, at least about 5900 ng·hr/mL, at least about 6000 ng·hr/mL, at least about 6100 ng·hr/mL, at least about 6200 ng·hr/mL, at least about 6300 ng·hr/mL, at least about 6400 ng·hr/mL, at least about 6500 ng·hr/mL, at least about 6600 ng·hr/mL, at least about 6700 ng·hr/mL, at least about 6800 ng·hr/mL, at least about 6900 ng·hr/mL, at least about 7000 ng·hr/mL, at least about 7100 ng·hr/mL, at least about 7150 ng·hr/mL, at least about 7200 ng·hr/mL, or at least about 7237.3 ng·hr/mL, and, in some embodiments, may be up to about 100,000 ng·hr/mL.

In some embodiments, the dextromethorphan $C_{max}$ on the first day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least twice the $C_{max}$ that would be achieved by administering the same amount of dextromethorphan without bupropion, hydroxybupropion, threohydroxybupropion, erythrohydroxybupropion, or a metabolite or prodrug of any of these compounds.

In some embodiments, the dextromethorphan $C_{max}$ on the first day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 1.0 ng/mL, at least about 1.5 ng/mL, at least about 2.0 ng/mL, at least about 2.5 ng/mL, at least about 3.0 ng/mL, at least about 3.1 ng/mL, at least about 3.2 ng/mL, at least about 3.3 ng/mL, at least about 3.4 ng/mL, at least about 3.5 ng/mL, at least about 3.6 ng/mL, at least about 3.7 ng/mL, at least about 3.8 ng/mL, at least about 3.9 ng/mL, at least about 4.0 ng/mL, at least about 4.1 ng/mL, at least about 4.2 ng/mL, at least about 4.3 ng/mL, at least about 4.4 ng/mL, at least about 4.5 ng/mL, at least about 4.6 ng/mL, at least about 4.7 ng/mL, at least about 4.8 ng/mL, at least about 4.9 ng/mL, at least about 5.0 ng/mL, at least about 5.1 ng/mL, at least about 5.2 ng/mL, at least about 5.3 ng/mL, at least about 5.4 ng/mL, at least about 5.5 ng/mL, at least about 5.6 ng/mL, at least about 5.7 ng/mL, at least about 5.8 ng/mL, at least about 5.9 ng/mL, at least about 6.0 ng/mL, at least about 6.1 ng/mL, at least about 6.2 ng/mL, at least about 6.3 ng/mL, at least about 6.4 ng/mL, at least about 6.5 ng/mL, at least about 6.6 ng/mL, at least about 6.7 ng/mL, at least about 6.8 ng/mL, at least about 6.9 ng/mL, at least about 7.0 ng/mL, at least about 7.1 ng/mL, at least about 7.2 ng/mL, at least about 7.3 ng/mL, at least about 7.4 ng/mL, at least about 7.5 ng/mL, at least about 7.6 ng/mL, at least about 7.7 ng/mL, at least about 7.8 ng/mL, at least about 7.9 ng/mL, at least about 8.0 ng/mL, at least about 8.1 ng/mL, at least about 8.2 ng/mL, at least about 8.3 ng/mL, at least about 8.4 ng/mL, at least about 8.5 ng/mL, at least about 8.6 ng/mL, or at least about 8.7 ng/mL, and, in some embodiments, may be up to about 1000 ng·hr/mL.

In some embodiments, the dextromethorphan $C_{max}$ on the eighth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be about 50 ng/mL to about 60 ng/mL, about 50 ng/mL to about 55 ng/mL, about 55 ng/mL to about 60 ng/mL, about 80 ng/mL to about 90 ng/mL, about 80 ng/mL to about 85 ng/mL, about 85 ng/mL to about 90 ng/mL, about 90 ng/mL to about 95 ng/mL, about 95 ng/mL to about 100 ng/mL, about 100 ng/mL to about 105 ng/mL, about 105 ng/mL to about 110 ng/mL, about 110 ng/mL to about 115 ng/mL, about 115 ng/mL to about 120 ng/mL, about 120 ng/mL to about 130 ng/mL, about 130 ng/mL to about 135 ng/mL, about 135 ng/mL to about 140 ng/mL, about 140 ng/mL to about 145 ng/mL, about 145 ng/mL to about 150 ng/mL, about 150 ng/mL to about 155 ng/mL, about 155 ng/mL to about 160 ng/mL, about 160 ng/mL to about 170 ng/mL, about 170 ng/mL to about 200 ng/mL, at least about 6.0 ng/mL, at least about 7.0 ng/mL, at least about 8.0 ng/mL, at least about 9.0 ng/mL, at least about 10 ng/mL, at least about 15 ng/mL, at least about 20 ng/mL, at least about 25 ng/mL, at least about 30 ng/mL, at least about 35 ng/mL, at least about 40 ng/mL, at least about 45 ng/mL, at least about 50 ng/mL, at least about 55 ng/mL, at least about 60 ng/mL, at least about 65 ng/mL, at least about 70 ng/mL, at least about 75 ng/mL, at least about 80 ng/mL, at least about 85 ng/mL, at least about 90 ng/mL, at least about 95 ng/mL, at least about 100 ng/mL, at least about 105 ng/mL, at least about 110 ng/mL, at least about 115 ng/mL, at least about 120 ng/mL, at least about 125 ng/mL, at least about 130 ng/mL, at least about 135 ng/mL, at least about 140 ng/mL, at least about 145 ng/mL, at least about 150 ng/mL, at least about 155 ng/mL, or at least about 158.1 ng/mL, and, in some embodiments, may be up to about 10,000 ng/mL.

In some embodiments, the dextromethorphan $C_{max}$ on the ninth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be about 50 ng/mL to about 60 ng/mL, about 50 ng/mL to about 55 ng/mL, about 55 ng/mL to about 60 ng/mL, about 80 ng/mL to about 90 ng/mL, about 80 ng/mL to about 85 ng/mL, about 85 ng/mL to about 90 ng/mL, about 90 ng/mL to about 95 ng/mL, about 95 ng/mL to about 100 ng/mL, about 100 ng/mL to about 105 ng/mL, about 105 ng/mL to about 110 ng/mL, about 110 ng/mL to about 115 ng/mL, about 115 ng/mL to about 120 ng/mL, about 120 ng/mL to about 130 ng/mL, about 130 ng/mL to about 135 ng/mL, about 135 ng/mL to about 140 ng/mL, about 140 ng/mL to about 145 ng/mL, about 145 ng/mL to about 150 ng/mL, about 150 ng/mL to about 155 ng/mL, about 155 ng/mL to about 160 ng/mL, about 160 ng/mL to about 170 ng/mL, about 170 ng/mL to about 200 ng/mL, at least about 6.0 ng/mL, at least about 7.0 ng/mL, at least about 8.0 ng/mL, at least about 9.0 ng/mL, at least about 10 ng/mL, at least about 15 ng/mL, at least about 20 ng/mL, at least about 25 ng/mL, at least about 30 ng/mL, at least about 35 ng/mL, at least about 40 ng/mL, at least about 45 ng/mL, at least about 50 ng/mL, at least about 55 ng/mL, at least about 60 ng/mL, at least about 65 ng/mL, at least about 70 ng/mL, at least about 75 ng/mL, at least about 80 ng/mL, at least about 85 ng/mL, at least about 90 ng/mL, at least about 95 ng/mL, at least about 100 ng/mL, at least about 105 ng/mL, at least about 110 ng/mL, at least about 115 ng/mL, at least about 120 ng/mL, at least about 125 ng/mL, at least about 130 ng/mL, at least about 135 ng/mL, at least about 140 ng/mL, at least about 145 ng/mL, at least about 150 ng/mL, at least about 155 ng/mL, or at least about 158.1 ng/mL, and, in some embodiments, may be up to about 10,000 ng/mL.

In some embodiments, the dextromethorphan $C_{max}$ on the tenth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be about 50 ng/mL to about 60 ng/mL, about 50 ng/mL to about 55 ng/mL, about 55 ng/mL to about 60 ng/mL, about 80 ng/mL to about 90 ng/mL, about 80 ng/mL to about 85 ng/mL, about 85 ng/mL to about 90 ng/mL, about 90 ng/mL to about 95 ng/mL, about 95 ng/mL to about 100 ng/mL, about 100 ng/mL to about 105 ng/mL, about 105 ng/mL to about 110 ng/mL, about 110 ng/mL to about 115 ng/mL, about 115 ng/mL to about 120 ng/mL, about 120 ng/mL to about 130 ng/mL, about 130 ng/mL to about 135 ng/mL, about 135 ng/mL to about 140 ng/mL, about 140 ng/mL to about 145 ng/mL, about 145 ng/mL to about 150 ng/mL, about 150 ng/mL to about 155 ng/mL, about 155 ng/mL to about 160 ng/mL, about 160 ng/mL to about 170 ng/mL, about 170 ng/mL to about 200 ng/mL, at least about 6.0 ng/mL, at least about 7.0 ng/mL, at least about 8.0 ng/mL, at least about 9.0 ng/mL, at least about 10 ng/mL, at least about 15 ng/mL, at least about 20 ng/mL, at least about 25 ng/mL, at least about 30 ng/mL, at least about 35 ng/mL, at least about 40 ng/mL, at least about 45 ng/mL, at least about 50 ng/mL, at least about 55 ng/mL, at least about 60 ng/mL, at least about 65 ng/mL, at least about 70 ng/mL, at least about 75 ng/mL, at least about 80 ng/mL, at least about 85 ng/mL, at least about 90 ng/mL, at least about 95 ng/mL, at least about 100 ng/mL, at least about 105 ng/mL, at least about 110 ng/mL, at least about 115 ng/mL, at least about 120 ng/mL, at least about 125 ng/mL, at least about 130 ng/mL, at least about 135 ng/mL, at least about 140 ng/mL, at least about 145 ng/mL, at least about 150 ng/mL, at least about 155 ng/mL, or at least about 158.1 ng/mL, and, in some embodiments, may be up to about 10,000 ng/mL.

In some embodiments, bupropion, hydroxybupropion, threohydroxybupropion, erythrohydroxybupropion, or a metabolite or prodrug of any of these compounds, is administered in an amount that results in a $C_{avg}$ of dextromethorphan, over the period between two separate and consecutive administrations of dextromethorphan, that is at least about 4.0 ng/mL, at least about 5.0 ng/mL, at least about 6.0 ng/mL, at least about 7.0 ng/mL, at least about 8.0 ng/mL, at least about 9.0 ng/mL, at least about 10 ng/mL, at least about 15 ng/mL, at least about 20 ng/mL, at least about 25 ng/mL, at least about 30 ng/mL, at least about 35 ng/mL, at least about 40 ng/mL, at least about 45 ng/mL, at least about 50 ng/mL, at least about 55 ng/mL, at least about 60 ng/mL, at least about 65 ng/mL, at least about 70 ng/mL, at least about 75 ng/mL, at least about 80 ng/mL, at least about 85 ng/mL, at least about 90 ng/mL, at least about 95 ng/mL, at least about 100 ng/mL, at least about 105 ng/mL, at least about 110 ng/mL, at least about 115 ng/mL, at least about 120 ng/mL, at least about 125 ng/mL, at least about 130 ng/mL, at least about 135 ng/mL, at least about 140 ng/mL, or at least about 140.5 ng/mL, about 20 ng/mL to about 30 ng/mL, about 30 ng/mL to about 40 ng/mL, about 40 ng/mL to about 50 ng/mL, about 50 ng/mL to about 55 ng/mL, about 55 ng/mL to about 60 ng/mL, about 80 ng/mL to about 90 ng/mL, about 80 ng/mL to about 85 ng/mL, about 85 ng/mL to about 90 ng/mL, about 90 ng/mL to about 95 ng/mL, about 95 ng/mL to about 100 ng/mL, about 100 ng/mL to about 105 ng/mL, about 105 ng/mL to about 110 ng/mL, about 110 ng/mL to about 115 ng/mL, about 115 ng/mL to about 120 ng/mL, about 120 ng/mL to about 130 ng/mL, about 130 ng/mL to about 135 ng/mL, about 135 ng/mL to about 140 ng/mL, about 140 ng/mL to about 145 ng/mL, about 145 ng/mL to about 150 ng/mL, about 150 ng/mL to about 155 ng/mL, about 155 ng/mL to about 160 ng/mL, about 160 ng/mL to about 170 ng/mL, about 170 ng/mL to about 200 ng/mL, and, in some embodiments, may be up to about 10,000 ng/mL. For example, if dextromethorphan is administered at 8 am and at 8 pm on day 1, and no dextromethorphan is administered after 8 am and before 8 pm on day 1, the period between two separate and consecutive administrations of dextromethorphan is from immediately after 8 am to immediately before 8 pm on day 1.

In some embodiments, the dextromethorphan $C_{avg}$ on the eighth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 4.0 ng/mL, at least about 5.0 ng/mL, at least about 6.0 ng/mL, at least about 7.0 ng/mL, at least about 8.0 ng/mL, at least about 9.0 ng/mL, at least about 10 ng/mL, at least about 15 ng/mL, at least about 20 ng/mL, at least about 25 ng/mL, at least about 30 ng/mL, at least about 35 ng/mL, at least about 40 ng/mL, at least about 45 ng/mL, at least about 50 ng/mL, at least about 55 ng/mL, at least about 60 ng/mL, at least about 65 ng/mL, at least about 70 ng/mL, at least about 75 ng/mL, at least about 80 ng/mL, at least about 85 ng/mL, at least about 90 ng/mL, at least about 95 ng/mL, at least about 100 ng/mL, at least about 105 ng/mL, at least about 110 ng/mL, at least about 115 ng/mL, at least about 120 ng/mL, at least about 125 ng/mL, at least about 130 ng/mL, at least about 135 ng/mL, at least about 140 ng/mL, or at least about 140.5 ng/mL, about 20 ng/mL to about 30 ng/mL, about 30 ng/mL to about 40 ng/mL, about 40 ng/mL to about 50 ng/mL, about 50 ng/mL to about 55 ng/mL, about 55 ng/mL to about 60 ng/mL, about 80 ng/mL to about 90 ng/mL, about 80 ng/mL to about 85 ng/mL, about 85 ng/mL to about 90 ng/mL, about 90 ng/mL to about 95 ng/mL, about 95 ng/mL to about 100 ng/mL, about 100 ng/mL to about 105 ng/mL, about 105 ng/mL to about 110 ng/mL, about 110 ng/mL to about 115 ng/mL, about 115 ng/mL to about 120 ng/mL, about 120 ng/mL to about 130 ng/mL, about 130 ng/mL to about 135 ng/mL, about 135 ng/mL to about 140 ng/mL, about 140 ng/mL to about 145 ng/mL, about 145 ng/mL to about 150 ng/mL, about 150 ng/mL to about 155 ng/mL, about 155 ng/mL to about 160 ng/mL, about 160 ng/mL to about 170 ng/mL, about 170 ng/mL to about 200 ng/mL, and, in some embodiments, may be up to about 10,000 ng/mL. The $C_{avg}$ values given above can be for the period between two separate and consecutive administrations of dextromethorphan, or if dextromethorphan is administered only once on Day 8, the $C_{avg}$ can be for 12 hours after the first dose of dextromethorphan.

In some embodiments, the dextromethorphan $C_{avg}$ on the ninth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 4.0 ng/mL, at least about 5.0 ng/mL, at least about 6.0 ng/mL, at least about 7.0 ng/mL, at least about 8.0 ng/mL, at least about 9.0 ng/mL, at least about 10 ng/mL, at least about 15 ng/mL, at least about 20 ng/mL, at least about 25 ng/mL, at least about 30 ng/mL, at least about 35 ng/mL, at least about 40 ng/mL, at least about 45 ng/mL, at least about 50 ng/mL, at least about 55 ng/mL, at least about 60 ng/mL, at least about 65 ng/mL, at least about 70 ng/mL, at least about 75 ng/mL, at least about 80 ng/mL, at least about 85 ng/mL, at least about 90 ng/mL, at least about 95 ng/mL, at least about 100 ng/mL, at least about 105 ng/mL, at least about 110 ng/mL, at least about 115 ng/mL, at least about 120 ng/mL, at least about 125 ng/mL, at least about 130 ng/mL, at least about 135 ng/mL, at least about 140 ng/mL, or at least about 140.5 ng/mL, about 20 ng/mL to about 30 ng/mL, about 30 ng/mL to about 40 ng/mL, about 40 ng/mL to about 50 ng/mL, about 50 ng/mL to about 55 ng/mL, about 55 ng/mL to about 60 ng/mL, about 80 ng/mL to about 90 ng/mL, about 80 ng/mL to about 85 ng/mL, about 85 ng/mL to about 90 ng/mL, about 90 ng/mL to about 95 ng/mL, about 95 ng/mL to about 100 ng/mL, about 100 ng/mL to about 105 ng/mL, about 105 ng/mL to about 110 ng/mL, about 110 ng/mL to about 115 ng/mL, about 115 ng/mL to about 120 ng/mL, about 120 ng/mL to about 130 ng/mL, about 130 ng/mL to about 135 ng/mL, about 135 ng/mL to about 140 ng/mL, about 140 ng/mL to about 145 ng/mL, about 145 ng/mL to about 150 ng/mL, about 150 ng/mL to about 155 ng/mL, about 155 ng/mL to about 160 ng/mL, about 160 ng/mL to about 170 ng/mL, about 170 ng/mL to about 200 ng/mL, and, in some embodiments, may be up to about 10,000 ng/mL. The $C_{avg}$ values given above can be for the period between two separate and consecutive administrations of dextromethorphan, or if dextromethorphan is administered only once on Day 9, the $C_{avg}$ can be for 12 hours after the first dose of dextromethorphan.

In some embodiments, the dextromethorphan $C_{avg}$ on the tenth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 4.0 ng/mL, at least about 5.0 ng/mL, at least about 6.0 ng/mL, at least about 7.0 ng/mL, at least about 8.0 ng/mL, at least about 9.0 ng/mL, at least about 10 ng/mL, at least about 15 ng/mL, at least about 20 ng/mL, at least about 25 ng/mL, at least about 30 ng/mL, at least about 35 ng/mL, at least about 40 ng/mL, at least about 45 ng/mL, at least about 50 ng/mL, at least about 55 ng/mL, at least about 60 ng/mL, at least about 65 ng/mL, at least about 70 ng/mL, at least about 75 ng/mL, at least about 80 ng/mL, at least about 85 ng/mL, at least about 90 ng/mL, at least about 95 ng/mL, at least about 100 ng/mL, at least about 105 ng/mL, at least about 110 ng/mL, at least about 115 ng/mL, at least about 120 ng/mL, at least about 125 ng/mL, at least about 130 ng/mL, at least about 135 ng/mL, at least about 140 ng/mL, or at least about 140.5 ng/mL, about 20 ng/mL to about 30 ng/mL, about 30 ng/mL to about 40 ng/mL, about 40 ng/mL to about 50 ng/mL, about 50 ng/mL to about 55 ng/mL, about 55 ng/mL to about 60 ng/mL, about 80 ng/mL to about 90 ng/mL, about 80 ng/mL to about 85 ng/mL, about 85 ng/mL to about 90 ng/mL, about 90 ng/mL to about 95 ng/mL, about 95 ng/mL to about 100 ng/mL, about 100 ng/mL to about 105 ng/mL, about 105 ng/mL to about 110 ng/mL, about 110 ng/mL to about 115 ng/mL, about 115 ng/mL to about 120 ng/mL, about 120 ng/mL to about 130 ng/mL, about 130 ng/mL to about 135 ng/mL, about 135 ng/mL to about 140 ng/mL, about 140 ng/mL to about 145 ng/mL, about 145 ng/mL to about 150 ng/mL, about 150 ng/mL to about 155 ng/mL, about 155 ng/mL to about 160 ng/mL, about 160 ng/mL to about 170 ng/mL, about 170 ng/mL to about 200 ng/mL, and, in some embodiments, may be up to about 10,000 ng/mL. The $C_{avg}$ values given above can be for the period between two separate and consecutive administrations of dextromethorphan, or if dextromethorphan is administered only once on Day 10, the $C_{avg}$ can be for 12 hours after the first dose of dextromethorphan.

The dextromethorphan fluctuation index values FI (%) can be determined by equation:

$$FI(\%) = \frac{(C_{max} - C_{min})}{C_{avg}} \times 100.$$

In some embodiments, the dextromethorphan FI (%) on the eighth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is reduced by at least 1.5-fold or at least 2-fold as compared to dextromethorphan that is administered for eight days without plasma level enhancement, such as by co-administration of dextromethorphan with of bupropion, hydroxybupropion, threohydroxybupropion, erythrohydroxybupropion, or a metabolite or prodrug of any of these compounds.

In some embodiments, the dextromethorphan FI (%) on the ninth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is reduced by at least 1.5-fold or at least 2-fold as compared to dextromethorphan that is administered for nine days without plasma level enhancement, such as by co-administration of dextromethorphan with of bupropion, hydroxybupropion, threohydroxybupropion, erythrohydroxybupropion, or a metabolite or prodrug of any of these compounds.

In some embodiments, the dextromethorphan FI (%) on the tenth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is reduced by at least 1.5-fold or at least 2-fold as compared to dextromethorphan that is administered for ten days without plasma level enhancement, such as by co-administration of dextromethorphan with of bupropion, hydroxybupropion, threohydroxybupropion, erythrohydroxybupropion, or a metabolite or prodrug of any of these compounds.

In some embodiments, the dextromethorphan FI (%) on the eighth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is less than 100%, less than 50%, less than 40%, less than 30%, about 20-50%, about 20-40%, about 20-30%, or any FI (%) value in a range bounded by any of these values.

In some embodiments, the dextromethorphan FI (%) on the ninth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is less than 100%, less than 50%, less than 40%, less than 30%, about 20-50%, about 20-40%, about 20-30%, or any FI (%) value in a range bounded by any of these values.

In some embodiments, the dextromethorphan FI (%) on the ninth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is less than 100%, less than 50%, less than 40%, less than 30%, about 20-50%, about 20-40%, about 20-30%, or any FI (%) value in a range bounded by any of these values.

In some embodiments, the dextrorphan FI (%) on the eighth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is reduced by at least 1.5-fold, at least 2-fold, at least 3-fold, at least 4-fold, at least 5-fold, or at least 6-fold as compared to dextromethorphan that is administered for eight days without plasma level enhancement, such as by co-administration of dextromethorphan with of bupropion, hydroxybupropion, threohydroxybupropion, erythrohydroxybupropion, or a metabolite or prodrug of any of these compounds.

In some embodiments, the dextrorphan FI (%) on the ninth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is reduced by at least 1.5-fold, at least 2-fold, at least 3-fold, at least 4-fold, at least 5-fold, or at least 6-fold as compared to dextromethorphan that is administered for nine days without plasma level enhancement, such as by co-administration of dextromethorphan with of bupropion, hydroxybupropion, threohydroxybupropion, erythrohydroxybupropion, or a metabolite or prodrug of any of these compounds.

In some embodiments, the dextrorphan FI (%) on the tenth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is reduced by at least 1.5-fold, at least 2-fold, at least 3-fold, at least 4-fold, at least 5-fold, or at least 6-fold as compared to dextromethorphan that is administered for ten days without plasma level enhancement, such as by co-administration of dextromethorphan with of bupropion, hydroxybupropion, threohydroxybupropion, erythrohydroxybupropion, or a metabolite or prodrug of any of these compounds.

In some embodiments, the dextrorphan FI (%) on the eighth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is less than 100%, less than 70%, less than 60%, less than 50%, about 30-70%, about 30-60%, about 30-50%, or any FI (%) value in a range bounded by any of these values.

In some embodiments, the dextrorphan FI (%) on the ninth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is less than 100%, less than 70%, less than 60%, less than 50%, about 30-70%, about 30-60%, about 30-50%, or any FI (%) value in a range bounded by any of these values.

In some embodiments, the dextrorphan FI (%) on the ninth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is less than 100%, less than 70%, less than 60%, less than 50%, about 30-70%, about 30-60%, about 30-50%, or any FI (%) value in a range bounded by any of these values.

In some embodiments, the dextromethorphan trough level (e.g. plasma level 12 hours after administration; also referred herein as "$C_{min}$") on the first day that bupropion, hydroxybupropion, threohydroxybupropion, erythrohydroxybupropion, or a metabolite or prodrug of any of these compounds, is administered may be at least twice the trough level that would be achieved by administering the same amount of dextromethorphan without bupropion, hydroxybupropion, threohydroxybupropion, erythrohydroxybupropion, or a metabolite or prodrug of any of these compounds.

In some embodiments, the dextromethorphan $C_{min}$ on the first day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 0.8 ng/mL, at least about 0.9 ng/mL, at least about 1.0 ng/mL, at least about 1.1 ng/mL, at least about 1.2 ng/mL, at least about 1.3 ng/mL, at least about 1.4 ng/mL, at least about 1.5 ng/mL, at least about 1.6 ng/mL, at least about 1.7 ng/mL, at least about 1.8 ng/mL, at least about 1.9 ng/mL, at least about 2.0 ng/mL, at least about 2.1 ng/mL, at least about 2.2 ng/mL, at least about 2.3 ng/mL, at least about 2.4 ng/mL, at least about 2.5 ng/mL, or at least about 2.5 ng/mL, and may be up to about 100 ng/mL.

In some embodiments, the dextromethorphan $C_{min}$ on the fifth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 1.5 ng/mL, at least about 2.0 ng/mL, at least about 3.0 ng/mL, at least about 4.0 ng/mL, at least about 5.0 ng/mL, at least about 6.0 ng/mL, at least about 7.0 ng/mL, at least about 8.0 ng/mL, at least about 9.0 ng/mL, at least about 10 ng/mL, at least about 15 ng/mL, at least about 20 ng/mL, at least about 25 ng/mL, at least about 30 ng/mL, at least about 35 ng/mL, at least about 40 ng/mL, at least about 45 ng/mL, at least about 50 ng/mL, at least about 55 ng/mL, at least about 60 ng/mL, at least about 65 ng/mL, at least about 70 ng/mL, at least about 75 ng/mL, at least about 80 ng/mL, or at least about 80.9 ng/mL, and may be up to about 10,000 ng/mL.

In some embodiments, the dextromethorphan $C_{min}$ on the sixth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 1.5 ng/mL, at least about 2.0 ng/mL, at least about 3.0 ng/mL, at least about 4.0 ng/mL, at least about 5.0 ng/mL, at least about 6.0 ng/mL, at least about 7.0 ng/mL, at least about 8.0 ng/mL, at least about 9.0 ng/mL, at least about 10 ng/mL, at least about 15 ng/mL, at least about 20 ng/mL, at least about 25 ng/mL, at least about 30 ng/mL, at least about 35 ng/mL, at least about 40 ng/mL, at least about 45 ng/mL, at least about 50 ng/mL, at least about 55 ng/mL, at least about 60 ng/mL, at least about 65 ng/mL, at least about 70 ng/mL, at least about 75 ng/mL, at least about 80 ng/mL, at least about 85 ng/mL, at least about 90 ng/mL, at least about 95 ng/mL, at least about 100 ng/mL, or at least about 102.2 ng/mL, and may be up to about 10,000 ng/mL.

In some embodiments, the dextromethorphan $C_{min}$ on the seventh day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 1.5 ng/mL, at least about 2.0 ng/mL, at least about 3.0 ng/mL, at least about 4.0 ng/mL, at least about 5.0 ng/mL, at least about 6.0 ng/mL, at least about 7.0 ng/mL, at least about 8.0 ng/mL, at least about 9.0 ng/mL, at least about 10 ng/mL, at least about 15 ng/mL, at least about 20 ng/mL, at least about 25 ng/mL, at least about 30 ng/mL, at least about 35 ng/mL, at least about 40 ng/mL, at least about 45 ng/mL, at least about 50 ng/mL, at least about 55 ng/mL, at least about 60 ng/mL, at least about 65 ng/mL, at least about 70 ng/mL, at least about 75 ng/mL, at least about 80 ng/mL, at least about 85 ng/mL, at least about 90 ng/mL, at least about 95 ng/mL, at least about 100 ng/mL, at least about 105 ng/mL, at least about 110 ng/mL, or at least about 110.6 ng/mL, and may be up to about 10,000 ng/mL.

In some embodiments, the dextromethorphan $C_{min}$ on the eighth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 1.5 ng/mL, at least about 2.0 ng/mL, at least about 3.0 ng/mL, at least about 4.0 ng/mL, at least about 5.0 ng/mL, at least about 6.0 ng/mL, at least about 7.0 ng/mL, at least about 8.0 ng/mL, at least about 9.0 ng/mL, at least about 10 ng/mL, at least about 15 ng/mL, at least about 20 ng/mL, at least about 25 ng/mL, at least about 30 ng/mL, at least about 35 ng/mL, at least about 40 ng/mL, at least about 45 ng/mL, at least about 50 ng/mL, at least about 55 ng/mL, at least about 60 ng/mL, at least about 65 ng/mL, at least about 70 ng/mL, at least about 75 ng/mL, at least about 80 ng/mL, at least about 85 ng/mL, at least about 90 ng/mL, at least about 95 ng/mL, at least about 100 ng/mL, at least about 105 ng/mL, at least about 110 ng/mL, at least about 115 ng/mL, at least about 119.3 ng/mL, about 20 ng/mL to about 30 ng/mL, about 30 ng/mL to about 40 ng/mL, about 40 ng/mL to about 50 ng/mL, about 50 ng/mL to about 55 ng/mL, about 55 ng/mL to about 60 ng/mL, about 80 ng/mL to about 90 ng/mL, about 80 ng/mL to about 85 ng/mL, about 85 ng/mL to about 90 ng/mL, about 90 ng/mL to about 95 ng/mL, about 95 ng/mL to about 100 ng/mL, about 100 ng/mL to about 105 ng/mL, about 105 ng/mL to about 110 ng/mL, about 110 ng/mL to about 115 ng/mL, about 115 ng/mL to about 120 ng/mL, about 120 ng/mL to about 130 ng/mL, about 130 ng/mL to about 135 ng/mL, about 135 ng/mL to about 140 ng/mL, about 140 ng/mL to about 145 ng/mL, about 145 ng/mL to about 150 ng/mL, about 150 ng/mL to about 155 ng/mL, about 155 ng/mL to about 160 ng/mL, about 160 ng/mL to about 170 ng/mL, or about 170 ng/mL to about 200 ng/mL, and may be up to about 10,000 ng/mL.

In some embodiments, the dextromethorphan $C_{min}$ on the ninth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 1.5 ng/mL, at least about 2.0 ng/mL, at least about 3.0 ng/mL, at least about 4.0 ng/mL, at least about 5.0 ng/mL, at least about 6.0 ng/mL, at least about 7.0 ng/mL, at least about 8.0 ng/mL, at least about 9.0 ng/mL, at least about 10 ng/mL, at least about 15 ng/mL, at least about 20 ng/mL, at least about 25 ng/mL, at least about 30 ng/mL, at least about 35 ng/mL, at least about 40 ng/mL, at least about 45 ng/mL, at least about 50 ng/mL, at least about 55 ng/mL, at least about 60 ng/mL, at least about 65 ng/mL, at least about 70 ng/mL, at least about 75 ng/mL, at least about 80 ng/mL, at least about 85 ng/mL, at least about 90 ng/mL, at least about 95 ng/mL, at least about 100 ng/mL, at least about 105 ng/mL, at least about 110 ng/mL, at least about 115 ng/mL, at least about 119.3 ng/mL, about 20 ng/mL to about 30 ng/mL, about 30 ng/mL to about 40 ng/mL, about 40 ng/mL to about 50 ng/mL, about 50 ng/mL to about 55 ng/mL, about 55 ng/mL to about 60 ng/mL, about 80 ng/mL to about 90 ng/mL, about 80 ng/mL to about 85 ng/mL, about 85 ng/mL to about 90 ng/mL, about 90 ng/mL to about 95 ng/mL, about 95 ng/mL to about 100 ng/mL, about 100 ng/mL to about 105 ng/mL, about 105 ng/mL to about 110 ng/mL, about 110 ng/mL to about 115 ng/mL, about 115 ng/mL to about 120 ng/mL, about 120 ng/mL to about 130 ng/mL, about 130 ng/mL to about 135 ng/mL, about 135 ng/mL to about 140 ng/mL, about 140 ng/mL to about 145 ng/mL, about 145 ng/mL to about 150 ng/mL, about 150 ng/mL to about 155 ng/mL, about 155 ng/mL to about 160 ng/mL, about 160 ng/mL to about 170 ng/mL, or about 170 ng/mL to about 200 ng/mL, and may be up to about 10,000 ng/mL.

In some embodiments, the dextromethorphan $C_{min}$ on the tenth day that the dextromethorphan plasma level is enhanced, for example by co-administration of dextromethorphan with bupropion, hydroxybupropion, threohydroxybupropion, erythrohydroxybupropion, or a metabolite or prodrug of any of these compounds, is administered may be at least about 1.5 ng/mL, at least about 2.0 ng/mL, at least about 3.0 ng/mL, at least about 4.0 ng/mL, at least about 5.0 ng/mL, at least about 6.0 ng/mL, at least about 7.0 ng/mL, at least about 8.0 ng/mL, at least about 9.0 ng/mL, at least about 10 ng/mL, at least about 15 ng/mL, at least about 20 ng/mL, at least about 25 ng/mL, at least about 30 ng/mL, at least about 35 ng/mL, at least about 40 ng/mL, at least about 45 ng/mL, at least about 50 ng/mL, at least about 55 ng/mL, at least about 60 ng/mL, at least about 65 ng/mL, at least about 70 ng/mL, at least about 75 ng/mL, at least about 80 ng/mL, at least about 85 ng/mL, at least about 90 ng/mL, at least about 95 ng/mL, at least about 100 ng/mL, at least about 105 ng/mL, at least about 110 ng/mL, at least about 115 ng/mL, at least about 119.3 ng/mL, about 20 ng/mL to about 30 ng/mL, about 30 ng/mL to about 40 ng/mL, about 40 ng/mL to about 50 ng/mL, about 50 ng/mL to about 55 ng/mL, about 55 ng/mL to about 60 ng/mL, about 80 ng/mL to about 90 ng/mL, about 80 ng/mL to about 85 ng/mL, about 85 ng/mL to about 90 ng/mL, about 90 ng/mL to about 95 ng/mL, about 95 ng/mL to about 100 ng/mL, about 100 ng/mL to about 105 ng/mL, about 105 ng/mL to about 110 ng/mL, about 110 ng/mL to about 115 ng/mL, about 115 ng/mL to about 120 ng/mL, about 120 ng/mL to about 130 ng/mL, about 130 ng/mL to about 135 ng/mL, about 135 ng/mL to about 140 ng/mL, about 140 ng/mL to about 145 ng/mL, about 145 ng/mL to about 150 ng/mL, about 150 ng/mL to about 155 ng/mL, about 155 ng/mL to about 160 ng/mL, about 160 ng/mL to about 170 ng/mL, or about 170 ng/mL to about 200 ng/mL, and may be up to about 10,000 ng/mL.

In some embodiments, bupropion, hydroxybupropion, threohydroxybupropion, erythrohydroxybupropion, or a metabolite or prodrug of any of these compounds, is administered on the first day of at least two days of treatment with dextromethorphan, wherein a decrease in the dextrorphan plasma level occurs on the first day that bupropion, hydroxybupropion, threohydroxybupropion, erythrohydroxybupropion, or a metabolite or prodrug of any of these compounds, and dextromethorphan are co-administered, as compared to the same amount of dextromethorphan administered without bupropion, hydroxybupropion, threohydroxybupropion, erythrohydroxybupropion, or a metabolite or prodrug of any of these compounds. For example, the dextrorphan plasma level on the first day may be reduced by at least 5% as compared to the dextrorphan plasma level that would be achieved by administering the same amount of dextromethorphan without bupropion.

In some embodiments, bupropion, hydroxybupropion, threohydroxybupropion, erythrohydroxybupropion, or a metabolite or prodrug of any of these compounds, are co-administered for at least five consecutive days, to a human being in need of treatment with dextromethorphan, wherein, on the fifth day, the dextromethorphan plasma level is higher than the dextromethorphan plasma level that would have been achieved by administering the same amount of dextromethorphan administered without bupropion, hydroxybupropion, threohydroxybupropion, erythrohydroxybupropion, or a metabolite or prodrug of any of these compounds, for five consecutive days. For example, the dextromethorphan plasma level on the fifth day (for example at 0 hours, 1 hour, 3 hours, 6 hours, or 12 hours after administration) may be at least 5 times, at least 10 times, at least 20 times, at least 40 times, at least 50 times, at least 60 times, at least 65 times, or up to about 500 times, the level that would be achieved by administering the same amount of dextromethorphan without bupropion, hydroxybupropion, threohydroxybupropion, erythrohydroxybupropion, or a metabolite or prodrug of any of these compounds, for five consecutive days.

In some embodiments, bupropion, hydroxybupropion, threohydroxybupropion, erythrohydroxybupropion, or a metabolite or prodrug of any of these compounds, and dextromethorphan, are co-administered for at least six consecutive days, to a human being in need of treatment with dextromethorphan, wherein, on the sixth day, the dextromethorphan plasma level is higher than the dextromethorphan plasma level that would have been achieved by administering the same amount of dextromethorphan administered without bupropion, hydroxybupropion, threohydroxybupropion, erythrohydroxybupropion, or a metabolite or prodrug of any of these compounds, for six consecutive days. For example, the dextromethorphan plasma level on the sixth day (for example at 0 hours, 1 hour, 3 hours, 6 hours, or 12 hours after administration) may be at least 5 times, at least 10 times, at least 20 times, at least 30 times, at least 50 times, at least 60 times, at least 70 times, at least 75 times, or up to about 500 times, the level that would be achieved by administering the same amount of dextromethorphan without bupropion, hydroxybupropion, threohydroxybupropion, erythrohydroxybupropion, or a metabolite or prodrug of any of these compounds, for six consecutive days.

In some embodiments, bupropion, hydroxybupropion, threohydroxybupropion, erythrohydroxybupropion, or a metabolite or prodrug of any of these compounds, and dextromethorphan, are co-administered for at least seven consecutive days, to a human being in need of treatment with dextromethorphan, wherein, on the seventh day, the dextromethorphan plasma level is higher than the dextromethorphan plasma level that would have been achieved by administering the same amount of dextromethorphan administered without bupropion, hydroxybupropion, threohydroxybupropion, erythrohydroxybupropion, or a metabolite or prodrug of any of these compounds, for seven consecutive days. For example, the dextromethorphan plasma level on the seventh day (for example at 0 hours, 1 hour, 3 hours, 6 hours, or 12 hours after administration) may be at least 5 times, at least 10 times, at least 20 times, at least 30 times, at least 50 times, at least 70 times, at least 80 times, at least 90 times, or up to about 500 times, the level that would be achieved by administering the same amount of dextromethorphan without bupropion, hydroxybupropion, threohydroxybupropion, erythrohydroxybupropion, or a metabolite or prodrug of any of these compounds, for seven consecutive days.

In some embodiments, bupropion, hydroxybupropion, threohydroxybupropion, erythrohydroxybupropion, or a metabolite or prodrug of any of these compounds, and dextromethorphan, are co-administered for at least eight consecutive days, wherein, on the eighth day, dextromethorphan has a plasma level, for example at 0 hours, 1 hour, 3 hours, 6 hours, or 12 hours, after co-administering bupropion with dextromethorphan that is at least 5 times, at least 10 times, at least 20 times, at least 30 times, at least 50 times, at least 60 times, at least 70 times, at least 80 times, at least 90 times, at least 100 times, or up to about 1,000 times, the plasma level that would be achieved by administering the same amount of dextromethorphan without bupropion, hydroxybupropion, threohydroxybupropion, erythrohydroxybupropion, or a metabolite or prodrug of any of these compounds, for eight consecutive days.

In some embodiments, bupropion, hydroxybupropion, threohydroxybupropion, erythrohydroxybupropion, or a metabolite or prodrug of any of these compounds, and dextromethorphan are co-administered for at least eight consecutive days, to a human being in need of treatment with dextromethorphan, wherein, on the eighth day, the dextrorphan plasma level is lower than the dextrorphan plasma level that would have been achieved by administering the same amount of dextromethorphan administered without bupropion, hydroxybupropion, threohydroxybupropion, erythrohydroxybupropion, or a metabolite or prodrug of any of these compounds, for eight consecutive days. For example, the dextrorphan plasma level on the eighth day (for example at 0 hours, 1 hour, 3 hours, 6 hours, or 12 hours after administration) may be reduced by at least 10%, at least 20%, at least 30%, at least 40%, or at least 50%, as compared to the dextrorphan plasma level that would be achieved by administering the same amount of dextromethorphan without bupropion, hydroxybupropion, threohydroxybupropion, erythrohydroxybupropion, or a metabolite or prodrug of any of these compounds, for eight consecutive days.

In some embodiments, bupropion, hydroxybupropion, threohydroxybupropion, erythrohydroxybupropion, or a metabolite or prodrug of any of these compounds, and dextromethorphan, are co-administered for at least nine consecutive days, wherein, on the ninth day, dextromethorphan has a plasma level, for example at 0 hours, 1 hour, 3 hours, 6 hours, or 12 hours, after co-administering bupropion with dextromethorphan that is at least 5 times, at least 10 times, at least 20 times, at least 30 times, at least 50 times, at least 60 times, at least 70 times, at least 80 times, at least 90 times, at least 100 times, or up to about 1,000 times, the plasma level that would be achieved by administering the same amount of dextromethorphan without bupropion, hydroxybupropion, threohydroxybupropion, erythrohydroxybupropion, or a metabolite or prodrug of any of these compounds, for nine consecutive days.

In some embodiments, bupropion, hydroxybupropion, threohydroxybupropion, erythrohydroxybupropion, or a metabolite or prodrug of any of these compounds, and dextromethorphan are co-administered for at least nine consecutive days, to a human being in need of treatment with dextromethorphan, wherein, on the ninth day, the dextrorphan plasma level is lower than the dextrorphan plasma level that would have been achieved by administering the same amount of dextromethorphan administered without bupropion, hydroxybupropion, threohydroxybupropion, erythrohydroxybupropion, or a metabolite or prodrug of any of these compounds, for nine consecutive days. For example, the dextrorphan plasma level on the ninth day (for example at 0 hours, 1 hour, 3 hours, 6 hours, or 12 hours after administration) may be reduced by at least 10%, at least 20%, at least 30%, at least 40%, or at least 50%, as compared to the dextrorphan plasma level that would be achieved by administering the same amount of dextromethorphan without bupropion, hydroxybupropion, threohydroxybupropion, erythrohydroxybupropion, or a metabolite or prodrug of any of these compounds, for nine consecutive days.

In some embodiments, bupropion, hydroxybupropion, threohydroxybupropion, erythrohydroxybupropion, or a metabolite or prodrug of any of these compounds, and dextromethorphan, are co-administered for at least ten consecutive days, wherein, on the tenth day, dextromethorphan has a plasma level, for example at 0 hours, 1 hour, 3 hours, 6 hours, or 12 hours, after co-administering bupropion with dextromethorphan that is at least 5 times, at least 10 times, at least 20 times, at least 30 times, at least 50 times, at least 60 times, at least 70 times, at least 80 times, at least 90 times, at least 100 times, or up to about 1,000 times, the plasma level that would be achieved by administering the same amount of dextromethorphan without bupropion, hydroxybupropion, threohydroxybupropion, erythrohydroxybupropion, or a metabolite or prodrug of any of these compounds, for ten consecutive days.

In some embodiments, bupropion, hydroxybupropion, threohydroxybupropion, erythrohydroxybupropion, or a metabolite or prodrug of any of these compounds, and dextromethorphan are co-administered for at least ten consecutive days, to a human being in need of treatment with dextromethorphan, wherein, on the tenth day, the dextrorphan plasma level is lower than the dextrorphan plasma level that would have been achieved by administering the same amount of dextromethorphan administered without bupropion, hydroxybupropion, threohydroxybupropion, erythrohydroxybupropion, or a metabolite or prodrug of any of these compounds, for ten consecutive days. For example, the dextrorphan plasma level on the tenth day (for example at 0 hours, 1 hour, 3 hours, 6 hours, or 12 hours after administration) may be reduced by at least 10%, at least 20%, at least 30%, at least 40%, or at least 50%, as compared to the dextrorphan plasma level that would be achieved by administering the same amount of dextromethorphan without bupropion, hydroxybupropion, threohydroxybupropion, erythrohydroxybupropion, or a metabolite or prodrug of any of these compounds, for ten consecutive days.

In some embodiments, bupropion may be administered to a human being in an amount that results in an $AUC_{0-12}$ of bupropion in the human being, on day 8, that is at least about 100 ng·hr/mL, at least about 200 ng·hr/mL, at least about 500 ng·hr/mL, at least about 600 ng·hr/mL, at least about 700 ng·hr/mL, at least about 800 ng·hr/mL, at least about 900 ng·hr/mL, at least about 1,000 ng·hr/mL, at least about 1,200 ng·hr/mL, at least 1,600 ng·hr/mL, or up to about 15,000 ng·hr/mL.

In some embodiments, bupropion may be administered to a human being in an amount that results in a $C_{avg}$ of bupropion in the human being, on day 8, that is at least about 10 ng/mL, at least about 20 ng/mL, at least about 40 ng/mL, at least about 50 ng/mL, at least about 60 ng/mL, at least about 70 ng/mL, at least about 80 ng/mL, at least about 90 ng/mL, at least about 100 ng/mL, at least 120 ng/mL, or up to about 1,500 ng/mL.

In some embodiments, bupropion may be administered to a human being in an amount that results in a $C_{max}$ of bupropion in the human being, on day 8, that is at least about 10 ng/mL, at least about 20 ng/mL, at least about 50 ng/mL, at least about 90 ng/mL, at least about 100 ng/mL, at least about 110 ng/mL, at least about 120 ng/mL, at least about 130 ng/mL, at least about 140 ng/mL, at least 200 ng/mL, or up to about 1,500 ng/mL.

Some liquid compositions may comprise about 0.0001% (w/v) to about 50% (w/v), about 0.01% (w/v) to about 20% (w/v), about 0.01% to about 10% (w/v), about 1% (w/v) to about 3% (w/v), about 3% (w/v) to about 5% (w/v), about 5% (w/v) to about 7% (w/v), about 5% (w/v) to about 15% (w/v), about 7% (w/v) to about 10% (w/v), about 10% (w/v) to about 15% (w/v), about 15% (w/v) to about 20% (w/v), about 20% (w/v) to about 30% (w/v), about 30% (w/v) to about 40% (w/v), or about 40% (w/v) to about 50% (w/v) of bupropion, or any amount of bupropion in a range bounded by, or between, any of these values.

Some liquid dosage forms may contain about 10 mg to about 1000 mg, about 50 mg to about 1000 mg, about 10 mg to about 50 mg, about 50 mg to about 100 mg, about 40 mg to about 90 mg, about 200 mg to about 300 mg, about 70 mg to about 95 mg, about 100 mg to about 200 mg, about 105 mg to about 200 mg, about 110 mg to about 140 mg, about 180 mg to about 220 mg, about 280 mg to about 320 mg, about 200 mg, about 150 mg, or about 300 mg of bupropion, or any amount of bupropion in a range bounded by, or between, any of these values.

Some solid compositions may comprise at least about 5% (w/w), at least about 10% (w/w), at least about 20% (w/w), at least about 50% (w/w), at least about 70% (w/w), at least about 80%, about 10% (w/w) to about 30% (w/w), about 10% (w/w) to about 20% (w/w), about 20% (w/w) to about 30% (w/w), about 30% (w/w) to about 50% (w/w), about 30% (w/w) to about 40% (w/w), about 40% (w/w) to about 50% (w/w), about 50% (w/w) to about 80% (w/w), about 50% (w/w) to about 60% (w/w), about 70% (w/w) to about 80% (w/w), or about 80% (w/w) to about 90% (w/w) of bupropion, or any amount of bupropion in a range bounded by, or between, any of these values.

Some solid dosage forms may contain about 10 mg to about 1000 mg, about 50 mg to about 1000 mg, about 10 mg to about 50 mg, about 50 mg to about 100 mg, about 40 mg to about 90 mg, about 200 mg to about 300 mg, about 70 mg to about 95 mg, about 100 mg to about 200 mg, about 105 mg to about 200 mg, about 110 mg to about 140 mg, about 50 mg to about 150 mg, about 180 mg to about 220 mg, about 280 mg to about 320 mg, about 200 mg, about 150 mg, or about 300 mg of bupropion, or any amount of bupropion in a range bounded by, or between, any of these values.

In some embodiments, bupropion is administered at a dose that results in a bupropion plasma level of about 0.1 μM to about 10 μM, about 0.1 μM to about 5 μM, about 0.2 μM to about 3 μM, 0.1 μM to about 1 μM, about 0.2 μM to about 2 μM, 1 μM to about 10 μM, about 1 μM to about 5 μM, about 2 μM to about 3 μM, or about 2.8 μM to about 3 μM, about 1.5 μM to about 2 μM, about 4.5 μM to about 5 μM, about 2.5 μM to about 3 μM, about 1.8 μM, about 4.8 μM, about 2.9 μM, about 2.8 μM, or any plasma level in a range bounded by, or between, any of these values.

In some embodiments, bupropion, hydroxybupropion, or a prodrug of hydroxybupropion, is administered at a dose that results in a hydroxybupropion plasma level of about 0.1 μM to about 10 μM, about 0.1 μM to about 5 μM, about 0.2 μM to about 3 μM, 0.1 μM to about 1 μM, about 0.2 μM to about 2 μM, 1 μM to about 10 μM, about 1 μM to about 5 μM, about 2 μM to about 3 μM, or about 2.8 μM to about 3 μM, about 1.5 μM to about 2 μM, about 4.5 μM to about 5 μM, about 2.5 μM to about 3 μM, about 1.8 μM, about 4.8 μM, about 2.9 μM, about 2.8 μM, or any plasma level in a range bounded by, or between, any of these values.

In some embodiments, bupropion, hydroxybupropion, or a prodrug of hydroxybupropion, may be administered to a human being in an amount that results in an $AUC_{0-12}$ of hydroxybupropion in the human being, on day 8, that is at least about 3,000 ng·hr/mL, at least about 7,000 ng·hr/mL, at least about 10,000 ng·hr/mL, at least about 15,000 ng·hr/mL, at least about 20,000 ng·hr/mL, at least about 30,000 ng·hr/mL, up to about 50,000 ng·hr/mL, up to about 150,000 ng·hr/mL, or any AUC in a range bounded by, or between, any of these values.

In some embodiments, bupropion, hydroxybupropion, or a prodrug of hydroxybupropion, may be administered to a human being in an amount that results in a $C_{max}$ of hydroxybupropion in the human being, on day 8, that is at least about 300 ng/mL, at least about 700 ng/mL, at least about 1,000 ng/mL, at least about 1,500 ng/mL, at least about 2,000 ng/mL, at least about 4,000 ng/mL, up to about 10,000 ng/mL, up to about 50,000 ng/mL, or any $C_{max}$ in a range bounded by, or between, any of these values.

In some embodiments, bupropion, hydroxybupropion, or a prodrug of hydroxybupropion, may be administered to a human being in an amount that results in a $C_{avg}$ of hydroxybupropion in the human being, on day 8, that is at least about 200 ng/mL, at least about 300 ng/mL, at least about 700 ng/mL, at least about 1,000 ng/mL, at least about 1,500 ng/mL, at least about 2,000 ng/mL, at least about 4,000 ng/mL, up to about 10,000 ng/mL, up to about 50,000 ng/mL, or any $C_{avg}$ in a range bounded by, or between, any of these values.

In some embodiments, bupropion, threohydroxybupropion, or a prodrug of threohydroxybupropion, is administered at a dose that results in a threohydroxybupropion plasma level of about 0.1 μM to about 10 μM, about 0.1 μM to about 5 μM, about 0.2 μM to about 3 μM, 0.1 μM to about 1 μM, about 0.2 μM to about 2 μM, 1 μM to about 10 μM, about 1 μM to about 5 μM, about 2 μM to about 3 μM, or about 2.8 μM to about 3 μM, about 1.5 μM to about 2 μM, about 4.5 μM to about 5 μM, about 2.5 μM to about 3 μM, about 1.8 µM, about 4.8 µM, about 2.9 µM, about 2.8 µM, or any plasma level in a range bounded by, or between, any of these values.

In some embodiments, bupropion, threohydroxybupropion, or a prodrug of threohydroxybupropion, may be administered to a human being in an amount that results in an $AUC_{0-12}$ of threohydroxybupropion in the human being, on day 8, that is at least about 1,000 ng·hr/mL, at least about 2,000 ng·hr/mL, at least about 4,000 ng·hr/mL, at least about 5,000 ng·hr/mL, at least about 8,000 ng·hr/mL, up to about 10,000 ng·hr/mL, up to about 40,000 ng·hr/mL, or any AUC in a range bounded by, or between, any of these values.

In some embodiments, bupropion, threohydroxybupropion, or a prodrug of threohydroxybupropion, may be administered to a human being in an amount that results in a $C_{max}$ of threohydroxybupropion in the human being, on day 8, that is at least about 100 ng/mL, at least about 200 ng/mL, at least about 400 ng/mL, at least about 500 ng/mL, at least about 600 ng/mL, at least about 800 ng/mL, up to about 2,000 ng/mL, up to about 10,000 ng/mL, or any $C_{max}$ in a range bounded by, or between, any of these values.

In some embodiments, bupropion, threohydroxybupropion, or a prodrug of threohydroxybupropion, may be administered to a human being in an amount that results in a $C_{avg}$ of threohydroxybupropion in the human being, on day 8, that is at least about 100 ng/mL, at least about 300 ng/mL, at least about 400 ng/mL, at least about 600 ng/mL, at least about 800 ng/mL, up to about 2,000 ng/mL, up to about 10,000 ng/mL, or any $C_{avg}$ in a range bounded by, or between, any of these values.

In some embodiments, bupropion, erythrohydroxybupropion, or a prodrug of erythrohydroxybupropion, is administered at a dose that results in an erythrohydroxybupropion plasma level of about 0.1 µM to about 10 µM, about 0.1 µM to about 5 µM, about 0.2 µM to about 3 µM, 0.1 µM to about 1 µM, about 0.2 µM to about 2 µM, 1 µM to about 10 µM, about 1 µM to about 5 µM, about 2 µM to about 3 µM, or about 2.8 µM to about 3 µM, about 1.5 µM to about 2 µM, about 4.5 µM to about 5 µM, about 2.5 µM to about 3 µM, about 1.8 µM, about 4.8 µM, about 2.9 µM, about 2.8 µM, or any plasma level in a range bounded by, or between, any of these values.

In some embodiments, bupropion, erythrohydroxybupropion, or a prodrug of erythrohydroxybupropion, may be administered to a human being in an amount that results in an $AUC_{0-12}$ of erythrohydroxybupropion in the human being, on day 8, that is at least about 200 ng·hr/mL, at least about 400 ng·hr/mL, at least about 700 ng·hr/mL, at least about 1,000 ng·hr/mL, at least about 1,500 ng·hr/mL, at least about 3,000 ng·hr/mL, up to about 5,000 ng·hr/mL, up to about 30,000 ng·hr/mL, or any plasma level in a range bounded by, or between, any of these values.

In some embodiments, bupropion, erythrohydroxybupropion, or a prodrug of erythrohydroxybupropion, may be administered to a human being in an amount that results in a $C_{max}$ of erythrohydroxybupropion in the human being, on day 8, that is at least about 30 ng/mL, at least about 60 ng/mL, at least about 90 ng/mL, at least about 100 ng/mL, at least about 150 ng/mL, at least about 200 ng/mL, at least about 300 ng/mL, up to about 1,000 ng/mL, or any $C_{max}$ in a range bounded by, or between, any of these values.

In some embodiments, bupropion, erythrohydroxybupropion, or a prodrug of erythrohydroxybupropion, may be administered to a human being in an amount that results in a $C_{avg}$ of erythrohydroxybupropion in the human being, on day 8, that is at least about 20 ng/mL, at least about 30 ng/mL, at least about 50 ng/mL, at least about 80 ng/mL, at least about 90 ng/mL, at least about 100 ng/mL, at least about 150 ng/mL, at least about 200 ng/mL, at least about 300 ng/mL, up to about 1,000 ng/mL, up to about 5,000 ng/mL, or any $C_{avg}$ in a range bounded by, or between, any of these values.

For compositions comprising both dextromethorphan and bupropion, some liquids may comprise about 0.0001% (w/v) to about 50% (w/v), about 0.01% (w/v) to about 20% (w/v), about 0.01% to about 10% (w/v), about 1% (w/v) to about 3% (w/v), about 3% (w/v) to about 5% (w/v), about 5% (w/v) to about 7% (w/v), about 5% (w/v) to about 15% (w/v), about 7% (w/v) to about 10% (w/v), about 10% (w/v) to about 15% (w/v), about 15% (w/v) to about 20% (w/v), about 20% (w/v) to about 30% (w/v), about 30% (w/v) to about 40% (w/v), about 40% (w/v) to about 50% (w/v) of dextromethorphan and bupropion combined, or any amount in a range bounded by, or between, any of these values.

Some solid compositions may comprise at least about 5% (w/w), at least about 10% (w/w), at least about 20% (w/w), at least about 50% (w/w), at least about 70% (w/w), at least about 80%, about 10% (w/w) to about 30% (w/w), about 10% (w/w) to about 20% (w/w), about 20% (w/w) to about 30% (w/w), about 30% (w/w) to about 50% (w/w), about 30% (w/w) to about 40% (w/w), about 40% (w/w) to about 50% (w/w), about 50% (w/w) to about 80% (w/w), about 50% (w/w) to about 60% (w/w), about 70% (w/w) to about 80% (w/w), about 80% (w/w) to about 90% (w/w) of dextromethorphan and bupropion combined, or any amount in a range bounded by, or between, any of these values.

In some embodiments, the weight ratio of dextromethorphan to bupropion in a single composition or dosage form may be about 0.1 to about 2, about 0.2 to about 1, about 0.1 to about 0.3, about 0.2 to about 0.4, about 0.3 to about 0.5, about 0.5 to about 0.7, about 0.8 to about 1, about 0.2 to about 0.3, about 0.4, about 0.45, about 0.6, about 0.9, or any ratio in a range bounded by, or between, any of these values.

A therapeutically effective amount of a therapeutic compound may vary depending upon the circumstances. For example, a daily dose of dextromethorphan may in some instances range from about 0.1 mg to about 1000 mg, about 40 mg to about 1000 mg, about 20 mg to about 600 mg, about 60 mg to about 700 mg, about 100 mg to about 400 mg, about 15 mg to about 20 mg, about 20 mg to about 25 mg, about 25 mg to about 30 mg, about 30 mg to about 35 mg, about 35 mg to about 40 mg, about 40 mg to about 45 mg, about 45 mg to about 50 mg, about 50 mg to about 55 mg, about 55 mg to about 60 mg, about 20 mg to about 60 mg, about 60 mg to about 100 mg, about 100 mg to about 200 mg, about 100 mg to about 140 mg, about 160 mg to about 200 mg, about 200 mg to about 300 mg, about 220 mg to about 260 mg, about 300 mg to about 400 mg, about 340 mg to about 380 mg, about 400 mg to about 500 mg, about 500 mg to about 600 mg, about 15 mg, about 30 mg, about 60 mg, about 120 mg, about 180 mg, about 240 mg, about 360 mg, or any daily dose in a range bounded by, or between, any of these values. Dextromethorphan may be administered once daily; or twice daily or every 12 hours, three times daily, four times daily, or six times daily in an amount that is about half, one third, one quarter, or one sixth, respectively, of the daily dose.

A daily dose of bupropion, may in some instances range from about 10 mg to about 1000 mg, about 50 mg to about 600 mg, about 100 mg to about 2000 mg, about 50 mg to about 100 mg, about 70 mg to about 95 mg, about 100 mg to about 200 mg, about 105 mg to about 200 mg, about 100 mg to about 150 mg, about 150 mg to about 300 mg, about 150 mg to about 200 mg, about 200 mg to about 250 mg, about 250 mg to about 300 mg, about 200 mg about 300 mg, about 300 mg to about 400 mg, about 400 mg to about 500 mg, about 400 mg to about 600 mg, about 360 mg to about 440 mg, about 560 mg to about 640 mg, or about 500 mg to about 600 mg, about 100 mg, about 150 mg, about 200 mg, about 300 mg, about 400 mg, about 600 mg, or any daily dose in a range bounded by, or between, any of these values. Bupropion may be administered once daily; or twice daily or every 12 hours, or three times daily in an amount that is about half or one third, respectively, of the daily dose.

In some embodiments: 1) about 50 mg/day to about 100 mg/day, about 100 mg/day to about 150 mg/day, about 150 mg/day to about 300 mg/day, about 150 mg/day to about 200 mg/day, about 200 mg/day to about 250 mg/day, about 250 mg/day to about 300 mg/day of bupropion, or about 300 mg/day to about 500 mg/day of bupropion; and/or 2) about 15 mg/day to about 60 mg/day, about 15 mg/day to about 30 mg/day, about 30 mg/day to about 45 mg/day, about 45 mg/day to about 60 mg/day, about 60 mg/day to about 100 mg/day, about 80 mg/day to about 110 mg/day, about 100 mg/day to about 150 mg/day, or about 100 mg/day to about 300 mg/day of dextromethorphan, are administered to a human being in need thereof.

In some embodiments, about 150 mg/day of bupropion and about 30 mg/day of dextromethorphan, about 150 mg/day of bupropion and about 60 mg/day of dextromethorphan, about 150 mg/day of bupropion and about 90 mg/day of dextromethorphan, about 150 mg/day of bupropion and about 120 mg/day of dextromethorphan, about 200 mg/day of bupropion and about 30 mg/day of dextromethorphan, about 200 mg/day of bupropion and about 60 mg/day of dextromethorphan, about 200 mg/day of bupropion and about 90 mg/day of dextromethorphan, about 200 mg/day of bupropion and about 120 mg/day of dextromethorphan, about 300 mg/day of bupropion and about 30 mg/day of dextromethorphan, about 300 mg/day of bupropion and about 60 mg/day of dextromethorphan, about 300 mg/day of bupropion and about 90 mg/day of dextromethorphan, or about 300 mg/day of bupropion and about 120 mg/day of dextromethorphan is administered to the human being.

In some embodiments, about 100 mg/day of bupropion and about 15 mg/day of dextromethorphan is administered to the human being for 1, 2, or 3 days, followed by about 200 mg/day of bupropion and about 30 mg/day of dextromethorphan. In some embodiments, about 100 mg/day of bupropion and about 30 mg/day of dextromethorphan is administered to the human being for 1, 2, or 3 days, followed by about 200 mg/day of bupropion and about 60 mg/day of dextromethorphan.

In some embodiments, about 75 mg/day of bupropion and about 15 mg/day of dextromethorphan is administered to the human being for 1, 2, or 3 days, followed by about 150 mg/day of bupropion and about 30 mg/day of dextromethorphan. In some embodiments, about 75 mg/day of bupropion and about 30 mg/day of dextromethorphan is administered to the human being for 1, 2, or 3 days, followed by about 150 mg/day of bupropion and about 60 mg/day of dextromethorphan.

An antidepressant compound, such as bupropion, may be administered for as long as needed to treat a neurological condition, such as pain, depression or cough. In some embodiments, an antidepressant compound, such as bupropion, and dextromethorphan are administered at least once a day, such as once daily or twice daily, for at least 1 day, at least 3 days, at least 5 days, at least 7 days, at least 8 days, at least 9 days, or at least 10 days, at least 14 days, at least 30 days, at least 60 days, at least 90 days, at least 180 days, at least 365 days, or longer.

Therapeutic compounds may be formulated for oral administration, for example, with an inert diluent or with an edible carrier, or it may be enclosed in hard or soft shell gelatin capsules, compressed into tablets, or incorporated directly with the food of the diet. For oral therapeutic administration, the active compound may be incorporated with an excipient and used in the form of ingestible tablets, buccal tablets, troches, capsules, elixirs, suspensions, syrups, wafers, and the like.

Tablets, troches, pills, capsules and the like may also contain one or more of the following: a binder such as gum tragacanth, acacia, corn starch, or gelatin; an excipient, such as dicalcium phosphate; a disintegrating agent such as corn starch, potato starch, alginic acid, and the like; a lubricant such as magnesium stearate; a sweetening agent such as sucrose, lactose, or saccharin; or a flavoring agent such as peppermint, oil of wintergreen, or cherry flavoring. When the dosage unit form is a capsule, it may contain, in addition to materials of the above type, a liquid carrier. Various other materials may be present as coating, for instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. It may be desirable for material in a dosage form or pharmaceutical composition to be pharmaceutically pure and substantially non toxic in the amounts employed.

Some compositions or dosage forms may be a liquid, or may comprise a solid phase dispersed in a liquid.

Therapeutic compounds may be formulated for parental or intraperitoneal administration. Solutions of the active compounds as free bases or pharmacologically acceptable salts can be prepared in water suitably mixed with a surfactant, such as hydroxypropylcellulose. A dispersion can also have an oil dispersed within, or dispersed in, glycerol, liquid polyethylene glycols, and mixtures thereof. Under ordinary conditions of storage and use, these preparations may contain a preservative to prevent the growth of microorganisms.

SPECIFICALLY CONTEMPLATED EMBODIMENTS

The following are examples of embodiments that are specifically contemplated by the inventor:

Embodiment 1

A method of treating pain or a neurological disorder comprising delivering an enhanced plasma level or bioavailability of dextromethorphan, or administering a therapeutically effective amount of a combination of dextromethorphan and an antidepressant compound, to a person in need thereof.

Embodiment 2

A method of treating pain comprising administering a combination of an antidepressant compound and dextromethorphan to a human being in need thereof.

Embodiment 3

A method of enhancing the pain relieving properties of dextromethorphan, comprising co-administering dextromethorphan and an antidepressant compound.

Embodiment 4

A method of increasing dextromethorphan plasma levels in a human being that is an extensive metabolizer of dextromethorphan, comprising co-administering an antidepressant compound to the human being receiving a treatment that includes administration of dextromethorphan.

Embodiment 5

A method of inhibiting the metabolism of dextromethorphan, comprising administering an antidepressant compound to a human being, wherein the human being is an extensive metabolizer of dextromethorphan, and wherein dextromethorphan is present in the body of the human being at the same time as the antidepressant compound.

Embodiment 6

A method of increasing the metabolic lifetime of dextromethorphan, comprising administering an antidepressant compound to a human being, wherein the human being is an extensive metabolizer of dextromethorphan, and wherein dextromethorphan is present in the body of the human being at the same time as the antidepressant compound.

Embodiment 7

A method of correcting extensive metabolism of dextromethorphan, comprising administering an antidepressant compound to a human being in need thereof.

Embodiment 8

A method of improving pain relieving properties of dextromethorphan comprising administering an antidepressant compound in conjunction with administration of dextromethorphan to a human being in need of treatment for pain.

Embodiment 9

A method of improving antitussive properties of dextromethorphan comprising administering an antidepressant compound in conjunction with administration of dextromethorphan to a human being in need of treatment for cough.

Embodiment 10

A method of treating cough comprising administering a combination of an antidepressant compound and dextromethorphan to a human being in need thereof.

Embodiment 11

A method of improving a therapeutic property of dextromethorphan comprising administering an antidepressant compound in conjunction with administration of dextromethorphan to a human being in need of treatment for a neurological disorder.

Embodiment 12

A method of treating a neurological disorder comprising administering a combination of an antidepressant compound and dextromethorphan to a human being in need thereof.

Embodiment 13

A method of treating a neurological disorder comprising administering an antidepressant compound and dextromethorphan to a human being in need thereof, wherein the human being is an extensive metabolizer of dextromethorphan.

Embodiment 14

The method of any preceding embodiment, such as embodiment 1, 2, 3, 4, 5, 6, 7, 8, 9, 10, 11, 12, or 13, wherein the dextromethorphan and the antidepressant compound are administered in separate dosage forms.

Embodiment 15

A pharmaceutical composition comprising a therapeutically effective amount of dextromethorphan, a therapeutically effective amount of an antidepressant compound, and a pharmaceutically acceptable excipient.

Embodiment 16

An oral dosage form comprising at least 20 mg of dextromethorphan and an effective amount of an antidepressant compound to inhibit the metabolism of dextromethorphan in a human being that is an extensive metabolizer of dextromethorphan.

Embodiment 17

The oral dosage form of embodiment 16, wherein about 30 mg to about 350 mg of dextromethorphan is present in the dosage form.

Embodiment 18

The oral dosage form of embodiment 16 or 17, wherein about 100 mg to about 400 mg of bupropion is present in the dosage form.

Embodiment 19

The oral dosage form of any of embodiments 16, 17, or 18, comprising an amount of bupropion that results in a bupropion plasma level of about 0.1 µM to about 10 µM when the oral dosage form is administered to a human being.

Embodiment 20

The oral dosage form of embodiment 19, comprising an amount of bupropion that results in a bupropion plasma level of about 0.1 µM to about 2 µM when the oral dosage form is administered to a human being.

Embodiment 21

The method of any preceding embodiment, such as embodiment 1, 2, 3, 4, 5, 6, 7, 8, 9, 10, 11, 12, or 13, wherein bupropion is administered at a dose that results in a bupropion plasma level of about 0.1 µM to about 10 µM.

Embodiment 22

The method of any preceding embodiment, such as embodiment 21, wherein bupropion is administered at a dose that results in a bupropion plasma level of about 0.3 µM to about 1 µM.

Embodiment 23

The method, composition, or dosage form of any preceding embodiment, such as embodiment 1, 2, 3, 4, 5, 6, 7, 8, 9, 10, 11, 12, 13, 14, 15, 16, or 17, wherein the antidepressant compound is bupropion or a metabolite thereof.

Embodiment 24

The method, composition, or dosage form of any preceding embodiment, such as embodiment 1, 2, 3, 4, 5, 6, 7, 8, 9, 10, 11, 12, 13, 14, 15, 16, or 17, wherein the antidepressant compound is bupropion.

Embodiment 25

The method, composition, or dosage form of any preceding embodiment, such as embodiment 1, 2, 3, 4, 5, 6, 7, 8, 9, 10, 11, 12, 13, 14, 15, 16, or 17, wherein the antidepressant compound is clomipramine, doxepin, fluoxetine, mianserin, imipramine, 2-chloroimipramine, amitriptyline, amoxapine, desipramine, protriptyline, trimipramine, nortriptyline, maprotiline, phenelzine, isocarboxazid, tranylcypromine, paroxetine, trazodone, citalopram, sertraline, aryloxy indanamine, benactyzine, escitalopram, fluvoxamine, venlafaxine, desvenlafaxine, duloxetine, mirtazapine, nefazodone, selegiline, ketamine, or a pharmaceutically acceptable salt thereof

Embodiment 26

The method of any preceding embodiment, such as embodiment 1, 2, 3, 4, 5, 6, 7, 8, 11, 12, 13, 14, 21, 22, 23, 24, or 25, wherein dextromethorphan is administered to the human being for the treatment of cough.

Embodiment 27

A method of treating a neurological disorder comprising administering about 150 mg/day to about 300 mg/day of bupropion and about 30 mg/day to about 120 mg/day of dextromethorphan to a human being in need thereof.

Embodiment 28

A method of treating a neurological disorder comprising administering bupropion and dextromethorphan to a human being in need thereof, wherein the bupropion and dextromethorphan are administered at least once a day for at least 8 days, at least 9 days, or at least 10 days.

Embodiment 29

The method of any preceding embodiment, such as embodiment 1, 2, 3, 4, 5, 6, 7, 8, 9, 10, 11, 12, 13, 14, 21, 22, 23, 24, 25, 26, or 27, wherein bupropion is administered to the human being at least daily for at least 8 days, at least 9 days, or at least 10 days.

Embodiment 30

The method of any preceding embodiment, such as embodiment 1, 2, 3, 4, 5, 6, 7, 8, 9, 10, 11, 12, 13, 14, 21, 22, 23, 24, 25, 26, 27, or 28, wherein dextromethorphan is administered to the human being at least daily for at least 8 days, at least 9 days, or at least 10 days.

Embodiment 31

The method of any preceding embodiment, such as embodiment 28, 29, or 30, wherein bupropion is administered in an amount that results in a plasma concentration of dextromethorphan in the human being, on day 8, that is at least 10 times the plasma concentration of the same amount of dextromethorphan administered without bupropion.

Embodiment 32

The method of any preceding embodiment, such as embodiment 28, 29, 30, or 31, wherein bupropion is administered in an amount that results in an $AUC_{0-12}$ of hydroxybupropion, on day 8, that is at least about 3000 ng·hr/mL.

Embodiment 33

The method of any preceding embodiment, such as embodiment 28, 29, 30, 31, or 32, wherein bupropion is administered in an amount that results in an $AUC_{0-12}$ of erythrohydroxybupropion, on day 8, that is at least about 400 ng·hr/mL.

Embodiment 34

The method of any preceding embodiment, such as embodiment 28, 29, 30, 31, 32, or 33, wherein bupropion is administered in an amount that results in an $AUC_{0-12}$ of threohydroxybupropion, on day 8, that is at least about 2000 ng·hr/mL.

Embodiment 35

The method, composition, or dosage form of any preceding embodiment, such as embodiment 1, 2, 3, 4, 5, 6, 7, 8, 9, 10, 11, 12, 13, 14, 15, 16, 17, 18, 19, 20, 21, 22, 23, 24, 26, 27, 28, 29, 30, 31, 32, 33, or 34, wherein the weight ratio of dextromethorphan to bupropion is about 0.1 to about 0.5.

Embodiment 36

The method of any preceding embodiment, such as embodiment 27, 28, 29, 30, 31, 32, 33, 34, or 35, wherein the human being is an extensive metabolizer of dextromethorphan.

Embodiment 37

The method of any preceding embodiment, such as embodiment 1, 2, 3, 4, 5, 6, 7, 8, 9, 10, 11, 12, 13, 14, 21, 22, 23, 24, 25, 26, 27, 28, 29, 30, 31, 32, 33, 34, 35, or 36, wherein about 150 mg/day of bupropion and about 30 mg/day of dextromethorphan is administered to the human being.

Embodiment 38

The method of any preceding embodiment, such as embodiment 1, 2, 3, 4, 5, 6, 7, 8, 9, 10, 11, 12, 13, 14, 21, 22, 23, 24, 25, 26, 27, 28, 29, 30, 31, 32, 33, 34, 35, or 36, wherein about 150 mg/day of bupropion and about 60 mg/day of dextromethorphan is administered to the human being.

Embodiment 39

The method of any preceding embodiment, such as embodiment 1, 2, 3, 4, 5, 6, 7, 8, 9, 10, 11, 12, 13, 14, 21, 22, 23, 24, 25, 26, 27, 28, 29, 30, 31, 32, 33, 34, 35, or 36, wherein about 200 mg/day of bupropion and about 30 mg/day of dextromethorphan is administered to the human being.

Embodiment 40

The method of any preceding embodiment, such as embodiment 1, 2, 3, 4, 5, 6, 7, 8, 9, 10, 11, 12, 13, 14, 21, 22, 23, 24, 25, 26, 27, 28, 29, 30, 31, 32, 33, 34, 35, or 36, wherein about 100 mg/day of bupropion and about 15 mg/day of dextromethorphan is administered to the human being for about 1 to about 3 days, followed by about 200 mg/day of bupropion and about 30 mg/day of dextromethorphan.

Embodiment 41

The method of any preceding embodiment, such as embodiment 1, 2, 3, 4, 5, 6, 7, 8, 9, 10, 11, 12, 13, 14, 21, 22, 23, 24, 25, 26, 27, 28, 29, 30, 31, 32, 33, 34, 35, or 36, wherein about 200 mg/day of bupropion and about 60 mg/day of dextromethorphan is administered to the human being.

Embodiment 42

The method of any preceding embodiment, such as embodiment 1, 2, 3, 4, 5, 6, 7, 8, 9, 10, 11, 12, 13, 14, 21, 22, 23, 24, 25, 26, 27, 28, 29, 30, 31, 32, 33, 34, 35, or 36, wherein about 100 mg/day of bupropion and about 30 mg/day of dextromethorphan is administered to the human being for about 1 to about 3 days, followed by about 200 mg/day of bupropion and about 60 mg/day of dextromethorphan.

Embodiment 43

The method of any preceding embodiment, such as embodiment 4, 5, 6, 7, 9, 10, 11, 12, 13, 14, 21, 22, 23, 24, 25, 26, 27, 28, 29, 30, 31, 32, 33, 34, 35, 36, 37, 38, 39, 40, 41, or 42, wherein dextromethorphan is administered to the human being for the treatment of pain.

Embodiment 44

The method of any preceding embodiment, such as embodiment 43, wherein the pain comprises postoperative pain, cancer pain, arthritic pain, lumbosacral pain, musculoskeletal pain, central multiple sclerosis pain, nociceptive pain, or neuropathic pain.

Embodiment 45

The method of any preceding embodiment, such as embodiment 43, wherein the pain comprises musculoskeletal pain, neuropathic pain, cancer-related pain, acute pain, or nociceptive pain.

Embodiment 46

The method of any preceding embodiment, such as embodiment 43, wherein the pain comprises postoperative pain.

Embodiment 47

The method of any preceding embodiment, such as embodiment 43, wherein the pain comprises cancer pain.

Embodiment 48

The method of any preceding embodiment, such as embodiment 43, wherein the pain comprises arthritic pain.

Embodiment 49

The method of any preceding embodiment, such as embodiment 43, wherein the pain comprises lumbosacral pain.

Embodiment 50

The method of any preceding embodiment, such as embodiment 43, wherein the pain comprises musculoskeletal pain.

Embodiment 51

The method of any preceding embodiment, such as embodiment 43, wherein the pain comprises neuropathic pain.

Embodiment 52

The method of any preceding embodiment, such as embodiment 43, wherein the pain comprises nociceptive pain.

Embodiment 53

The method of any preceding embodiment, such as embodiment 43, wherein the pain comprises chronic musculoskeletal pain.

Embodiment 54

The method of any preceding embodiment, such as embodiment 43, wherein the pain is associated with rheumatoid arthritis.

Embodiment 55

The method of any preceding embodiment, such as embodiment 43, wherein the pain is associated with juvenile rheumatoid arthritis.

Embodiment 56

The method of any preceding embodiment, such as embodiment 43, wherein the pain is associated with osteoarthritis.

Embodiment 57

The method of any preceding embodiment, such as embodiment 43, wherein the pain is associated with an axial spondyloarthritis.

Embodiment 58

The method of any preceding embodiment, such as embodiment 43, wherein the pain is associated with ankylosing spondylitis.

Embodiment 59

The method of any preceding embodiment, such as embodiment 43, wherein the pain is associated with diabetic peripheral neuropathy.

Embodiment 60

The method of any preceding embodiment, such as embodiment 43, wherein the pain is associated with post-herpetic neuralgia.

Embodiment 61

The method of any preceding embodiment, such as embodiment 43, wherein the pain is associated with trigeminal neuralgia.

Embodiment 62

The method of any preceding embodiment, such as embodiment 43, wherein the pain is associated with mono-radiculopathies.

Embodiment 63

The method of any preceding embodiment, such as embodiment 43, wherein the pain is associated with phantom limb pain.

Embodiment 64

The method of any preceding embodiment, such as embodiment 43, wherein the pain is associated with central pain.

Embodiment 65

The method of any preceding embodiment, such as embodiment 43, wherein the pain comprises cancer-related pain.

Embodiment 66

The method of any preceding embodiment, such as embodiment 43, wherein the pain is associated with lumbar nerve root compression.

Embodiment 67

The method of any preceding embodiment, such as embodiment 43, wherein the pain is associated with spinal cord injury.

Embodiment 68

The method of any preceding embodiment, such as embodiment 43, wherein the pain is associated with post-stroke pain.

Embodiment 69

The method of any preceding embodiment, such as embodiment 43, wherein the pain is associated with central multiple sclerosis pain.

Embodiment 70

The method of any preceding embodiment, such as embodiment 43, wherein the pain is associated with HIV-associated neuropathy.

Embodiment 71

The method of any preceding embodiment, such as embodiment 43, wherein the pain is associated with radiotherapy associated neuropathy.

Embodiment 72

The method of any preceding embodiment, such as embodiment 43, wherein the pain is associated with chemotherapy associated neuropathy.

Embodiment 73

The method of any preceding embodiment, such as embodiment 43, wherein the pain comprises dental pain.

Embodiment 74

The method of any preceding embodiment, such as embodiment 43, wherein the pain is associated with primary dysmenorrhea.

Embodiment 75

The method of any preceding embodiment, such as embodiment 4, 5, 6, 7, 9, 10, 11, 12, 13, 14, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, or 74, wherein 90 mg/day of dextromethorphan is administered to the human being.

Embodiment 76

The method of any preceding embodiment, such as embodiment 75, wherein 45 mg of dextromethorphan is administered twice a day to the human being.

Embodiment 77

The method of any preceding embodiment, such as embodiment 75 or 76, wherein 150 mg/day of bupropion is administered to the human being.

Embodiment 78

The method of any preceding embodiment, such as embodiment 75 or 76, wherein 180 mg/day of bupropion is administered to the human being.

Embodiment 79

The method of any preceding embodiment, such as embodiment 75 or 76, wherein 200 mg/day of bupropion is administered to the human being.

Embodiment 80

The method of any preceding embodiment, such as embodiment 75 or 76, wherein 300 mg/day of bupropion is administered to the human being.

Embodiment 81

A method of increasing dextromethorphan plasma levels in a human being, comprising co-administering threohydroxybupropion, hydroxybupropion, erythrohydroxybupropion, bupropion, or a prodrug thereof, with dextromethorphan to the human being, wherein the threohydroxybupropion, hydroxybupropion, erythrohydroxybupropion, bupropion, or a prodrug thereof, is administered in an amount that results in an $AUC_{0-12}$ of dextromethorphan that is at least about 40 ng·hr/mL.

Embodiment 82

The method of any preceding embodiment, such as embodiment 81, wherein the $AUC_{0-12}$ of dextromethorphan is at least about 50 ng·hr/mL.

Embodiment 83

The method of any preceding embodiment, such as embodiment 81 or 82, wherein the human being is in need of treatment with dextromethorphan.

Embodiment 84

The method of any preceding embodiment, such as embodiment 81, 82, or 83, wherein the human being is an extensive metabolizer of dextromethorphan.

Embodiment 85

The method of any preceding embodiment, such as embodiment 81, 82, 83, or 84, wherein the threohydroxybupropion, hydroxybupropion, erythrohydroxybupropion, bupropion, or a prodrug thereof, and dextromethorphan are administered to the human being at least daily for at least 8 days, at least 9 days, or at least 10 days.

Embodiment 86

The method of any preceding embodiment, such as embodiment 85, wherein the $AUC_{0-12}$ of dextromethorphan on Day 8, Day 9, or Day 10 is at least about 100 ng·hr/mL.

Embodiment 87

The method of any preceding embodiment, such as embodiment 85 or 86, wherein the $AUC_{0-12}$ of dextromethorphan on Day 8, Day 9, or Day 10 is at least about 400 ng·hr/mL.

Embodiment 88

The method of any preceding embodiment, such as embodiment 85, 86, or 87, wherein the $AUC_{0-12}$ of dextromethorphan on Day 8, Day 9, or Day 10 is at least about 800 ng·hr/mL.

Embodiment 89

The method of any preceding embodiment, such as embodiment 85, 86, 87, or 88, wherein the $AUC_{0-12}$ of dextromethorphan on Day 8, Day 9, or Day 10 is at least about 1500 ng·hr/mL.

Embodiment 90

The method of any preceding embodiment, such as embodiment 85, 86, 87, 88, or 89, wherein the $AUC_{0-24}$ of dextromethorphan on Day 8, Day 9, or Day 10 is at least about 100 ng·hr/mL.

Embodiment 91

The method of any preceding embodiment, such as embodiment 85, 86, 87, 88, 89, or 90, wherein the $AUC_{0-24}$ of dextromethorphan on Day 8, Day 9, or Day 10 is at least about 1500 ng·hr/mL.

Embodiment 92

The method of any preceding embodiment, such as embodiment 85, 86, 87, 88, 89, 90, or 91, wherein the $AUC_{0-24}$ of dextromethorphan on Day 8, Day 9, or Day 10 is at least about 2900 ng·hr/mL.

Embodiment 93

The method of any preceding embodiment, such as embodiment 85, 86, 87, 88, 89, 90, 91, or 92, wherein the $AUC_{0-inf}$ of dextromethorphan on Day 8, Day 9, or Day 10 is at least about 100 ng·hr/mL.

Embodiment 94

The method of any preceding embodiment, such as embodiment 85, 86, 87, 88, 89, 90, 91, 92, or 93, wherein the $AUC_{0-inf}$ of dextromethorphan on Day 8, Day 9, or Day 10 is at least about 1500 ng·hr/mL.

Embodiment 95

The method of any preceding embodiment, such as embodiment 85, 86, 87, 88, 89, 90, 91, 92, 93, or 94, wherein the $AUC_{0-inf}$ of dextromethorphan on Day 8, Day 9, or Day 10 is at least about 3500 ng·hr/mL.

Embodiment 96

The method of any preceding embodiment, such as embodiment 85, 86, 87, 88, 89, 90, 91, 92, 93, 94, or 95, wherein the $AUC_{0-inf}$ of dextromethorphan on Day 8, Day 9, or Day 10 is at least about 5000 ng·hr/mL.

Embodiment 97

A method of increasing dextromethorphan plasma levels in a human being, comprising co-administering threohydroxybupropion, hydroxybupropion, erythrohydroxybupropion, bupropion, or a prodrug thereof, with dextromethorphan to the human being, wherein the threohydroxybupropion, hydroxybupropion, erythrohydroxybupropion, bupropion, or a prodrug thereof, is administered in an amount that results in a $C_{max}$ of dextromethorphan that is at least about 6 ng/mL.

Embodiment 98

The method of any preceding embodiment, such as embodiment 97, wherein the human being is in need of treatment with dextromethorphan.

Embodiment 99

The method of any preceding embodiment, such as embodiment 97 or 98, wherein the human being is an extensive metabolizer of dextromethorphan.

Embodiment 100

The method of any preceding embodiment, such as embodiment 97, 98, or 99, wherein the threohydroxybupropion, hydroxybupropion, erythrohydroxybupropion, bupropion, or a prodrug thereof, and dextromethorphan are administered to the human being at least daily for at least 8 days, at least 9 days, or at least 10 days.

Embodiment 101

The method of any preceding embodiment, such as embodiment 100, wherein the $C_{max}$ of dextromethorphan on Day 8, Day 9, or Day 10 is at least about 20 ng/mL.

Embodiment 102

The method of any preceding embodiment, such as embodiment 100 or 101, wherein the $C_{max}$ of dextromethorphan on Day 8, Day 9, or Day 10 is at least about 60 ng/mL.

Embodiment 103

The method of any preceding embodiment, such as embodiment 100, 101, or 102, wherein the $C_{max}$ of dextromethorphan on Day 8, Day 9, or Day 10 is at least about 120 ng/mL.

Embodiment 104

A method of increasing dextromethorphan plasma levels in a human being, comprising co-administering threohydroxybupropion, hydroxybupropion, erythrohydroxybupropion, bupropion, or a prodrug thereof, with dextromethorphan to the human being, wherein the threohydroxybupropion, hydroxybupropion, erythrohydroxybupropion, bupropion, or a prodrug thereof, is administered in an amount that results in a $C_{avg}$ of dextromethorphan over a 12 hour period, after one administration, that is at least about 5 ng/mL.

Embodiment 105

The method of any preceding embodiment, such as embodiment 104, wherein the human being is in need of treatment with dextromethorphan.

Embodiment 106

The method of any preceding embodiment, such as embodiment 104 or 105, wherein the human being is an extensive metabolizer of dextromethorphan.

Embodiment 107

The method of any preceding embodiment, such as embodiment 104, 105, or 106, wherein the threohydroxybupropion, hydroxybupropion, erythrohydroxybupropion, bupropion, or a prodrug thereof, and dextromethorphan are administered to the human being at least daily for at least 8 days, at least 9 days, or at least 10 days.

Embodiment 108

The method of any preceding embodiment, such as embodiment 107, wherein the $C_{avg}$ of dextromethorphan on Day 8, Day 9, or Day 10 is at least about 20 ng/mL.

Embodiment 109

The method of any preceding embodiment, such as embodiment 107 or 108, wherein the $C_{avg}$ of dextromethorphan on Day 8, Day 9, or Day 10 is at least about 70 ng/mL.

Embodiment 110

The method of any preceding embodiment, such as embodiment 107, 108, or 109, wherein the $C_{avg}$ of dextromethorphan on Day 8, Day 9, or Day 10 is at least about 120 ng/mL.

Embodiment 111

A method of increasing dextromethorphan plasma levels in a human being, comprising co-administering bupropion, hydroxybupropion, erythrohydroxybupropion, threohydroxybupropion, or a prodrug of any of these compounds, with dextromethorphan to the human being, wherein the bupropion or a prodrug thereof is administered in an amount that results in an $AUC_{0-12}$ of dextromethorphan that is at least about 40 ng·hr/mL.

Embodiment 112

The method of any preceding embodiment, such as embodiment 111, wherein the $AUC_{0-12}$ of dextromethorphan is at least about 50 ng·hr/mL.

Embodiment 113

The method of any preceding embodiment, such as embodiment 111 or 112, wherein the human being is in need of treatment with dextromethorphan.

Embodiment 114

The method of any preceding embodiment, such as embodiment 111, 112, or 113, wherein the human being is an extensive metabolizer of dextromethorphan.

Embodiment 115

The method of any preceding embodiment, such as embodiment 111, 112, 113, or 114, wherein the bupropion or a prodrug thereof is co-administered with dextromethorphan at least daily for at least two consecutive days.

Embodiment 116

The method of any preceding embodiment, such as embodiment 115, wherein the bupropion or a prodrug thereof and dextromethorphan are administered to the human being at least daily for at least 8 days, at least 9 days, or at least 10 days.

Embodiment 117

The method of any preceding embodiment, such as embodiment 116, wherein the $AUC_{0-12}$ of dextromethorphan on Day 8, Day 9, or Day 10 is at least about 100 ng·hr/mL.

Embodiment 118

The method of any preceding embodiment, such as embodiment 116, wherein the $AUC_{0-12}$ of dextromethorphan on Day 8, Day 9, or Day 10 is at least about 800 ng·hr/mL.

Embodiment 119

The method of any preceding embodiment, such as embodiment 116, wherein the $AUC_{0-12}$ of dextromethorphan on Day 8, Day 9, or Day 10 is at least about 1500 ng·hr/mL.

Embodiment 120

The method of any preceding embodiment, such as embodiment 116, wherein the $AUC_{0-24}$ of dextromethorphan on Day 8, Day 9, or Day 10 is at least about 100 ng·hr/mL.

Embodiment 121

The method of any preceding embodiment, such as embodiment 116, wherein the $AUC_{0-24}$ of dextromethorphan on Day 8, Day 9, or Day 10 is at least about 1500 ng·hr/mL.

Embodiment 122

The method of any preceding embodiment, such as embodiment 116, wherein the $AUC_{0-inf}$ of dextromethorphan on Day 8, Day 9, or Day 10 is at least about 100 ng·hr/mL.

Embodiment 123

The method of any preceding embodiment, such as embodiment 116, wherein the $AUC_{0-inf}$ of dextromethorphan on Day 8, Day 9, or Day 10 is at least about 3500 ng·hr/mL.

Embodiment 124

The method of any preceding embodiment, such as embodiment 116, wherein the $AUC_{0-inf}$ of dextromethorphan on Day 8, Day 9, or Day 10 is at least about 5000 ng·hr/mL.

Embodiment 125

A method of increasing dextromethorphan plasma levels in a human being, comprising co-administering bupropion, hydroxybupropion, erythrohydroxybupropion, threohydroxybupropion, or a prodrug of any of these compounds, with dextromethorphan to the human being, wherein the bupropion or a prodrug thereof is administered in an amount that results in a $C_{max}$ of dextromethorphan that is at least about 6 ng/mL.

Embodiment 126

The method of any preceding embodiment, such as embodiment 125, wherein the human being is in need of treatment with dextromethorphan.

Embodiment 127

The method of any preceding embodiment, such as embodiment 125 or 126, wherein the human being is an extensive metabolizer of dextromethorphan.

Embodiment 128

The method of any preceding embodiment, such as embodiment 126, 127, or 128, wherein the bupropion or a prodrug thereof is co-administered with dextromethorphan at least daily for at least two consecutive days.

Embodiment 129

The method of any preceding embodiment, such as embodiment 128, wherein the bupropion or a prodrug thereof and dextromethorphan are administered to the human being at least daily for at least 8 days, at least 9 days, or at least 10 days.

Embodiment 130

The method of any preceding embodiment, such as embodiment 129, wherein the $C_{max}$ of dextromethorphan on Day 8, Day 9, or Day 10 is at least about 10 ng/mL.

Embodiment 131

The method of any preceding embodiment, such as embodiment 129, wherein the $C_{max}$ of dextromethorphan on Day 8, Day 9, or Day 10 is at least about 60 ng/mL.

Embodiment 132

The method of any preceding embodiment, such as embodiment 129, wherein the $C_{max}$ of dextromethorphan on Day 8, Day 9, or Day 10 is at least about 120 ng/mL.

Embodiment 133

A method of increasing dextromethorphan plasma levels in a human being, comprising co-administering bupropion, hydroxybupropion, erythrohydroxybupropion, threohydroxybupropion, or a prodrug of any of these compounds, with dextromethorphan to the human being, wherein the bupropion or a prodrug thereof is administered in an amount that results in a $C_{avg}$ of dextromethorphan, over the period between two separate and consecutive administrations of dextromethorphan, that is at least about 5 ng/mL.

Embodiment 134

The method of any preceding embodiment, such as embodiment 134, wherein the bupropion or a prodrug thereof is administered in an amount that results in a $C_{avg}$ of dextromethorphan, over the period between two separate and consecutive administrations of dextromethorphan, that is at least about 60 ng/mL.

Embodiment 135

The method of any preceding embodiment, such as embodiment 134, wherein the human being is in need of treatment with dextromethorphan.

Embodiment 136

The method of any preceding embodiment, such as embodiment 134 or 135, wherein the human being is an extensive metabolizer of dextromethorphan.

Embodiment 137

The method of any preceding embodiment, such as embodiment 134, 135, or 136, wherein the bupropion or a prodrug thereof is co-administered with dextromethorphan at least daily for at least two consecutive days.

Embodiment 138

The method of any preceding embodiment, such as embodiment 137, wherein the bupropion or a prodrug thereof and dextromethorphan are administered to the human being at least daily for at least 8 days, at least 9 days, or at least 10 days.

Embodiment 139

The method of any preceding embodiment, such as embodiment 138, wherein the $C_{avg}$ of dextromethorphan on Day 8, Day 9, or Day 10 is at least about 8 ng/mL, wherein the $C_{avg}$ is for the period between two separate and consecutive administrations of dextromethorphan, or if dextromethorphan is administered only once on Day 8, Day 9, or Day 10, the $C_{avg}$ is for 12 hours after the first dose of dextromethorphan on Day 8, Day 9, or Day 10.

Embodiment 140

The method of any preceding embodiment, such as embodiment 138, wherein the Cavg of dextromethorphan on Day 8, Day 9, or Day 10 is at least about 120 ng/mL, wherein the $C_{avg}$ is for the period between two separate and consecutive administrations of dextromethorphan, or if dextromethorphan is administered only once on Day 8, Day 9, or Day 10, the $C_{avg}$ for 12 hours after the first dose of dextromethorphan on Day 8, Day 9, or Day 10.

EXAMPLES

Example 1

Fifteen human subjects were randomized into one of two treatment groups receiving either dextromethorphan (DM) alone, or DM in combination with bupropion, as shown in Table 1 below.

TABLE 1

Study Design

| Group | Dose Levels Bupropion/DM | Dosing Regimen | Duration | Total Subjects |
|---|---|---|---|---|
| A | 0 mg/60 mg | DM: Twice daily, Days 1-8 | Days 1-8 | 8 |
| B | 150 mg/60 mg | Bupropion: Once daily, Days 1-3; Twice daily, Days 4-8 DM: Twice daily, Days 1-8 | Days 1-8 | 7 |

All subjects were extensive, including ultra-rapid, metabolizers of dextromethorphan as determined by CYP2D6 genetic testing. Dextromethorphan was dosed at 12-hour intervals on Days 1-8, with a final morning dose on Day 8. Bupropion was dosed once daily on Days 1-3, and at 12-hour intervals thereafter, with a final morning dose on Day 8.

Plasma samples were collected for concentration analysis of dextromethorphan, total dextrorphan, bupropion, hydroxybupropion, erythrohydroxybupropion, and threohydroxybupropion on days 1 and 8. Plasma samples for determination of trough concentrations of dextromethorphan were obtained approximately 12 hours after dosing on days 1, 5, 6, and 8.

Concentrations of dextromethorphan, total dextrorphan (unconjugated and glucuronide forms), bupropion, hydroxybupropion, erythrohydroxybupropion, and threohydroxybupropion, were determined using LC-MS/MS. Pharmacokinetic parameters were calculated.

Phenotypic determination of dextromethorphan metabolizer status was performed by calculating the dextromethorphan/dextrorphan metabolic ratio as described in Jurica et al. Journal of Clinical Pharmacy and Therapeutics, 2012, 37, 486-490. Plasma concentrations of dextromethorphan and dextrorphan 3 hours after dosing were used, with a dextromethorphan/dextrorphan ratio of 0.3 or greater indicating a poor metabolizer phenotype.

Results

Plasma concentrations of dextromethorphan were significantly increased with bupropion administration, as illustrated in FIG. 1 and Table 2.

TABLE 2

Mean Day 8 Dextromethorphan Plasma Concentrations (ng/mL)

| Time (hours) | Dextromethorphan (Group A) | Dextromethorphan + Bupropion (Group B) |
|---|---|---|
| 0 | 1.2 | 110.6 |
| 1 | 2.4 | 129.3 |
| 2 | 3.6 | 153.9 |
| 3 | 3.6 | 151.6 |
| 4 | 3.3 | 149.1 |
| 6 | 2.5 | 150.0 |
| 8 | 1.9 | 144.4 |
| 12 | 1.1 | 119.3 |
| 24 | 0.4 | 95.3 |
| 36 | 0.1 | 69.0 |

Figure 2:
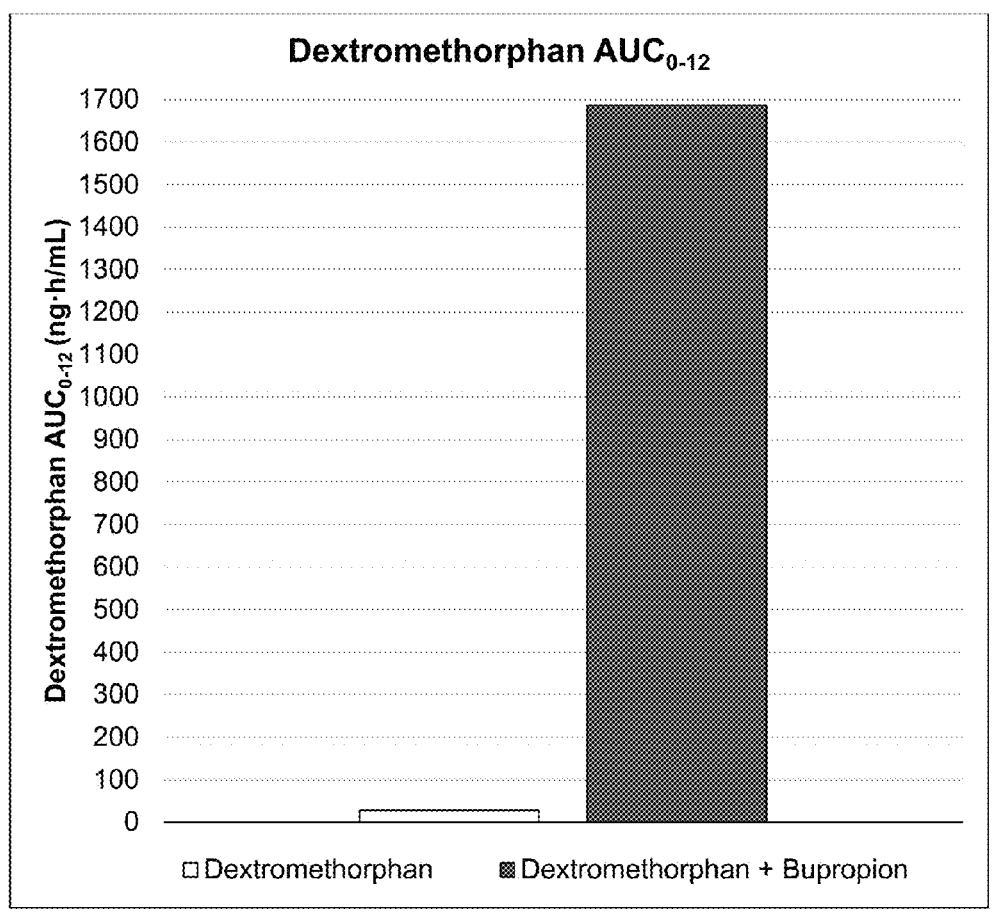
FIG. 2 depicts mean $AUC_{0-12}$ of dextromethorphan on Day 8 for subjects administered dextromethorphan alone or dextromethorphan and bupropion.
Figure 3:
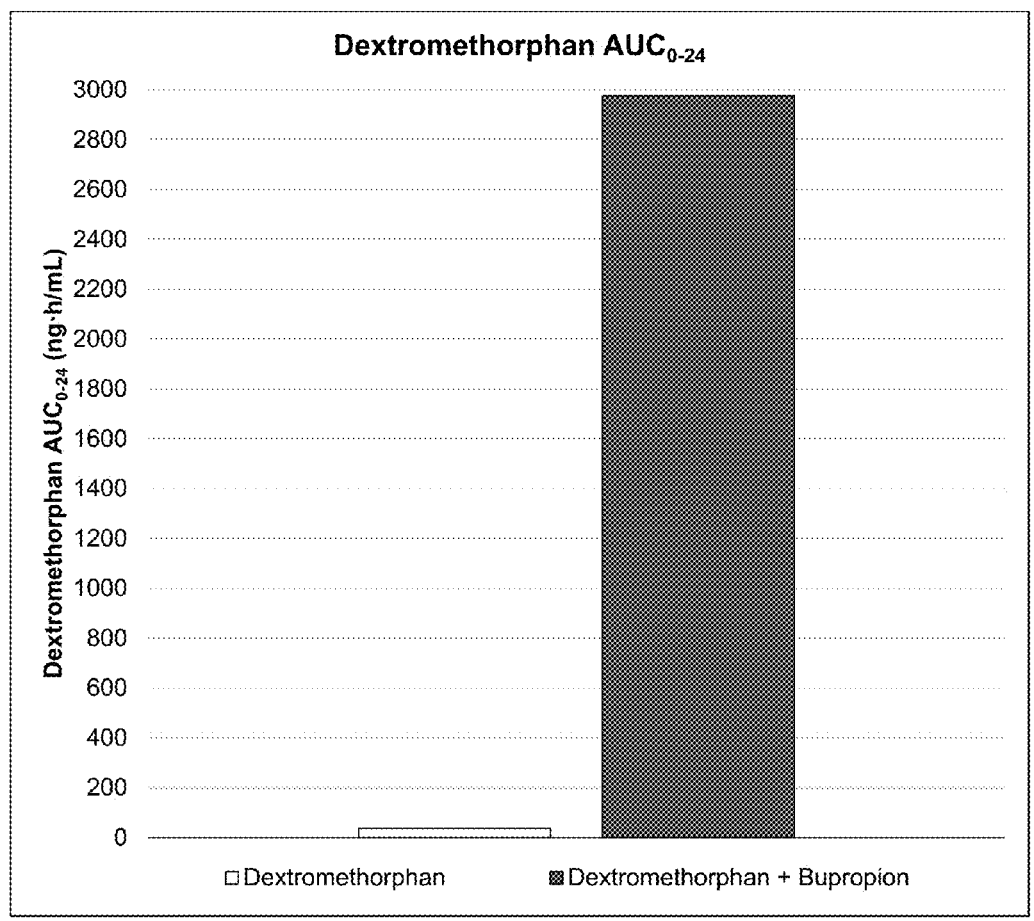
FIG. 3 depicts mean $AUC_{0-24}$ of dextromethorphan on Day 8 for subjects administered dextromethorphan alone or dextromethorphan and bupropion.
Figure 4:
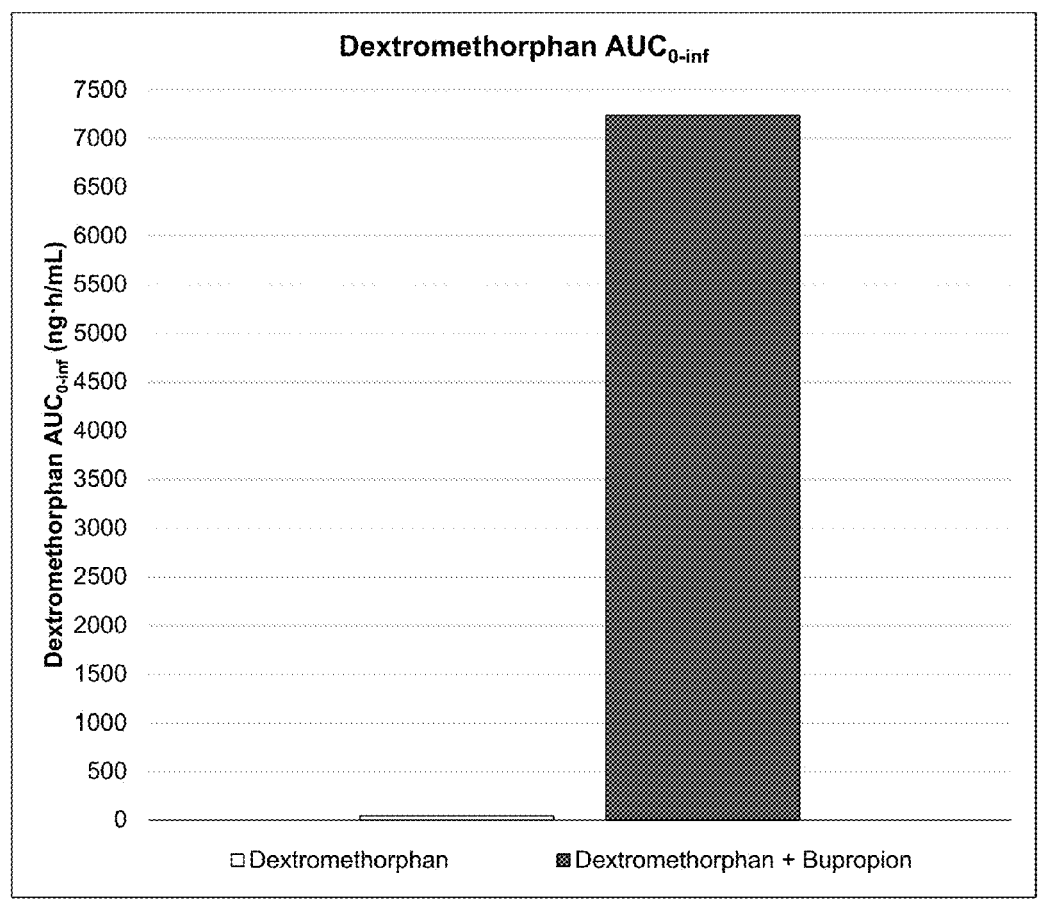
FIG. 4 depicts mean $AUC_{0-inf}$ of dextromethorphan on Day 8 for subjects administered dextromethorphan alone or dextromethorphan and bupropion.
Figure 5:
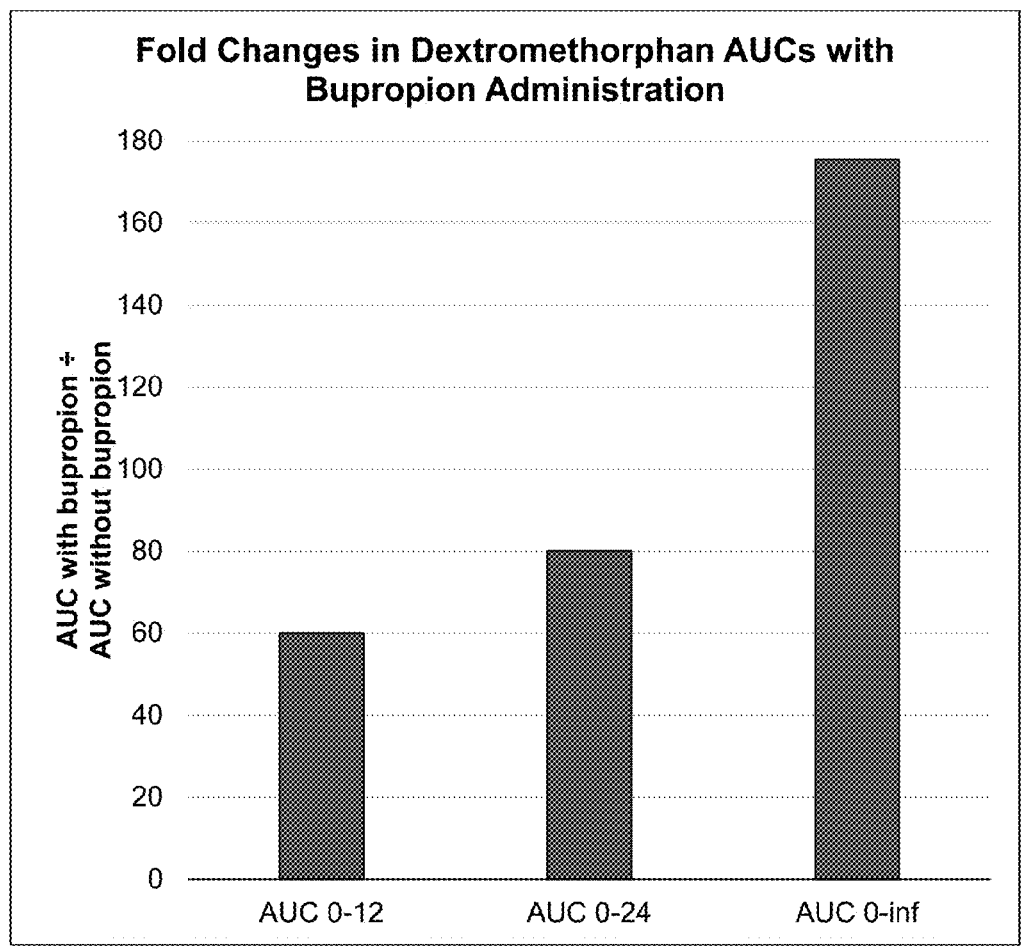
FIG. 5 depicts the fold changes in AUCs of dextromethorphan on Day 8 for subjects administered dextromethorphan alone as compared to dextromethorphan and bupropion.
Figure 6:
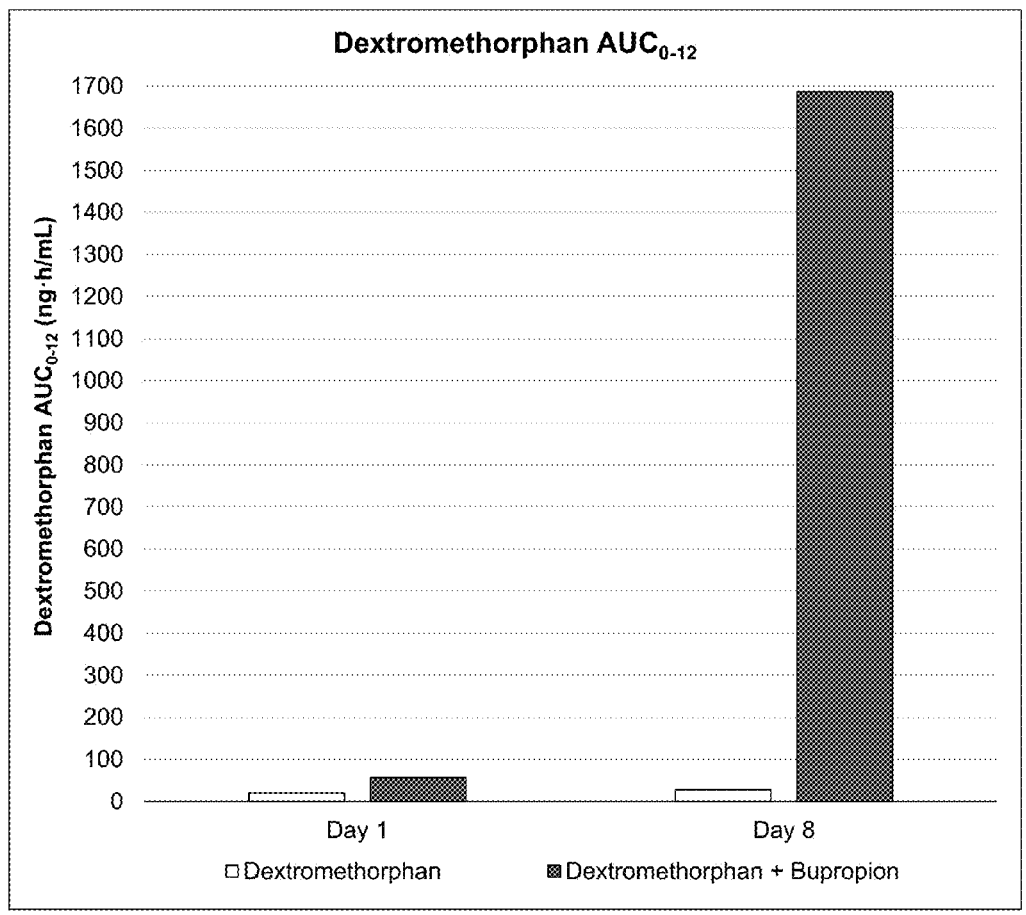
FIG. 6 depicts mean $AUC_{0-12}$ of dextromethorphan on Day 1 and Day 8 for subjects administered dextromethorphan alone or dextromethorphan and bupropion.

The AUC of dextromethorphan was significantly increased with administration of bupropion as show in FIGS. 2-4. As shown in FIG. 5 and Table 2A, administration of bupropion with dextromethorphan resulted in an approximately 60-fold, 80-fold, and 175-fold increase in mean dextromethorphan $AUC_{0-12}$, $AUC_{0-24}$, and $AUC_{0-inf}$, respectively on Day 8 as compared to administration of dextromethorphan alone. As shown in FIG. 6 and Table 2B, the increase in dextromethorphan AUC occurred as early as Day 1 (an approximate 3-fold increase in $AUC_{0-12}$).

TABLE 2A

Day 8 Values

| | Dextromethorphan (Group A) | Dextromethorphan + Bupropion (Group B) |
|---|---|---|
| $AUC_{0-12}$ (ng * hr/mL) | 28.1 | 1,686.3 |
| $AUC_{0-24}$ (ng * hr/mL) | 37.1 | 2,975.3 |
| $AUC_{0-inf}$ (ng * hr/mL) | 41.2 | 7,237.3 |
| $C_{max}$ (ng/mL) | 3.8 | 158.1 |
| $C_{min}$ (ng/mL) | 1.1 | 119.3 |
| $C_{avg}$ (ng/mL) | 2.3 | 140.5 |

TABLE 2B

Day 1 Values

| | Dextromethorphan (Group A) | Dextromethorphan + Bupropion (Group B) |
|---|---|---|
| $AUC_{0-12}$ (ng * hr/mL) | 20.1 | 56.5 |
| $C_{max}$ (ng/mL) | 3.0 | 8.7 |

Figure 7:
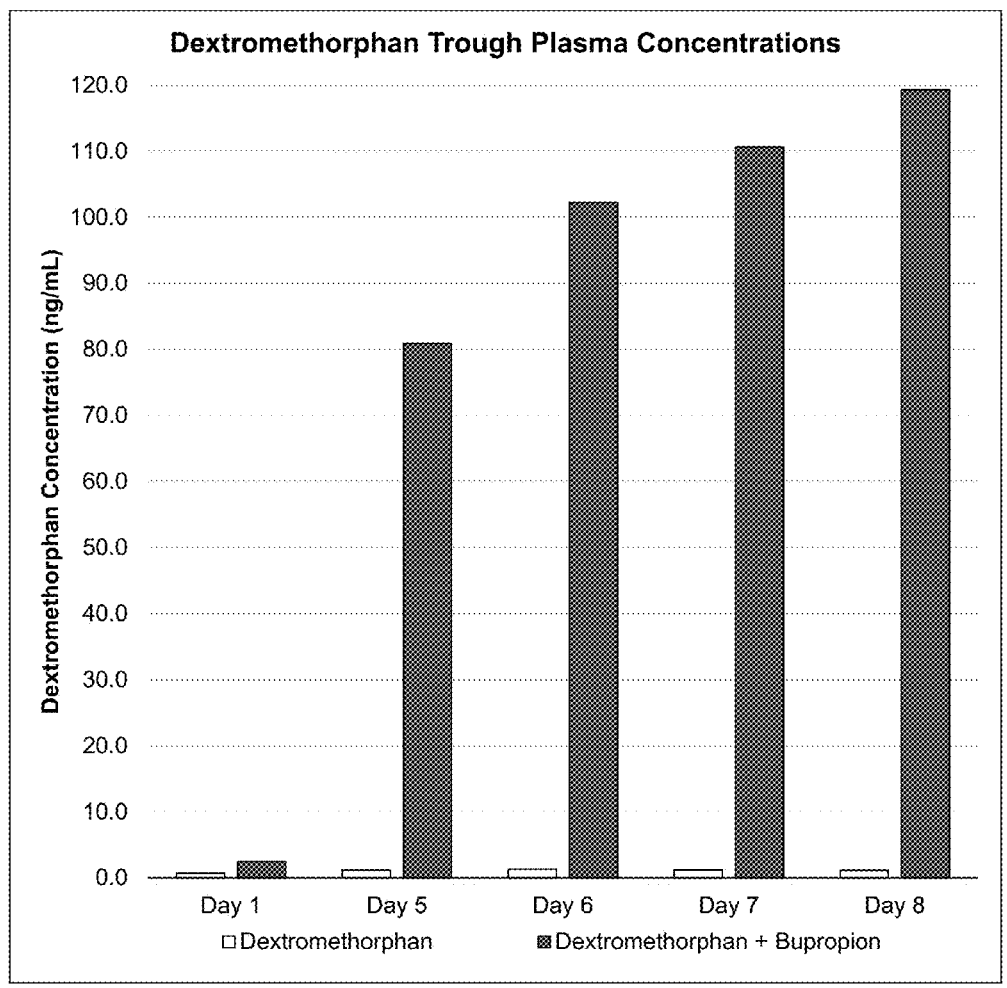
FIG. 7 depicts mean dextromethorphan trough plasma concentrations for subjects administered dextromethorphan alone or dextromethorphan and bupropion.

Trough plasma concentrations (also referred to as "minimum mean plasma concentrations" or "$C_{min}$") of dextromethorphan were significantly increased with administration of bupropion as illustrated in FIG. 7 and Tables 2A and 3. Administration of bupropion with dextromethorphan resulted in an approximately 105-fold increase in mean trough plasma concentration of dextromethorphan on Day 8 as compared to administration of dextromethorphan alone.

Figure 8:
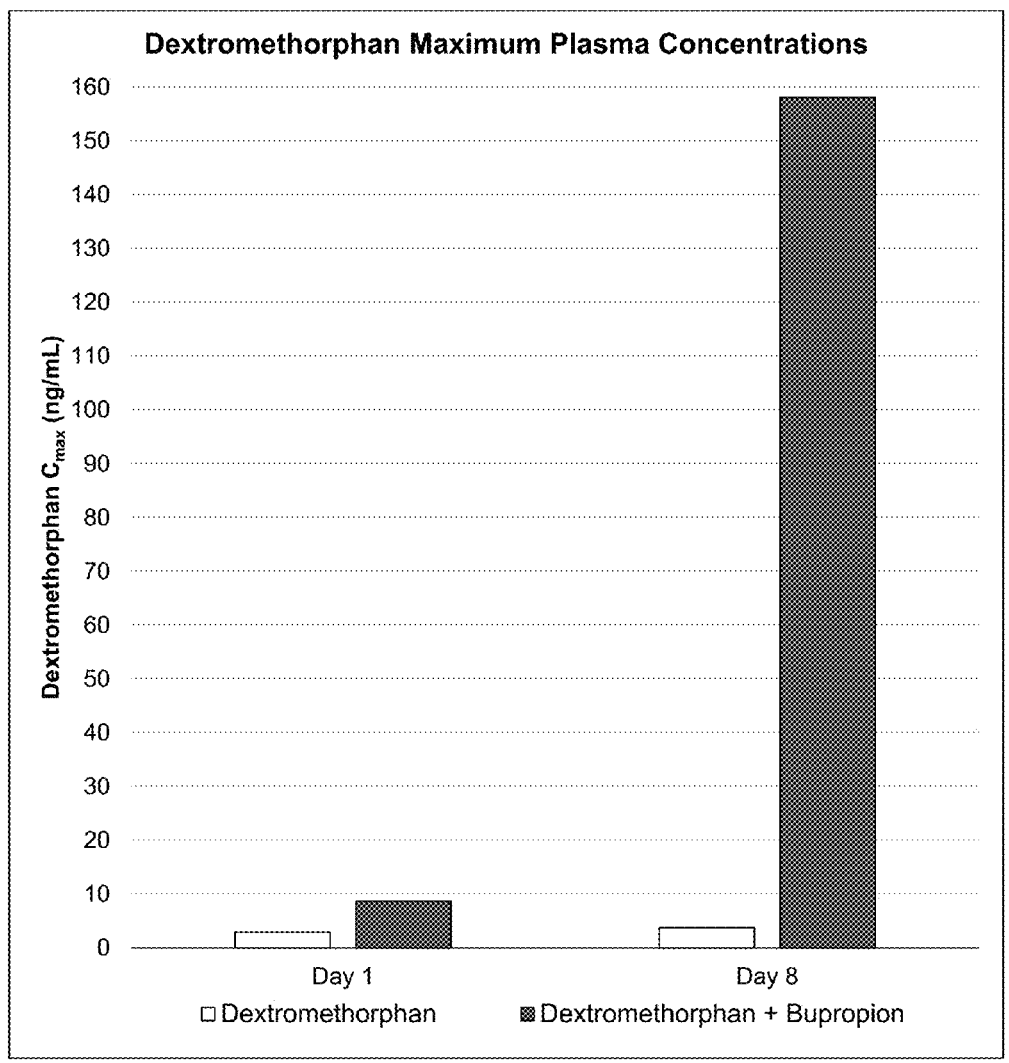
FIG. 8 depicts mean dextromethorphan maximum plasma concentrations on Day 1 and Day 8 for subjects administered dextromethorphan alone or dextromethorphan and bupropion.

Mean average plasma concentrations ($C_{avg}$) of dextromethorphan on Day 8 increased approximately 60-fold with bupropion administration as compared to administration of dextromethorphan alone, as illustrated in Table 2A. Maximum mean plasma concentrations ($C_{max}$) were also significantly increased as illustrated in FIG. 8 and Table 2A.

TABLE 3

Mean Trough Dextromethorphan Plasma Concentrations (ng/mL)

| | Dextromethorphan (Group A) | Dextromethorphan + Bupropion (Group B) | Fold Change |
|---|---|---|---|
| Day 1 | 0.7 | 2.5 | 3.5 |
| Day 5 | 1.2 | 80.9 | 70 |
| Day 6 | 1.3 | 102.2 | 78 |
| Day 7 | 1.2 | 110.6 | 94 |
| Day 8 | 1.1 | 119.3 | 105 |

The $T_{max}$ and elimination half life ($T_{1/2\ el}$) of dextromethorphan were significantly increased with administration of bupropion on Day 8. The increase of $T_{1/2\ el}$ shows that the metabolic lifetime of dextromethorphan was increased. Administration of bupropion with dextromethorphan resulted in a mean $T_{max}$ of 3.6 hours, compared to 2.3 hours for dextromethorphan alone. Administration of bupropion with dextromethorphan resulted in a mean $T_{1/2\ el}$ of 27.7 hours, compared to 6.6 hours for dextromethorphan alone.

Figure 9:
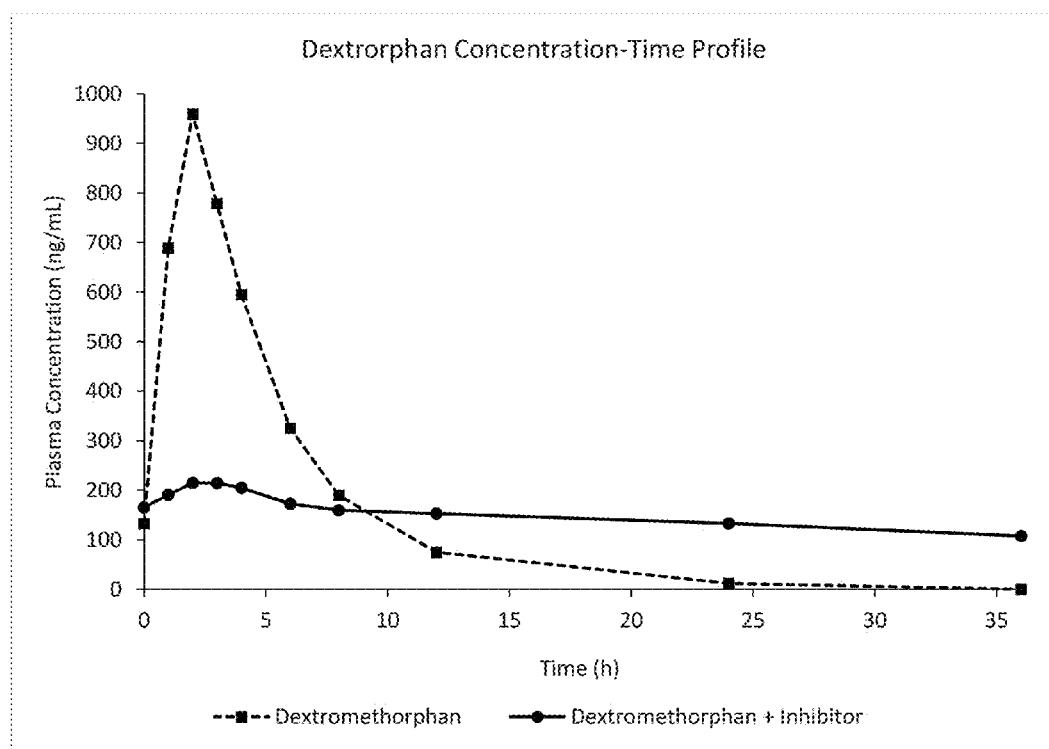
FIG. 9 is a plot of the mean plasma concentrations of dextrorphan over time after dosing on Day 8 for subjects administered dextromethorphan alone or dextromethorphan and bupropion.

Plasma concentrations of dextrorphan were significantly decreased with bupropion administration, as illustrated in FIG. 9 and Table 4.

TABLE 4

Mean Day 8 Dextrorphan Plasma Concentrations (ng/mL)

| Time (hours) | Dextromethorphan (Group A) | Dextromethorphan + Bupropion (Group B) |
|---|---|---|
| 0 | 132.4 | 165.3 |
| 1 | 688.9 | 190.7 |
| 2 | 959.1 | 214.9 |
| 3 | 778.1 | 214.4 |
| 4 | 594.9 | 205.1 |
| 6 | 324.7 | 172.5 |
| 8 | 189.6 | 159.6 |
| 12 | 74.8 | 152.8 |
| 24 | 12.2 | 133.0 |
| 36 | 0.1 | 107.6 |

Figure 10:
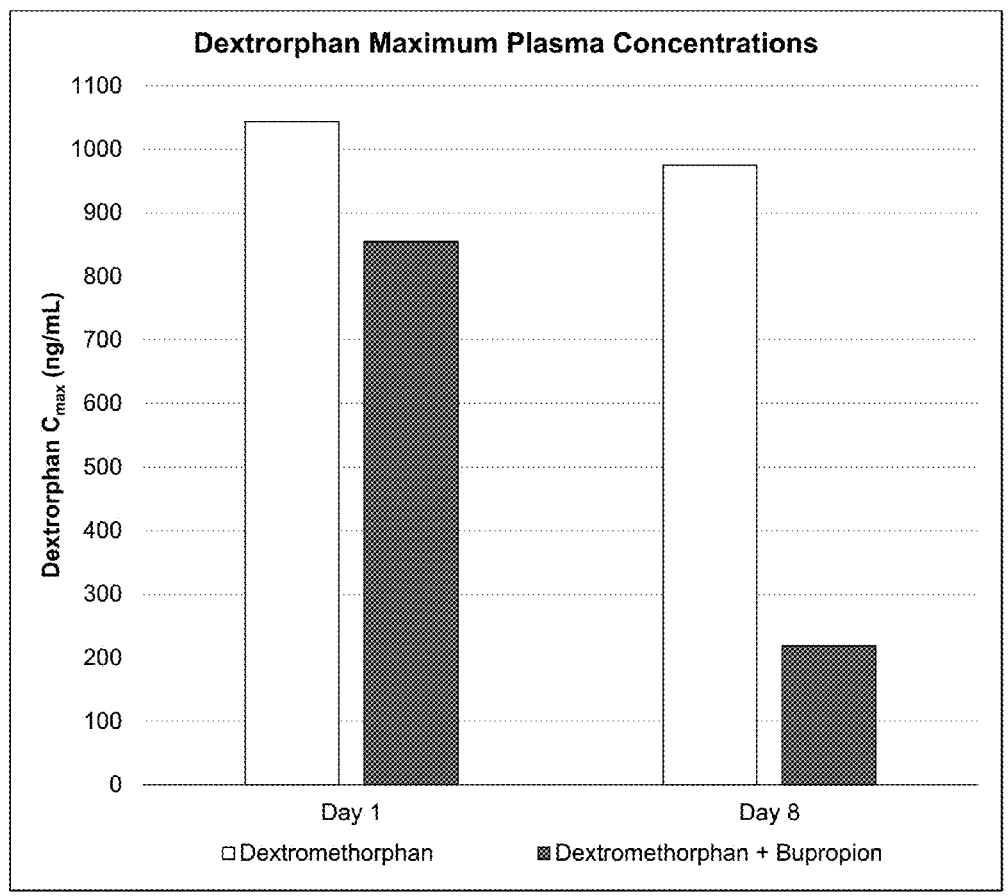
FIG. 10 depicts mean dextrorphan maximum plasma concentrations on Day 1 and Day 8 for subjects administered dextromethorphan alone or dextromethorphan and bupropion.
Figure 11:
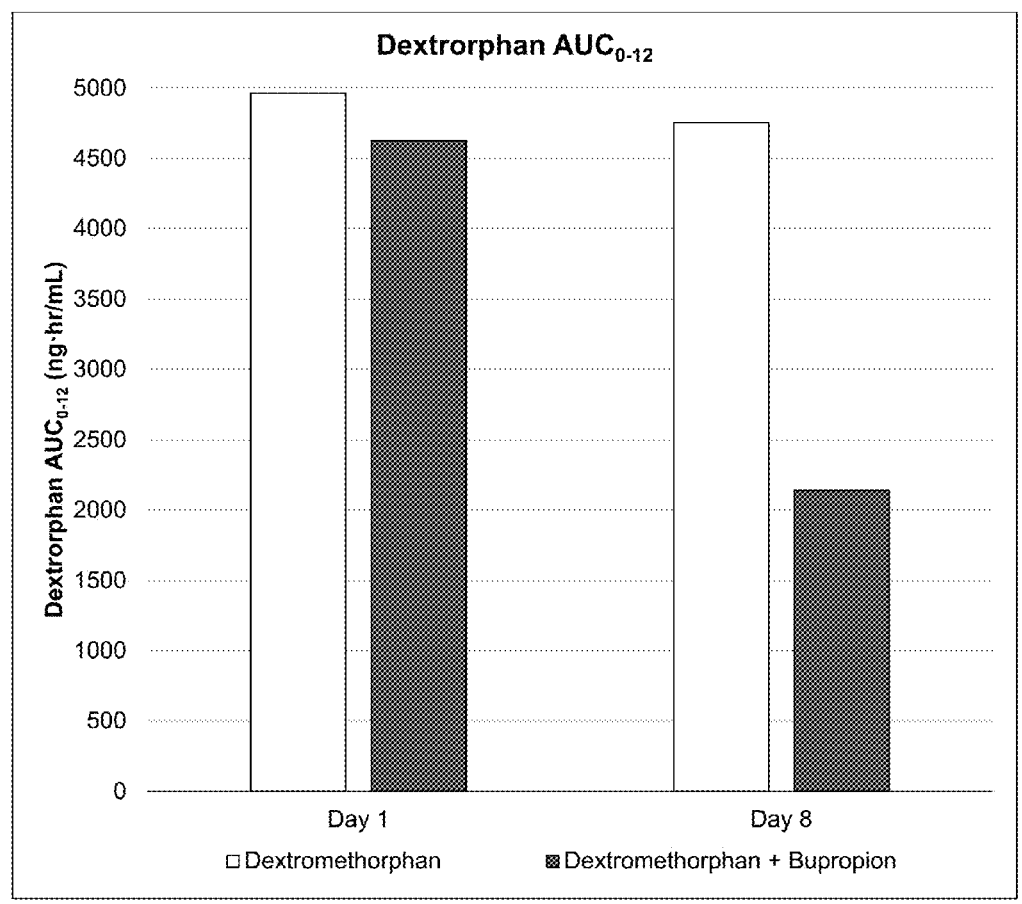
FIG. 11 depicts mean $AUC_{0-12}$ of dextrorphan on Day 1 and Day 8 for subjects administered dextromethorphan alone or dextromethorphan and bupropion.

As shown in FIGS. 10-11, there was an approximate 78% reduction in mean dextrorphan $C_{max}$, and an approximate 55% reduction in mean dextrorphan $AUC_{0-12}$ on Day 8 with administration of bupropion.

Phenotypic determination of dextromethorphan metabolizer status showed that no subjects in either treatment arm were poor metabolizers on Day 1. On Day 8 however, 100% of subjects treated with bupropion had converted to poor metabolizer status as compared to 0% of subjects treated with dextromethorphan alone. The mean plasma dextromethorphan/dextrorphan metabolic ratio increased from 0.01 on Day 1 to 0.71 on Day 8 with bupropion administration. The mean ratio in the group administered DM alone was 0.00 on Day 1 and remained unchanged on Day 8.

On Day 8, average plasma concentrations of bupropion, hydroxybupropion, erythrohydroxybupropion, and threohydroxybupropion were at least 10 ng/mL, 200 ng/mL, 20 ng/mL, and 100 ng/mL, respectively after bupropion administration.

As used in this section, the term "fold change" or "fold increase" refers to the ratio of a value for bupropion with dextromethorphan to the same value for dextromethorphan alone (i.e. the value for bupropion with dextromethorphan divided by the same value for dextromethorphan alone).

Example 2

The ability of various antidepressant compounds to inhibit the metabolism of dextromethorphan was examined using human liver microsomes. Each antidepressant compound was incubated at seven increasing concentrations (0.1-100 μM) in duplicate with human liver microsomes (0.5 mg/mL) in the presence of dextromethorphan (5 μM) at 37° C. The assay was performed in the presence of 2 mM NADPH in 100 mM potassium phosphate (pH 7.4) containing 5 mM magnesium chloride, in a 200 μL assay final volume.

After optimal incubation at 37° C., the reactions were terminated by addition of methanol containing internal standard for analytical quantification. The quenched samples were incubated at 4° C. for 10 minutes and centrifuged at 4° C. for 10 minutes. The supernatant was removed and the metabolite of dextromethorphan (dextrorphan) was analyzed by LC-MS/MS. A decrease in the formation of the metabolite compared to vehicle control was used to calculate an $IC_{50}$ value (the test concentration which produces 50% inhibition of dextromethorphan metabolism) for each antidepressant compound, with a lower $IC_{50}$ indicating greater potency.

Figure 12:
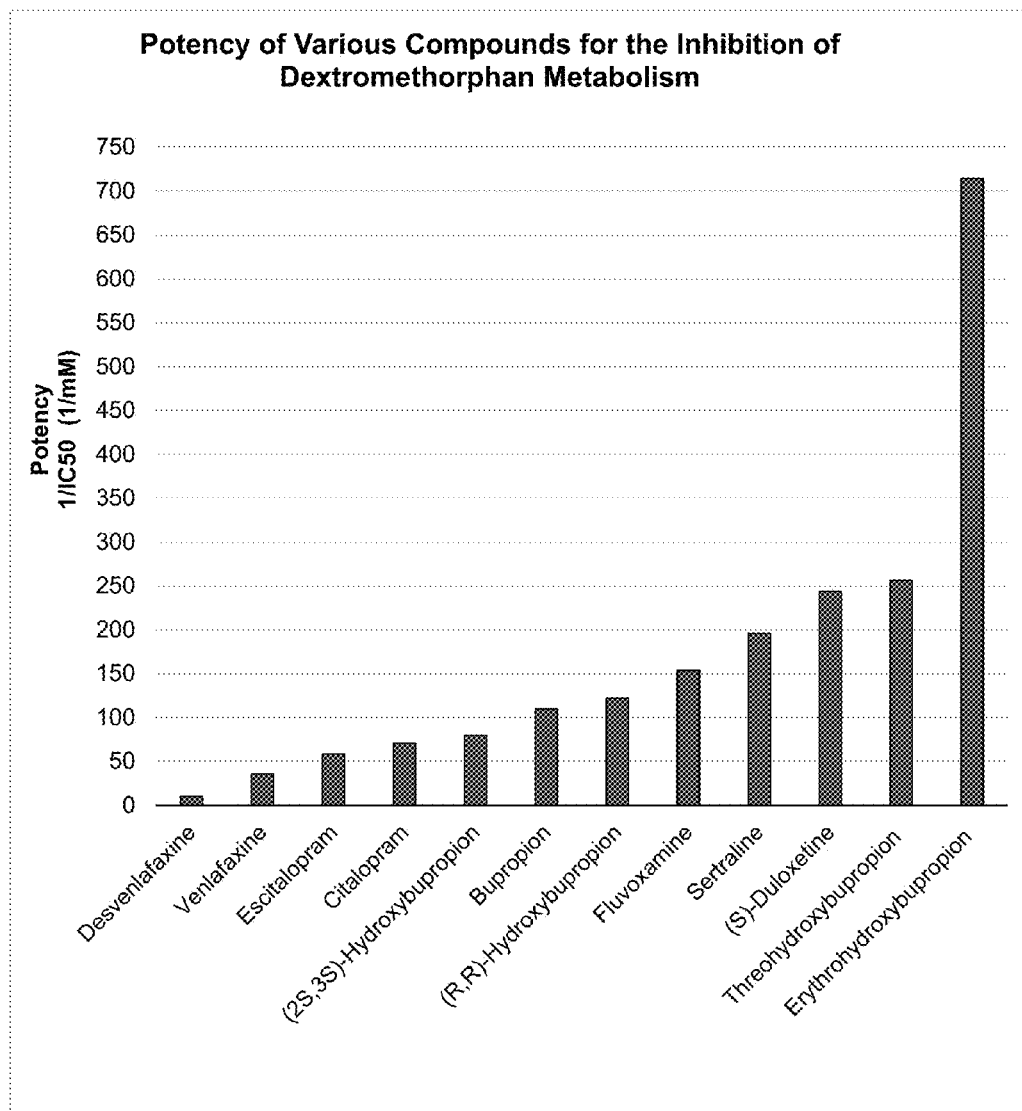
FIG. 12 depicts the potency of various antidepressant compounds for inhibition of the metabolism of dextromethorphan in human liver microsomes.

The results are summarized in Table 5 below, and the corresponding potencies are depicted in FIG. 12.

TABLE 5

| Test Compound | Mean $IC_{50}$ (μM) |
|---|---|
| Desvenlafaxine | 97.3 |
| Venlafaxine | 27.7 |
| Escitalopram | 17.1 |
| Citalopram | 14.1 |
| (2S,3S)-Hydroxybupropion | 12.5 |
| Bupropion | 9.1 |
| (R,R)-Hydroxybupropion | 8.2 |
| Fluvoxamine | 6.5 |
| Sertraline | 5.1 |
| (S)-Duloxetine | 4.1 |
| Threohydroxybupropion | 3.9 |
| Erythrohydroxybupropion | 1.4 |

Unless otherwise indicated, all numbers expressing quantities of ingredients, properties such as molecular weight, reaction conditions, and so forth used in the specification and claims are to be understood in all instances as indicating both the exact values as shown and as being modified by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

The invention claimed is:

1. A method of extending dextromethorphan plasma levels in a human being that is an extensive metabolizer of dextromethorphan and is in need of treatment with dextromethorphan, comprising co-administering: 1) a hydroxybupropion, a threohydroxybupropion, an erythrohydroxybupropion, or a bupropion with 2) a dextromethorphan, to the human being once or twice a day for at least eight consecutive days, wherein the daily dose of the dextromethorphan is about 15 mg to about 300 mg, and co-administering the hydroxybupropion, the threohydroxybupropion, the erythrohydroxybupropion, or the bupropion with the dextromethorphan results in a $C_{avg}$ of the dextromethorphan that, on the eighth day, is at least about 20 times the $C_{avg}$ that would be achieved by administering the same amount of the dextromethorphan without the hydroxybupropion, the threohydroxybupropion, the erythrohydroxybupropion, or the bupropion for eight consecutive days.

2. The method of claim 1, wherein the daily dose of the dextromethorphan is about 20 mg to about 250 mg.

3. The method of claim 1, wherein the daily dose of the dextromethorphan is about 30 mg to about 200 mg.

4. The method of claim 1, wherein the daily dose of the dextromethorphan is about 40 mg to about 150 mg.

5. The method of claim 1, wherein the dextromethorphan is co-administered in a dosage form that contains about 40 mg to about 50 mg of the dextromethorphan.

6. The method of claim 4, wherein the dextromethorphan is co-administered in a dosage form that contains about 40 mg to about 50 mg of the dextromethorphan.

7. The method of claim 1, wherein the hydroxybupropion, the threohydroxybupropion, the erythrohydroxybupropion, or the bupropion and the dextromethorphan are co-administered together in a single, solid oral dosage form.

8. The method of claim 7, wherein the single solid oral dosage form further comprises a binder, a disintegrating agent, or a lubricant.

9. The method of claim 1, further comprising co-administering the hydroxybupropion, the threohydroxybupropion, the erythrohydroxybupropion, or the bupropion with the dextromethorphan to the human being once or twice a day for at least 14 consecutive days.

10. The method of claim 1, further comprising co-administering the hydroxybupropion, the threohydroxybupropion, the erythrohydroxybupropion, or the bupropion with the dextromethorphan to the human being once or twice a day for at least 30 consecutive days.

11. The method of claim 1, comprising co-administering the hydroxybupropion, the threohydroxybupropion, the erythrohydroxybupropion, or the bupropion with the dextromethorphan to the human being twice a day.

12. The method of claim 1, wherein, on the eighth day, the $C_{avg}$ of the dextromethorphan is at least about 10 ng·hr/mL.

13. The method of claim 1, wherein, on the eighth day, the $C_{avg}$ of the dextromethorphan is at least about 100 ng·hr/mL.

14. The method of claim 1, wherein the hydroxybupropion, the threohydroxybupropion, the erythrohydroxybupropion, the bupropion, or the dextromethorphan is deuterium-modified.

15. The method of claim 14, wherein the dextromethorphan is deuterium-modified.

16. A method of extending dextromethorphan plasma levels in a human being that is an extensive metabolizer of dextromethorphan and is in need of treatment with dextromethorphan, comprising co-administering: 1) a hydroxybupropion, a threohydroxybupropion, an erythrohydroxybupropion, or a bupropion with 2) a dextromethorphan, to the human being once or twice a day for at least eight consecutive days, wherein the daily dose of the dextromethorphan is about 20 mg to about 250 mg, and co-administering the hydroxybupropion, the threohydroxybupropion, the erythrohydroxybupropion, or the bupropion with the dextromethorphan results in a $C_{avg}$ of the dextromethorphan that, on the eighth day, is at least about 15 times the $C_{avg}$ that would be achieved by administering the same amount of the dextromethorphan without the hydroxybupropion, the threohydroxybupropion, the erythrohydroxybupropion, or the bupropion for eight consecutive days.

17. The method of claim 16, wherein the dextromethorphan is deuterium-modified.

18. The method of claim 16, wherein the daily dose of the dextromethorphan is about 30 mg to about 150 mg.

19. The method of claim 16, wherein the dextromethorphan is co-administered in a dosage form that contains about 40 mg to about 50 mg of the dextromethorphan.

20. The method of claim 16, wherein the dextromethorphan with the hydroxybupropion, the threohydroxybupropion, the erythrohydroxybupropion, or the bupropion is co-administered in an oral dosage form.

21. The method of claim 20, wherein the oral dosage form is solid.

22. A method of extending dextromethorphan plasma levels in a human being that is an extensive metabolizer of dextromethorphan and is in need of treatment with dextromethorphan, comprising co-administering: 1) a hydroxybupropion, a threohydroxybupropion, an erythrohydroxybupropion, or a bupropion with 2) a dextromethorphan, to the human being once or twice a day for at least eight consecutive days, wherein the daily dose of the dextromethorphan is about 50 mg to about 400 mg, and co-administering the hydroxybupropion, the threohydroxybupropion, the erythrohydroxybupropion, or the bupropion with the dextromethorphan results in a $C_{avg}$ of the dextromethorphan that, on the eighth day, is at least about 15 times the $C_{avg}$ that would be achieved by administering the same amount of the dextromethorphan without the hydroxybupropion, the threohydroxybupropion, the erythrohydroxybupropion, or the bupropion for eight consecutive days.

23. The method of claim 22, wherein the dextromethorphan is co-administered with the hydroxybupropion or the bupropion.

24. The method of claim 22, wherein the dextromethorphan is co-administered with the threohydroxybupropion or the bupropion.

25. The method of claim 22, wherein the dextromethorphan is co-administered with the erythrohydroxybupropion or the bupropion.

* * * * *